US012678453B2

(12) United States Patent
Johnston

(10) Patent No.: US 12,678,453 B2
(45) Date of Patent: Jul. 14, 2026

(54) AEROSOLIZED FORMULATIONS OF HIV PROTEASE INHIBITORS FOR THE TREATMENT OF AIRWAY REFLUX

(71) Applicant: The Medical College of Wisconsin, Inc., Milwaukee, WI (US)

(72) Inventor: Nikki Johnston, Oconomowoc, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 357 days.

(21) Appl. No.: 18/047,173

(22) Filed: Oct. 17, 2022

(65) Prior Publication Data

US 2023/0078695 A1     Mar. 16, 2023

Related U.S. Application Data

(63) Continuation-in-part of application No. PCT/US2021/027758, filed on Apr. 16, 2021.

(60) Provisional application No. 63/011,039, filed on Apr. 16, 2020.

(51) Int. Cl.
| | |
|---|---|
| *A61K 31/665* | (2006.01) |
| *A61K 9/00* | (2006.01) |
| *A61P 1/04* | (2006.01) |

(52) U.S. Cl.
CPC ............ *A61K 31/665* (2013.01); *A61K 9/008* (2013.01); *A61P 1/04* (2018.01)

(58) Field of Classification Search
CPC ..... A61P 1/04; A61K 31/427; A61K 31/4725; A61K 31/635; A61K 31/665; A61K 9/008
See application file for complete search history.

(56) References Cited

U.S. PATENT DOCUMENTS

| | | |
|---|---|---|
| 2003/0049204 A1 | 3/2003 | Leyland-Jones |
| 2006/0024238 A1 | 2/2006 | Barth et al. |
| 2007/0154547 A1 | 7/2007 | Flanner et al. |
| 2007/0298025 A1* | 12/2007 | Harosh ...................... A61P 3/04 424/94.66 |
| 2008/0020018 A1 | 1/2008 | Moodley et al. |
| 2016/0303133 A1 | 10/2016 | Dudley et al. |
| 2018/0153802 A1 | 6/2018 | Perrett et al. |
| 2020/0368147 A1 | 11/2020 | Meltzer et al. |

FOREIGN PATENT DOCUMENTS

| | | |
|---|---|---|
| CN | 106511344 A | 3/2017 |
| WO | 2006050999 A2 | 5/2006 |
| WO | 2008080092 A2 | 7/2008 |
| WO | 2008156632 A1 | 12/2008 |
| WO | WO-2009073878 A1 * | 6/2009 ........... A61K 31/717 |

OTHER PUBLICATIONS

Peptest, Relux: the role of Pepsin explained, Mar. 3, 2016, pp. 1-8 (Year: 2016).*
Mainie, I. et al., Acid and Non-Acid Reflux in Patients with Persistent Symptoms Despite Acid Suppressive Therapy: A Multicentre Study Using Combined Ambulatory Impedance-pH Monitoring, Gut, 2006, 55(10):1398-1402.
Marshall, S. et al., Detection of Pepsin and IL-8 in Saliva of Adult Asthmatic Patients, Journal of Asthma and Allergy, 2019, 12:155-161.
Martinucci, I. et al., Optimal Treatment of Laryngopharyngeal Reflux Disease, Therapeutic Advances in Chronic Disease, 2013, 4(6):287-301.
Masaany, M. et al., Empirical Treatment with Pantoprazole as a Diagnostic Tool for Symptomatic Adult Laryngopharyngeal Reflux, Journal of Laryngology & Otology, 2011, 125(5):502-508.
McCoy, A. et al., Phaser Crystallographic Software, Journal of Applied Crystallography, 2007, 40(4):658-674.
McGlashan, J. et al., The Value of a Liquid Alginate Suspension (Gaviscon Advance) in the Management of Laryngopharyngeal Reflux, European Archives of Otorhinolaryngology, 2009, 266:243-251.
McQuaid, K. et al., Systematic Review: The Role of Bile Acids in the Pathogenesis of Gastro-Oesophageal Reflux Disease and Related Neoplasia, Alimentary Pharmacology & Therapeutics, 2011, 34(2):146-165.
Nagahama, K. et al., Essential Role of Pepsin in Pathogenesis of Acid Reflux Esophagitis in Rats, Digestive Diseases and Sciences, 2006, 51:303-309.
Niu, K. et al., Pepsin Promotes Laryngopharyngeal Neoplasia by Modulating Signaling Pathways to Induce Cell Proliferation, PLoS One, 2020, 15(1):e0227408, pp. 1-14.
Noordzij, J. et al., Evaluation of Omeprazole in the Treatment of Reflux Laryngitis: A Prospective, Placebo-Controlled, Randomized, Double-Blind Study, Laryngoscope, 2001, 111(12):2147-2151.
Olp, M. et al., An Online Tool for Calculating Initial Rates from Continuous Enzyme Kinetic Traces, bioRxiv, 2019, 700138, pp. 1-12.

(Continued)

*Primary Examiner* — Brian-Yong S Kwon
*Assistant Examiner* — Lyndsey M Beckhardt
(74) *Attorney, Agent, or Firm* — Quarles & Brady LLP

(57) ABSTRACT

The present invention provides methods of treating airway reflux using an HIV protease inhibitor that is capable of binding to and inhibiting the enzymatic activity of pepsin. Compositions comprising aerosolized formulations of HIV protease inhibitors are also provided.

11 Claims, 37 Drawing Sheets

Specification includes a Sequence Listing.

(56) References Cited

OTHER PUBLICATIONS

Olp, M. et al., ICEKAT: An Interactive Online Tool for Calculating Initial Rates from Continuous Enzyme Kinetic Traces, BMC Bioinformatics, 2020, 21:186, pp. 1-12.
Otwinowski, Z. et al., [20] Processing of X-ray Diffraction Data Collected in Oscillation Mode, Methods in Enzymology, 1997, 276:307-326.
Park, W. et al., Laryngopharyngeal Reflux: Prospective Cohort Study Evaluating Optimal Dose of Proton-Pump Inhibitor Therapy and Pretherapy Predictors of Response, Laryngoscope, 2005, 115(7):1230-1238.
Parsel, S. et al., Gastroesophageal and Laryngopharyngeal Reflux Associated with Laryngeal Malignancy: A Systematic Review and Meta-Analysis, Clinical Gastroenterology and Hepatology, 2019, 17(7):1253-1264.
Pearson, J. et al., Review Article: Reflux and its Consequences—the Laryngeal, Pulmonary and Oesophageal Manifestations, Alimentary Pharmacology and Therapeutics, 2011, 33(Suppl 1):1-71.
Perkins, E. et al., Ideal Particle Sizes for Inhaled Steroids Targeting Vocal Granulomas: Preliminary Study Using Computational Fluid Dynamics, Otolaryngology Head and Neck Surgery, 2018, 158(3):511-519.
Perng, D. et al., Exposure of Airway Epithelium to Bile Acids Associated with Gastroesophageal Reflux Symptoms: A Relation to Transforming Growth Factor-B1 Production and Fibroblast Proliferation, Chest, 2007, 132(5):1548-1556.
Pham, T. et al., Development and Characterization of a Surgical Mouse Model of Reflux Esophagitis and Barrett's Esophagus, Journal of Gastrointestinal Surgery, 2014, 18(2):234-241.
Piper, D. et al., pH Stability and Activity Curves of Pepsin with Special Reference to their Clinical Importance, Gut, 1965, 6(5):506-508.
Potluri, S. et al., Comparison of a Salivary/Sputum Ppepsin Assay with 24-hour Esophageal pH Monitoring for Detection of Gastric Reflux into the Proximal Esophagus, Oropharynx, and Lung, Digestive Diseases and Sciences, 2003, 48:1813-1817.
Powell, J. et al., Mucosal Changes in Laryngopharyngeal Reflux—Prevalence, Sensitivity, Specificity and Assessment, Laryngoscope, 2013, 123(4):985-991.
Raabe, O. et al., Regional Deposition of Inhaled Monodisperse Coarse and Fine Aerosol Particles in Small Laboratory Animals, Ann. Occup. Hyg., 1988, 32(Suppl 1):53-63.
Rader, B., Alkaline Phosphatase, an Unconventional Immune Protein, Frontiers in Immunology, 2017, vol. 8, Article 897, pp. 1-6.
Reale, M. et al., Induction of Alkaline Phosphatase Generation by il-1β and LPS on Human Neutrophils and Macrophages and Lack of Inhibition by Interleukin-1 Receptor Antagonist, Inflammopharmacology, 1995, 3:25-34.
Rees, L. et al., The Mucosal Immune Response to Laryngopharyngeal Reflux, American Journal of Respiratory and Critical Care Medicine, 2008, 177(11):1187-1193.
Reichel, O. et al., Double-Blind, Placebo-Controlled Trial with Esomeprazole for Symptoms and Signs Associated with Laryngopharyngeal Reflux, Otolaryngology Head and Neck Surgery, 2008, 139(3):414-420.
Reimer, C. et al., Management of Laryngopharyngeal Reflux with Proton Pump Inhibitors, Therapeutics and Clinical Risk Management, 2008, 40(1):225-233.
Reulbach, T. et al., Occult Laryngeal Pathology in a Community-Based Cohort, Otolaryngology Head and Neck Surgery, 2001, 124(4):448-450.
Riley, C. et al., Association of Gastroesophageal Reflux with Malignancy of the Upper Aerodigestive Tract in Elderly Patients, JAMA Otolaryngology Head & Neck Surgery, 2018, 144(2):140-148.
Riley, C. et al., Detection of Laryngeal Carcinoma in the U.S. Elderly Population with Gastroesophageal Reflux Disease, Head & Neck, 2019, 41(5):1434-1440.
Roberts, N. et al., Comparative Pepstatin Inhibition Studies on Individual Human Pepsins and Pepsinogens 1, 3 and 5 (gastricsin) and Pig Pepsin A, Journal of Enzyme Inhibition and Medicinal Chemistry, 2003, 18(3):209-217.
Roh, J. et al., Effect of Acid and Pepsin on Glottic Wound Healing: A Simulated Reflux Model, Archives of Otolaryngology Head & Neck Surgery, 2006, 132(9):995-1000.
Samuels, T. et al., Pepsin as a Causal Agent of Inflammation During Nonacidic Reflux, Otolaryngology Head and Neck Surgery, 2009, 141(5):559-563.
Samuels, T. et al., Pepsin as a Marker of Extraesophageal Reflux, Annals of Otology, Rhinology & Laryngology, 2010, 119(3):203-208.
Samuels, T. et al., Curcumin and Anthocyanin Inhibit Pepsin-Mediated Cell Damage and Carcinogenic Changes in Airway Epithelial Cells, Annals of Otology, Rhinology & Laryngology, 2013, 122(10):632-641.
Samuels, T. et al., Esophageal Pepsin and Proton Pump Synthesis in Barrett's Esophagus and Esophageal Adenocarcinoma, Laryngoscope, 2019, 129(12):2687-2695.
Samuels, T. et al., Pepsin in Gastroesophageal and Extraesophageal Reflux: Molecular Pathophysiology and Diagnostic Utility, Current Opinion in Otolaryngology & Head and Neck Surgery, 2020, 28(6):401-409.
Samuels, T. et al., RNA Sequencing Reveals Cancer-Associated Changes in Laryngeal Cells Exposed to Non-Acid Pepsin, Laryngoscope, 2021, 131(1):121-129.
Sasaki, C. et al., The In Vitro Effect of Acidic-Pepsin on Nuclear Factor KappaB Activation and Its Related Oncogenic Effect on Normal Human Hypopharyngeal Cells, PLOS One, 2016, 11(12):e0168269, pp. 1-18.
Sasaki, C. et al., Weakly Acidic Bile is a Risk Factor for Hypopharyngeal Carcinogenesis Evidenced by DNA Damage, Antiapoptotic Function, and Premalignant Dysplastic Lesions In Vivo, Cancers, 2021, 13(4):852, pp. 1-15.
Schade, S. et al., BODIPY-α-Casein, a pH-independent Protein Substrate for Protease Assays using Fluorescence Polarization, Analytical Biochemistry, 1996, 243(1):1-7.
Sharma, N. et al., Further Comment on Proton Pump Inhibitor Failures, Clinical Gastroenterology and Hepatology, 2009, 7(3):363.
Sharma, U. et al., Alkaline Phosphatase: An Overview, Indian Journal of Clinical Biochemistry, 2014, 29:269-278.
Sidwa, F. et al., Surgical Treatment of Extraesophageal Manifestations of Gastroesophageal Reflux Disease, World Journal of Surgery, 2017, 41:2566-2571.
Sone, M. et al., Otitis Media in Adults as a Symptom of Gastroesophageal Reflux, Otolaryngology Head and Neck Surgery, 2007, 136(1):19-22.
Steward, D. et al., Proton Pump Inhibitor Therapy for Chronic Laryngo-Pharyngitis: A Randomized Placebo-Control Trial, Otolaryngology Head and Neck Surgery, 2004, 131(4):342-350.
Tae, K. et al., The Role of Laryngopharyngeal Reflux as a Risk Factor in Laryngeal Cancer: A Preliminary Report, Clinical and Experimental Otorhinolaryngology, 2011, 4(2):101-104.
Tamhankar, A. et al., Omeprazole does not Reduce Gastroesophageal Reflux: New Insights using Multichannel Intraluminal Impedance Technology, Journal of Gastrointestinal Surgery, 2004, 8:888-896.
Tan, J. et al., Pepsin Promotes IL-8 Signaling-Induced Epithelial-Mesenchymal Transition in Laryngeal Carcinoma, Cancer Cell International, 2019, 19:64, pp. 1-13.
Tutuian, R. et al., Nonacid Reflux in Patients with Chronic Cough on Acid-Suppressive Therapy, Chest, 2006, 130(2):386-391.
Tutuian, R. et al., Characteristics of Symptomatic Reflux Episodes on Acid Suppressive Therapy, American Journal of Gastroenterology, 2008, 103(5):1090-1096.
Vaezi, M., Extraesophageal Manifestations of Gastroesophageal Reflux Disease, Clinical Cornerstone, 2003, 5(4):32-38.
Vaezi, M. et al., Treatment of Chronic Posterior Laryngitis with Esomeprazole, Laryngoscope, 2006, 116(2):254-260.
Vaezi, M., Gastroesophageal Reflux-Related Chronic Laryngitis: Con, Archives of Otolaryngology Head & Neck Surgery, 2010, 136(9):908-909.

(56) References Cited

OTHER PUBLICATIONS

Weitzendorfer, M. et al., Pepsin and Oropharyngeal pH Monitoring to Diagnose Patients with Laryngopharyngeal Reflux, Laryngoscope, 2020, 130(7):1780-1786.

Wight, R. et al., Current Theories for the Development of Non-smoking and Nondrinking Laryngeal Carcinoma, Current Opinion in Otolaryngology & Head and Neck Surgery, 2003, 11(2):73-77.

Wire, M. et al., Fosamprenavir: Clinical Pharmacokinetics and Drug Interactions of the Amprenavir Prodrug, Clinical Pharmacokinetics, 2006, 45:137-168.

Wo, J. et al., Double-Blind, Placebo-Controlled Trial with Single-Dose Pantoprazole for Laryngopharyngeal Reflux, American Journal of Gastroenterology, 2006, 101(9):1972-1978.

Xie, Y. et al., In Vitro and In Vivo Lung Deposition of Coated Magnetic Aerosol Particles, Journal of Pharmaceutical Sciences, 2010, 99(11):4658-4668.

Yellon, R. et al., Subglottic Injury, Gastric Juice, Corticosteroids, and Peptide Growth Factors in a Porcine Model, Laryngoscope, 1998, 108(6):854-862.

Zalvan, C. et al., A Comparison of Alkaline Water and Mediterranean Diet vs Proton Pump Inhibition for Treatment of Laryngopharyngeal Reflux, JAMA Otolaryngology Head & Neck Surgery, 2017, 143(10):1023-1029.

Zhang, C. et al., Nissen Fundoplication vs Proton Pump Inhibitors for Laryngopharyngeal Reflux Based on pH-monitoring and Symptom-scale, World Journal of Gastroenterology, 2017, 23(19):3546-3555.

PCT International Search Report and Written Opinion, PCT/US2021/027758, Sep. 23, 2021, 14 pages.

European Patent Office, Extended Search Report, Application No. 21788194, filed Apr. 19, 2024, 9 pages.

China National Intellectual Property Administration, First Office Action and Search Report, Application No. 202180036213.8, Oct. 26, 2024, 18 pages.

Hvid-Jensen, F. et al., Proton Pump Inhibitor Use may not Prevent High-Grade Dysplasia and Oesophageal Adenocarcinoma in Barrett's Oesophagus: A Nationwide Study of 9883 Patients, Alimentary Pharmacology and Therapeutics, 2014, 39(9):984-991.

Iqbal, M. et al., Outcome of Surgical Fundoplication for Extraesophageal (Atypical) Manifestations of Gastroesophageal Reflux Disease in Adults: A Systematic Review, Journal of Laparoendoscopic & Advanced Surgical Techniques, 2008, 18(6):789-796.

Iqbal, M. et al., Outcome of Surgical Fundoplication for Extra-Oesophageal Symptoms of Reflux, Surgical Endoscopy, 2009, 23:557-561.

Johnston, N. et al., Cell Biology of Laryngeal Epithelial Defenses in Health and Disease: Further Studies, Annals of Otology, Rhinology & Laryngology, 2003, 112(6):481-491.

Johnston, N. et al., Pepsin and Carbonic Anhydrase Isoenzyme III as Diagnostic Markers for Laryngopharyngeal Reflux Disease, Laryngoscope, 2004, 114(12):2129-2134.

Johnston, N. et al., Effect of Pepsin on Laryngeal Stress Protein (Sep70, Sep53, and Hsp70) Response: Role in Laryngopharyngeal Reflux Disease, Annals of Otology, Rhinology & Laryngology, 2006, 115(1):47-58.

Johnston, N. et al., Activity/Stability of Human Pepsin: Implications for Reflux Attributed Laryngeal Disease, Laryngoscope, 2007, 117(6):1036-1039.

Johnston, N. et al., Receptor-Mediated Uptake of Pepsin by Laryngeal Epithelial Cells, Annals of Otology, Rhinology & Laryngology, 2007, 116(12):934-938.

Johnston, N. et al., Pepsin in Nonacidic Refluxate can Damage Hypopharyngeal Epithelial Cells, Annals of Otology, Rhinology & Laryngology, 2009, 118(9):677-685.

Johnston, N. et al., Rationale for Targeting Pepsin in the Treatment of Reflux Disease, Annals of Oncology Rhinology & Laryngology, 2010, 119(8):547-558.

Johnston, N. et al., Pepsin Promotes Proliferation of Laryngeal and Pharyngeal Epithelial Cells, Laryngoscope, 2012, 122(6):1317-1325.

Johnston, N. et al., Pepsin: Biomarker, Mediator, and Therapeutic Target for Reflux and Aspiration, Annals of the New York Academy of Sciences, 2018, 1434(1):282-289.

Johnston, N. et al., Oral and Inhaled Fosamprenavir Reverses Pepsin-Induced Damaged in a Laryngopharyngeal Reflux Mouse Model, Laryngoscope, 2022, 00:1-11.

Jolley, M., Fluorescence Polarization Assays for the Detection of Proteases and Their Inhibitors, Journal of Biomolecular Screening, 1996, 1(1):33-38.

Joosten, R. et al., The PDB_REDO Server for Macromolecular Structure Model Optimization, IUCrJ, 2014, 1(4):213-220.

Kahrilas, P., When Proton Pump Inhibitors Fail, Clinical Gastroenterology and Hepatology, 2008, 6(5):482-483.

Kamani, T. et al., The Prevalence of Llaryngopharyngeal Reflux in the English Population, European Archives of Otorhinolaryngology, 2012, 269:2219-2225.

Kelly, E. et al., Chronic Pepsin Exposure Promotes Anchorage-Independent Growth and Migration of a Hypopharyngeal Squamous Cell Line, Otolaryngology Head and Neck Surgery, 2014, 150(4):618-624.

Kim, J. et al., Effects of Pepsin and Pepstatin on Reflux Tonsil Hypertrophy In Vitro, PLOS One, 2018, 13(11: e0207090, pp. 1-12.

Kim, S. et al., Increased Risk of Larynx Cancer in Patients with Gastroesophageal Reflux Disease from a National Sample Cohort, Clinical Otolaryngology, 2019, 44(4):534-540.

Klimara, M. et al., Correlation of Salivary and Nasal Lavage Pepsin with MII-pH Testing, Laryngoscope, 2020, 130(4):961-966.

Klimara, M. et al., Detection of Pepsin in Oral Secretions of Infants With and Without Laryngomalacia, Annals of Otology, Rhinology & Laryngology, 2020, 129(3):224-229.

Klimara, M. et al., Proximal Reflux: Biochemical Mediators, Markers, Therapeutic Targets, and Clinical Correlations, Annals of the New York Academy of Sciences, 2020, 1481(1):127-138.

Knight, J. et al., Sensitive Pepsin Immunoassay for Detection of Laryngopharyngeal Reflux, Laryngoscope, 2005, 115(8):1473-1478.

Koufman, J., The Otolaryngologic Manifestations of Gastroesophageal Reflux Disease (GERD):A Clinical Investigation of 225 Patients Using Ambulatory 24-hour pH Monitoring and an Experimental Investigation of the Role of Acid and Pepsin in the Development of Laryngeal Injury, Laryngoscope, 1991, 101:1-78.

Koufman, J. et al., Prevalence of Reflux in 113 Consecutive Patients with Laryngeal and Voice Disorders, Otolaryngology Head and Neck Surgery, 2000, 123(4):385-388.

Koufman, J. et al., Laryngopharyngeal Reflux: Position Statement of the Committee on Speech, Voice, and Swallowing Disorders of the American Academy of Otolaryngology-Head and Neck Surgery, Otolaryngology Head and Neck Surgery, 2002, 127(1):32-35.

Koufman, J., Laryngopharyngeal Reflux is Different from Classic Gastroesophageal Reflux Disease, Ear, Nose & Throat Journal, 2002, 81(Suppl 2):7-9.

Koufman, J., Low-Acid Diet for Recalcitrant Llaryngopharyngeal Reflux: Therapeutic Benefits and Their Implications, Annals of Otology, Rhinology & Laryngology, 2011, 120(5):281-287.

Lam, P. et al., Rabeprazole is Effective in Treating Laryngopharyngeal Reflux in a Randomized Placebo-Controlled Trial, Clinical Gastroenterology and Hepatology, 2010, 8(9):770-776.

Lea, W. et al., Fluorescence Polarization Assays in Small Molecule Screening, Expert Opinion on Drug Discovery, 2011, 6(1):17-32.

Lechien, J. et al., Development of Scores Assessing the Refluxogenic Potential of Diet of Patients with Laryngopharyngeal Reflux, European Archives of Oto-Rhino-Laryngology, 2019, 276:3389-3404.

Lechien, J. et al., Evaluation and Management of Laryngopharyngeal Reflux Disease: State of the Art Review, Otolaryngology Head and Neck Surgery, 2019, 160(5):762-782.

Lechien, J. et al., Laryngopharyngeal Reflux Disease in Singers: Pathophysiology, Clinical Findings and Perspectives of a New Patient-Reported Outcome Instrument, European Annals of Otorhinolaryngology, Head and Neck Diseases, 2019, 136(3):S39-S43.

Lechien, J. et al., Surgical Treatment for Laryngopharyngeal Reflux Disease: A Systematic Review, JAMA Otolaryngology Head & Neck Surgery, 2019, 145(7):655-666.

(56) References Cited

OTHER PUBLICATIONS

Lechien, J. et al., Is Empirical Treatment a Reasonable Strategy for Laryngopharyngeal Reflux? A Contemporary Review, Clinical Otolaryngology, 2020, 45(4):450-458.

Lechien, J. et al., Validity and Reliability of the Reflux Sign Assessment, Annals of Otology, Rhinology & Laryngology, 2020, 129(4):313-325.

Lechien, J. et al., Validity and Reliability of the Reflux Symptom Score, Laryngoscope, 2020, 130(3):E98-E107.

Li, H. et al., Critical Role of Neutrophil Alkaline Phosphatase in the Antimicrobial Function of Neutrophils, Life Sciences, 2016, 157:152-157.

Lien, H. et al., Composite pH Predicts Esomeprazole Response in Laryngopharyngeal Reflux Without Typical Reflux Syndrome, Laryngoscope, 2013, 123(6):1483-1489.

Lien, H. et al., Responder Definition of a Patient-Reported Outcome Instrument for Laryngopharyngeal Reflux Based on the US Fda Guidance, Value in Health, 2015, 18(4):396-403.

Lipan, M. et al., Anatomy of Reflux: A Growing Health Problem Affecting Structures of the Head and Neck, Anatomical Record (Part B: New Anatomist), 2006, 289(6):261-270.

Little, F. et al., Effect of Gastric Acid on the Pathogenesis of Subglottic Stenosis, Annals of Otology, Rhinology & Laryngology, 1985, 94(5):516-519.

Liu, C. et al., Meta-analysis of the Efficacy of Proton Pump Inhibitors for the Symptoms of Laryngopharyngeal Reflux, Brazilian Journal of Medical and Biological Research, 2016, 49(7):e5149, 5 pages.

Long, F. et al., AceDRG: A Stereochemical Description Generator for Ligands, Acta Crystallographica, 2017, D73:112-122.

Lowden, M. et al., Prevalence of Symptoms Suggestive of Extra-Oesophageal Reflux in a General Practice Population in the UK, Logopedics Phoniatrics Vocology, 2009, 34(1):32-35.

Luebke, K. et al., Pepsin as a Biomarker for Llaryngopharyngeal Reflux in Children with Laryngomalacia, Laryngoscope, 2017, 127(10):2413-2417.

Luft, J. et al., A Method to Produce Microseed Stock for Use in the Crystallization of Biological Macromolecules, Acta Crystallographica, 1999, D55:988-993.

Lungova, V. et al., Ontogeny of the Mouse Vocal Fold Epithelium, Developmental Biology, 2015, 399(2):263-282.

Lv, Z. et al., HIV Protease Inhibitors: A Review of Molecular Selectivity and Toxicity, HIV/AIDS-Research and Palliative Care, 2015, 7:95-104.

Ahn, JY et al., The effect of sequential therapy with lansoprazole and ecabet sodium in treating iatrogenic gastric ulcer after endoscopic submucosal dissection: a randomized prospective study. J Dig Dis. Feb. 2015;16(2):75-82.

Bonnevie, O. et al., Double-blind randomised clinical trial of a pepsin inhibitory pentapeptide (pepstatin) in the treatment of duodenal ulcer. Gut, 1979(20): 624-628.

Cocking, JB et al., A Trial of Amylopectin Sulfate (SN-263) and Propantheline Bromide in the Long Term Treatment of Chronic Duodenal Ulcer. Gastroenterol. 1972; 62(1):6-10.

Lee, HL et al., Efficacy and safety of ecabet sodium on functional dyspepsia: A prospective, double-blinded, randomized, multi-center controlled trial. World J Gastroenterol. 2006; 12(17): 2756-2761.

Svendsen, LB et al., Gastric ulcer therapy with a pepsin-inactivating peptide, pepstatin: a double-blind randomized clinical trial. Scand J Gastroenterol 1979;14:929-932.

Al-Hakeim, H. et al., High Ionic Strength Enhances the Anti-Pepsin Activity of Titanium Dioxide Nanoparticles, Nano Biomedicine and Engineering, 2016, 8(3):136-143.

Matsumura, T. et al., Clinical Utility of Salivary Pepsin Measurement in Patients with Proton Pump Inhibitor-Refractory Gastroesophageal Reflux Disease Symptoms: A Prospective Comparative Study, Esophagus, 2020, 17(3):339-347.

Sunderland, A. et al., Alginates Inhibit Pepsin Activity In Vitro; A Justification for Their Use in Gastro-Oesophageal Reflux Disease (GORD), Gastroenterology, 2000, 118(4):A21.

China National Intellectual Property Administration, Decision on Rejection, Application No. 202180036213.8, Jan. 14, 2026, 21 pages.

Bobin, F. et al., Saliva Pepsin Level of Laryngopharyngeal Reflux Patients Is Not Correlated With Reflux Episodes, Laryngoscope, 2020, 130:1278-1281.

Chen, J. et al., AGA Clinical Practice Update on the Diagnosis and Management of Extraesophageal Gastroesophageal Reflux Disease: Expert Review, Clinical Gastroenterology and Hepatology, 2023, 21:1414-1421.

Dy, F. et al., Salivary Pepsin Lacks Sensitivity as a Diagnostic Tool to Evaluate Extraesophageal Reflux Disease, Journal of Pediatrics, 2016, 177:53-58.

Guo, Z. et al., Salivary Peptest for Laryngopharyngeal Reflux and Gastroesophageal Reflux Disease, Medicine, 2021, 100:32(e26756), pp. 1-9.

Hayat, J. et al., Pepsin in Saliva for the Diagnosis of Gastro-Oesophageal Reflux Disease, Gut, 2015, 64:373-380.

Jin, X. et al., Meta-Analysis of Proton Pump Inhibitors in the Treatment of Pharyngeal Reflux Disease, Computational and Mathematical Methods in Medicine, 2022, vol. 2022, Article ID 9105814, 9 pages.

Katz, P. et al., ACG Clinical Guideline: Guidelines for the Diagnosis and Management of Gastroesophageal Reflux Disease, American Journal of Gastroenterology, 2022, 117(1):27-56.

Kim, G. et al., Potassium-Competitive Acid Blockers for Treatment of Extraesophageal Symptoms and Signs, Journal of Neurogastroenterology and Motility, 2025, 31(2):170-177.

Lechien, J. et al., Does Pepsin Saliva Concentration (Peptest(TM)) Predict the Therapeutic Response of Laryngopharyngeal Reflux Patients?, Annals of Otology, Rhinology & Laryngology, 2021, 130(9):996-1003.

Liu, C. et al., Meta-Analysis of the Efficacy of Proton Pump Inhibitors for the Symptoms of Laryngopharyngeal Reflux, Brazilian Journal of Medical and Biological Research, 2016, 49(7):e5149, pp. 1-5.

Vaezi, M. et al., Extraesophageal Symptoms and Diseases Attributed to GERD: Where is the Pendulum Swinging Now?, Clinical Gastroenterology and Hepatology, 2018, 16:1018-1029.

Yadlapati, R. et al., The San Diego Consensus for Laryngopharyngeal Symptoms and Laryngopharyngeal Reflux Disease, American Journal of Gastroenterology, 2025, 00:1-15.

Zhang, M. et al., Clinical Relevance of Salivary Pepsin Detection in Diagnosing Gastroesophageal Reflux Disease Subtypes, Gastroenterology Report, 2023, 11(0):goad053, pp. 1-8.

Adams, P. et al., PHENIX: A Comprehensive Python-Based System for Macromolecular Structure Solution, Acta Crystallographica, 2010, D66:213-221.

Adhami, T. et al., The Role of Gastric and Duodenal Agents in Laryngeal Injury: An Experimental Canine Model, American Journal of Gastroenterology, 2004, 99(11):2098-2106.

Afonine, P. et al., Joint X-ray and Neutron Refinement with phenix. Refine, Acta Crystallographica, 2010, D66:1153-1163.

Agrawal, A. et al., Symptoms with Acid and Nonacid Reflux may be Produced by Different Mechanisms, Diseases of the Esophagus, 2009, 22(5):467-470.

Ali, M. et al., Bile Acids in Laryngopharyngeal Refluxate: Will They Enhance or Attenuate the Action of Pepsin?, Laryngoscope, 2013, 123(2):434-439.

Altman, K. et al., Changing Impact of Gastroesophageal Reflux in Medical and Otolaryngology Practice, Laryngoscope, 2005, 115(7):1145-1153.

Amin, S. et al., Laryngopharyngeal Reflux with Sore Throat: An Ultrastructural Study of Oropharyngeal Epithelium, Annals of Otology, Rhinology & Laryngology, 2009, 118(5):362-367.

Andrews, T. et al., Histologic Versus pH Probe Results in Pediatric Laryngopharyngeal Reflux, International Journal of Pediatric Otorhinolaryngology, 2013, 77(5):813-816.

Axford, S. et al., Cell Biology of Laryngeal Epithelial Defenses in Health and Disease: Preliminary Studies, Annals of Otology, Rhinology & Laryngology, 2001, 110(12):1099-1108.

(56)          References Cited

OTHER PUBLICATIONS

Bardhan, K. et al., Reflux Revisited: Advancing the Role of Pepsin, International Journal of Otolaryngology, 2012, vol. 2012, Article ID 646901, 13 pages.

Barry, D. et al., Laryngopharyngeal Reflux: More Questions than Answers, Cleveland Clinic Journal of Medicine, 2010, 77(5):327-334.

Battye, T. et al., iMOSFLM: A New Graphical Interface for Diffraction-Image Processing with MOSFLM, Acta Crystallagraphica, 2011, D67:271-281.

Belafsky, P. et al., The Validity and Reliability of the Reflux Finding Score (RFS), Laryngoscope, 2001, 111(8):1313-1317.

Belafsky, P. et al., Validity and Reliability of the Reflux Symptom Index (RSI), Journal of Voice, 2002, 16(2):274-277.

Belafsky, P., PRO: Empiric Treatment with PPIs is not Appropriate Without Testing, American Journal of Gastroenterology, 2006, 101:6-11.

Bianchi, E. et al., Impact of Fundoplication for Gastroesophageal Reflux in the Outcome of Benign Tracheal Stenosis, Journal of Thoracic and Cardiovascular Surgery, 2019, 158(6):1698-1706.

Blondeau, K. et al., Gastro-Oesophageal Reflux and Gastric Aspiration in Lung Transplant Patients with or without Chronic Rejection, European Respiratory Journal, 2008, 31(4):707-713.

Bourne, G., Alkaline Phosphatase in Taste Buds and Nasal Mucosa, Nature, 1948, 161(4090):445-446.

Caicedo-Granados, E. et al., N-methylnitrosourea-induced Carcinoma as a Model for Laryngeal Carcinogenesis, Head & Neck, 2014, 36(12):1802-1806.

Calvo-Henriquez, C. et al., Is Pepsin a Reliable Marker of Laryngopharyngeal Reflux? A Systematic Review, Otolaryngology Head and Neck Surgery, 2017, 157(3):385-391.

Campagnolo, A. et al., Laryngopharyngeal Reflux: Diagnosis, Treatment, and Latest Research, International Archives of Otorhinolaryngology, 2014, 18(2):184-191.

Chen, V. et al., MolProbity: All-Atom Structure Validation for Macromolecular Crystallography, Acta Crystallographica, 2010, D66:12-21.

Chen, L. et al., Survival and Prognostic Analysis of Preoperative Inflammatory Markers in Patients Undergoing Surgical Resection for Laryngeal Squamous Cell Carcinoma, BMC Cancer, 2018, 18:816, pp. 1-9.

Crapko, M. et al., Role of Extra-Esophageal Reflux in Chronic Otitis Media with Effusion, Laryngoscope, 2007, 117(8):1419-1423.

Dasgupta, A. et al., Rapid In Vitro Conversion of Fosphenytoin into Phenytoin in Sera of Patients with Liver Disease: Role of Alkaline Phosphatase, Journal of Clinical Laboratory Analysis, 2001, 15(5):244-250.

De Corso, E. et al., Impact of Bile Acids on the Severity of Laryngo-Pharyngeal Reflux, Clinical Otolaryngology, 2021, 46(1):189-195.

D'Ovidio, F. et al., Bile Acid Aspiration and the Development of Bronchiolitis Obliterans after Lung Transplantation, Journal of Thoracic and Ccardiovascular Surgery, 2005, 129(5):1144-1152.

Durkes, A. et al., In Vivo Investigation of Acidified Pepsin Exposure to Porcine Vocal Fold Epithelia, Laryngoscope, 2016, 126(1):E12-E17.

Eherer, A. et al., Effect of Pantoprazole on the Course of Reflux-Associated Laryngitis: A Placebo-Controlled Double-Blind Cross-over Study, Scandinavian Journal of Gastroenterology, 2003, 38(5):462-467.

El-Serag, H. et al., Lansoprazole Treatment of Patients with Chronic Idiopathic Laryngitis: A Placebo-Controlled Trial, Journal of the American College of Gastroenterology, 2001, 96(4):979-983.

Emsley, P. et al., Coot: Model-Building Tools for Molecular Graphics, Acta Crystallographica, 2004, D60:2126-2132.

Emsley, P. et al., Features and Development of Coot, Acta Crystallographica, 2010, D66:486-501.

Erickson, E. et al., Simulated Reflux Decreases Vocal Fold Epithelial Barrier Resistance, Laryngoscope, 2010, 120(8):1569-1575.

Esposito, C. et al., Laparoscopic Nissen Fundoplication: An Excellent Treatment of GERD-Related Respiratory Symptoms in Children—Results of a Multicentric Study, Journal of Laparoendoscopic & Advanced Surgical Techniques, 2018, 28(8):1023-1028.

Eto, T. et al., Further Studies on the Inhibition of Pepsin by Bile Salts, Annals of Surgery, 1986, 203(1):8-12.

Falk, G. et al., Fundoplication for Laryngopharyngeal Reflux Despite Preoperative Dysphagia, Annals of The Royal College of Surgeons of England, 2017, 99(3):224-227.

Figueiredo, A. et al., Laryngeal Mucosa Alterations in Mice Model of Gastroesophageal Reflux: Effects of Topical Protection, Laryngoscope, 2020, 130(12):E889-E895.

Ford, C., Evaluation and Management of Laryngopharyngeal Reflux, JAMA, 2005, 294(12):1534-1540.

Francis, D. et al., High Economic Burden of Caring for Patients with Suspected Extraesophageal Reflux, American Journal of Gastroenterology, 2013, 108(6):905-911.

Fujinaga, M. et al., Crystal Structure of Human Pepsin and its Complex with Pepstatin, Protein Science, 1995, 4(5):960-972.

Furfine, E. et al., Preclinical Pharmacology and Pharmacokinetics of GW433908, a Water-Soluble Prodrug of the Human Immunodeficiency Virus Protease Inhibitor Amprenavir, Antimicrobial Agents and Chemotherapy, 2004, 48 (3):791-798.

Gabriel, C. et al., The Importance of Chronic Laryngitis, Journal of Laryngology and Otology, 1960, 74(6):349-357.

Garg, D. et al., Follicular Bronchiolitis: Two Cases with Varying Clinical and Radiological Presentation, Case Reports in Pulmonology, 2020, vol. 2020, Article ID 4564587, 5 pages.

Gaynor, E., Gastroesophageal Reflux as an Etiologic Factor in Laryngeal Complications of Intubation, Laryngoscope, 1988, 98(9):972-979.

Gelardi, M. et al., Focus on Gastroesophageal Reflux (GER) and Laryngopharyngeal Reflux (LPR): New Pragmatic Insights in Clinical Practice, Journal of Biological Regulations & Homeostatic Agents, 2018, 32(1)(S2):1-8.

Giacchi, R. et al., Compliance with Anti-Reflux Therapy in Patients with Otolaryngologic Manifestations of Gastroesophageal Reflux Disease, Laryngoscope, 2000, 110(1):19-22.

Gill, G. et al., Laryngeal Epithelial Defenses Against Laryngopharyngeal Reflux: Investigations of E-cadherin, Carbonic Anhydrase Isoenzyme III, and Pepsin, Annals of Otology, Rhinology & Laryngology, 2005, 114(12):913-921.

Hammond, K. et al., Alkaline Phosphatase and Phosphoamino Acid Phosphatases in Normal and Cancerous Tissues of the Human Larynx, Biochemical Medicine and Metabolic Biology, 1990, 43(1):75-79.

Hopwood, D. et al., Effects of Bile Acids and Hydrogen Ion on the Fine Structure of Oesophageal Epithelium, Gut, 1981, 22(4):306-311.

Hurley, B. et al., Pepsin Triggers Neutrophil Migration Across Acid Damaged Lung Epithelium, Scientific Reports, 2019, 9(1):13778, 15 pages.

* cited by examiner

Average Total Mass deposition (5 minutes exposure)

Fig. 12 (continued)

Average Total Mass deposition (2 minutes exposure)

Legend: Larynx, Trachea

Particle Mass Distribution for 10 minutes exposure

Fig. 14 (continued)

Particle Mass Distribution for 5 minutes exposure

Legend: Day-2, Day-3, Day-4, Day-5, Day-6, Day-7, Day-8, Day-9, Day-10

X-axis: Particle Diameter [μm]

Y-axis: Particle Mass concentration [dm/ddp] [μg L$^{-1}$ μm$^{-1}$]

AEROSOLIZED FORMULATIONS OF HIV PROTEASE INHIBITORS FOR THE TREATMENT OF AIRWAY REFLUX

CROSS-REFERENCE TO RELATED APPLICATIONS

This is a continuation-in-part of PCT Application No. US2021/027758 filed on Apr. 16, 2021 which claims priority to U.S. Provisional Application No. 63/011,039, filed on Apr. 16, 2020, the contents of which are incorporated by reference in its entirety.

STATEMENT REGARDING FEDERALLY SPONSORED RESEARCH

N/A

REFERENCE TO AN ELECTRONIC SEQUENCE LISTING

The contents of the electronic sequence listing (650053.00831.xml; Size: 2,125 bytes; and Date of Creation: Oct. 10, 2022) is herein incorporated by reference in its entirety.

INTRODUCTION

Laryngopharyngeal reflux (LPR), the backflow of gastric contents into the laryngopharynx, is an important health problem. LPR affects children and adults equally, and the clinical spectrum of this disease is extensive (1-3). Unlike patients with gastroesophageal reflux disease (GERD), which is limited to the esophagus and causes heartburn, LPR patients have symptoms due to chronic laryngeal irritation and inflammation, such as chronic cough, throat clearing, post nasal drip, hoarseness or dysphonia, globus sensation, dysphagia, and dyspnea (1-3). Further, there is significant evidence that chronic LPR contributes to life-threatening illness such as laryngeal cancer (4-11). It is estimated that LPR affects more than 20% of the United States population and is present in up to 10% of patients presenting to an otolaryngologist's office (12-14). The economic burden of LPR is over 52 billion dollars per year, which is 5.6 times more than the cost of GERD, and 52% of that cost is attributed to the use of proton pump inhibitors (PPIs) (15-16).

While PPI therapy is a mainstay in the treatment of GER disease (GERD), its efficacy for the treatment of LPR is poor (18, 57). In clinical practice, it was previously believed that patients with LPR simply require higher doses and longer trials of PPIs than those with GERD. This belief was based on the assumption that the upper airway is more sensitive to acid reflux than the esophagus (1, 58, 59). However, placebo-controlled trials have failed to demonstrate any therapeutic benefit of PPIs for the treatment of LPR (60-65). Nonetheless, PPIs are still commonly prescribed for the treatment of LPR due to a lack of alternatives (23, 72). Given the potential risks of prolonged PPI therapy, its associated cost, and the high percentage of LPR patients for which PPI therapy has been shown ineffective, an alternative treatment for LPR is desperately needed (1, 18, 31, 57, 73, 74).

SUMMARY

The present disclosure provides methods of treating reflux in a subject in need thereof. In one aspect, the method comprising administering a therapeutically effective amount of an HIV protease inhibitor, alone or in conjunction with one or more additional therapeutic agents (e.g., a PPI), to a subject to treat the reflux. Suitably, the HIV protease inhibitor is capable of binding to and inhibiting the enzymatic activity of pepsin. In some aspects, the subject has an airway reflux, preferably wherein the airway reflux condition selected from laryngopharyngeal reflux (LPR), gastropharyngeal reflux (GPR), and esophagopharyngeal reflux (EPR). In another aspect, the subject has gastroesophageal reflux disease (GERD), preferably GERD that is refractory to proton pump inhibition.

In another aspect, the disclosure provides a composition comprising an aerosolized formulation of an HIV protease inhibitor capable of inhibiting pepsin and optionally, a pharmaceutically acceptable carrier. In some embodiments, the composition is administered in conjunction with one or more additional therapeutic agents (e.g., a PPI)

In a further aspect, the disclosure provides use of the composition described herein for the treatment of reflux in a subject in need thereof, wherein the subject has a condition selected from the group consisting of laryngopharyngeal reflux (LPR), gastropharyngeal reflux (GPR), esophagopharyngeal reflux (EPR), or GERD refractory to protein pump inhibition. In some embodiments, the subject is also administered a PPI (e.g., by standard therapeutic routes) as a combination therapy.

ratio and irregular, condensed chromatin is seen. (C, G) Thickened respiratory epithelium with pseudostratification of the epithelial cells. Keratinization (arrow) is present in multiple foci. Significant increase in the N:C ratio with loss of nuclear polarization and reduction in the apical cilia is evident in several regions of this treatment group. (D, H) Respiratory epithelium is necrotic (arrow) and replaced by an inflammatory exudate. A brisk, acute inflammatory infiltrate infiltrates the submucosal area.

Figure 6:
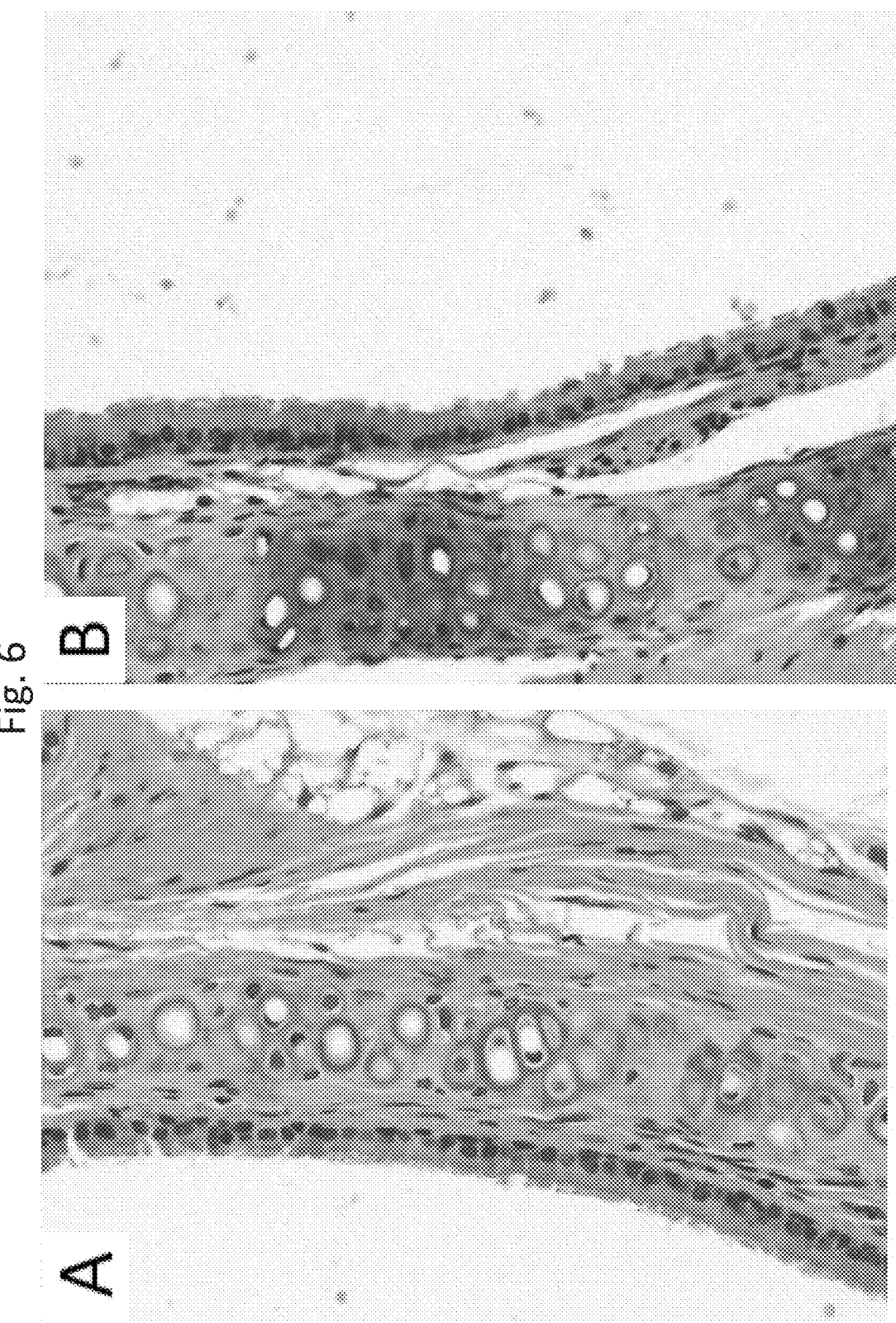
Figure 6:
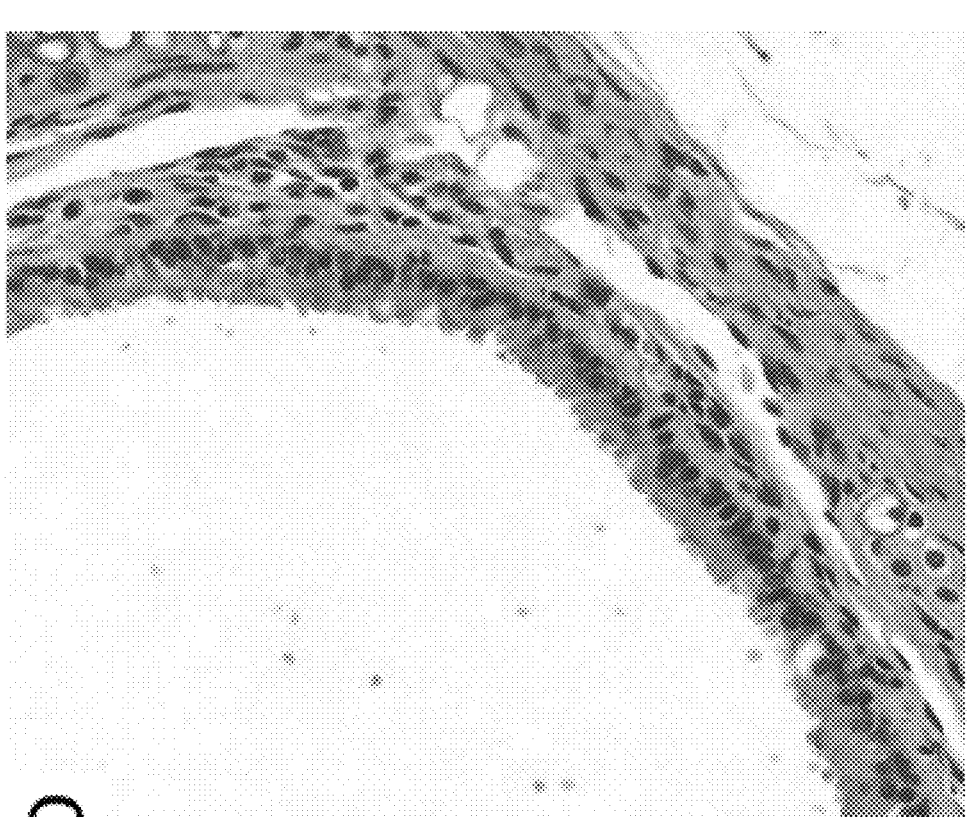
Figure 6:
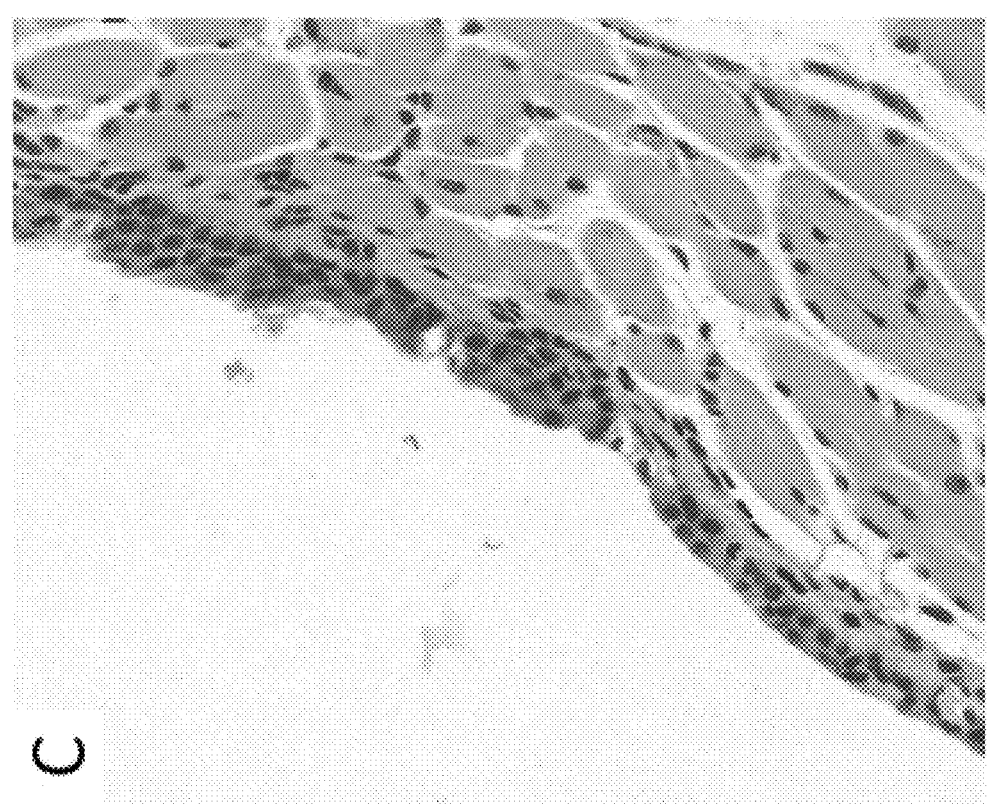

FIG. 6 depicts oral administration of Lexiva prevents pepsin-mediated airway epithelial damage in vivo. Representative animals from the different treatment protocols shown in each panel: pH 7 (panel A), Lexiva (panel B), 0.3 mg/ml pepsin at pH 7 (panel C), and 0.3 mg/ml pepsin pH 7+Lexiva (panel D). 20× magnification. (A, B, D) Normal-appearing respiratory epithelium consisting of a single layer of ciliated columnar epithelium with basal polarization of the nuclei and ciliated apical surfaces. (C) Reactive, multi-layered epithelium with increased nuclear to cytoplasmic (N:C) ratio and cilia loss.

Figure 7:
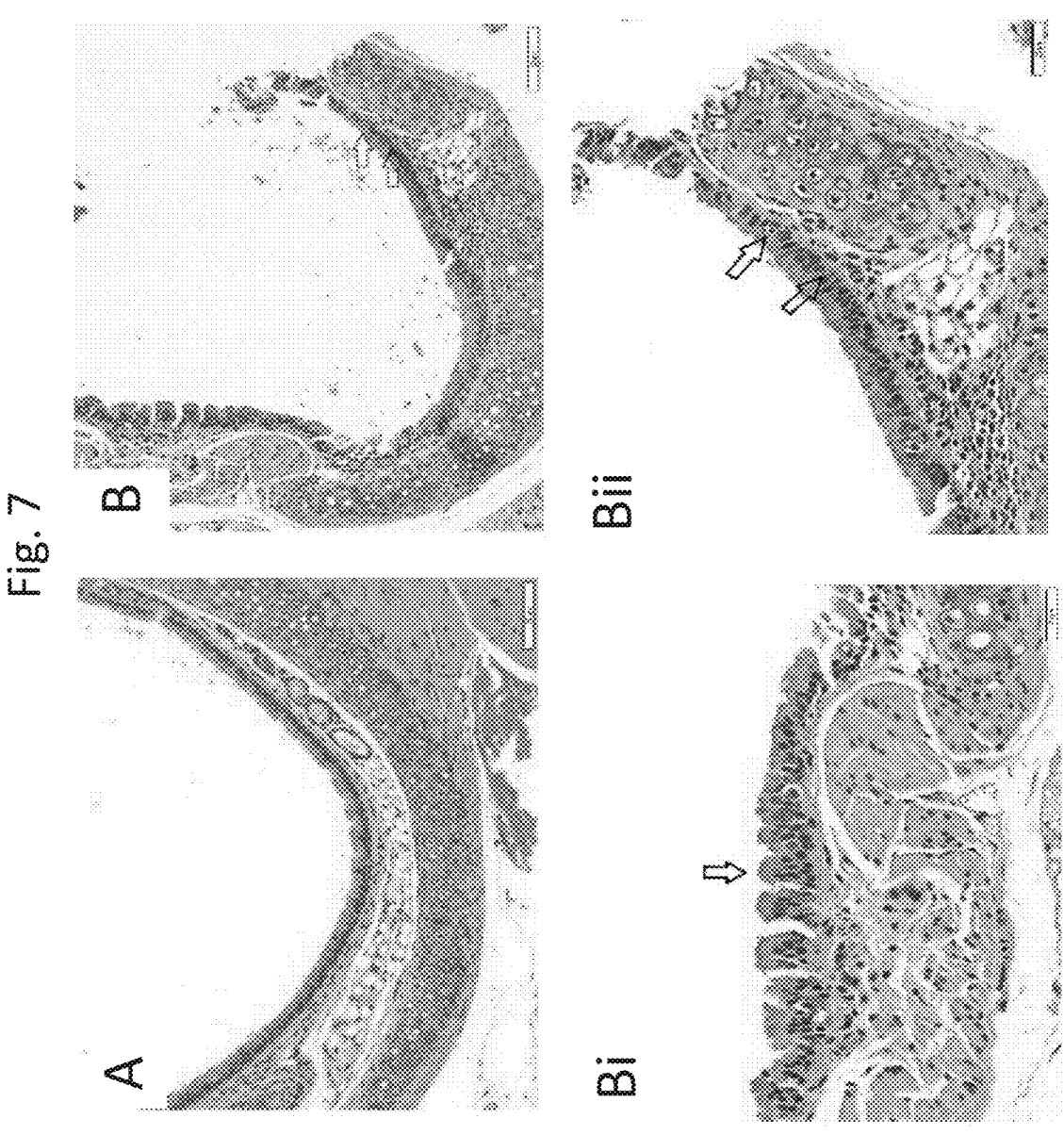

FIG. 7 depicts inhalation administration of fosamprenavir and darunavir prevent pepsin-mediated laryngeal injury. Representative animals from the different groups: A) Solvent control: single layer of respiratory epithelium with no reactive changes. B) Pepsin control: multi-layered epithelium and individual cell apoptosis (arrows): i) Higher magnification of multi-layered epithelium and ii) Higher magnification of cell apoptosis. C) Fosamprenavir gavage: normal histology in the solvent group. [This tissue section is more proximal than the others, almost at the oropharynx and thus some transitional-type epithelium can be seen]. D) Fosamprenavir gavage: normal histology in the pepsin group. E) Fosamprenavir aerosol: normal histology in the solvent group. F) Fosamprenavir aerosol: normal histology in the pepsin group. G) Darunavir gavage: mild reactive epithelia in the solvent group, but less than pepsin control. H) Darunavir gavage: mild reactive epithelia in the pepsin group but less than pepsin control. I) Darunavir aerosol: normal histology in the solvent group. J) Darunavir aerosol: normal histology in the pepsin group. A-J are 20× magnification with scale bar=50 µm Bi and Bii are 40× magnification with scale bar=20 µm.

Figure 8:
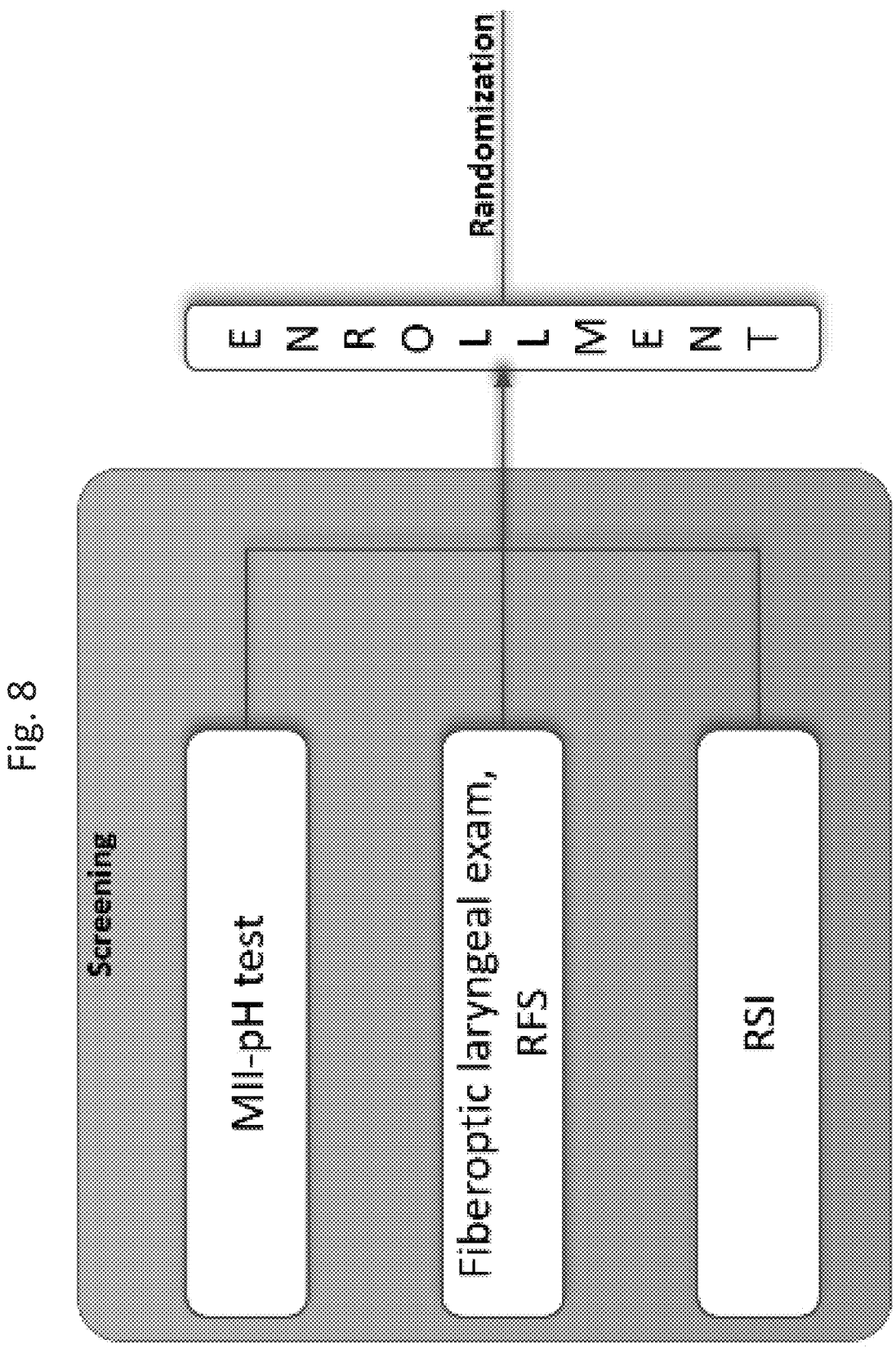
Figure 8:
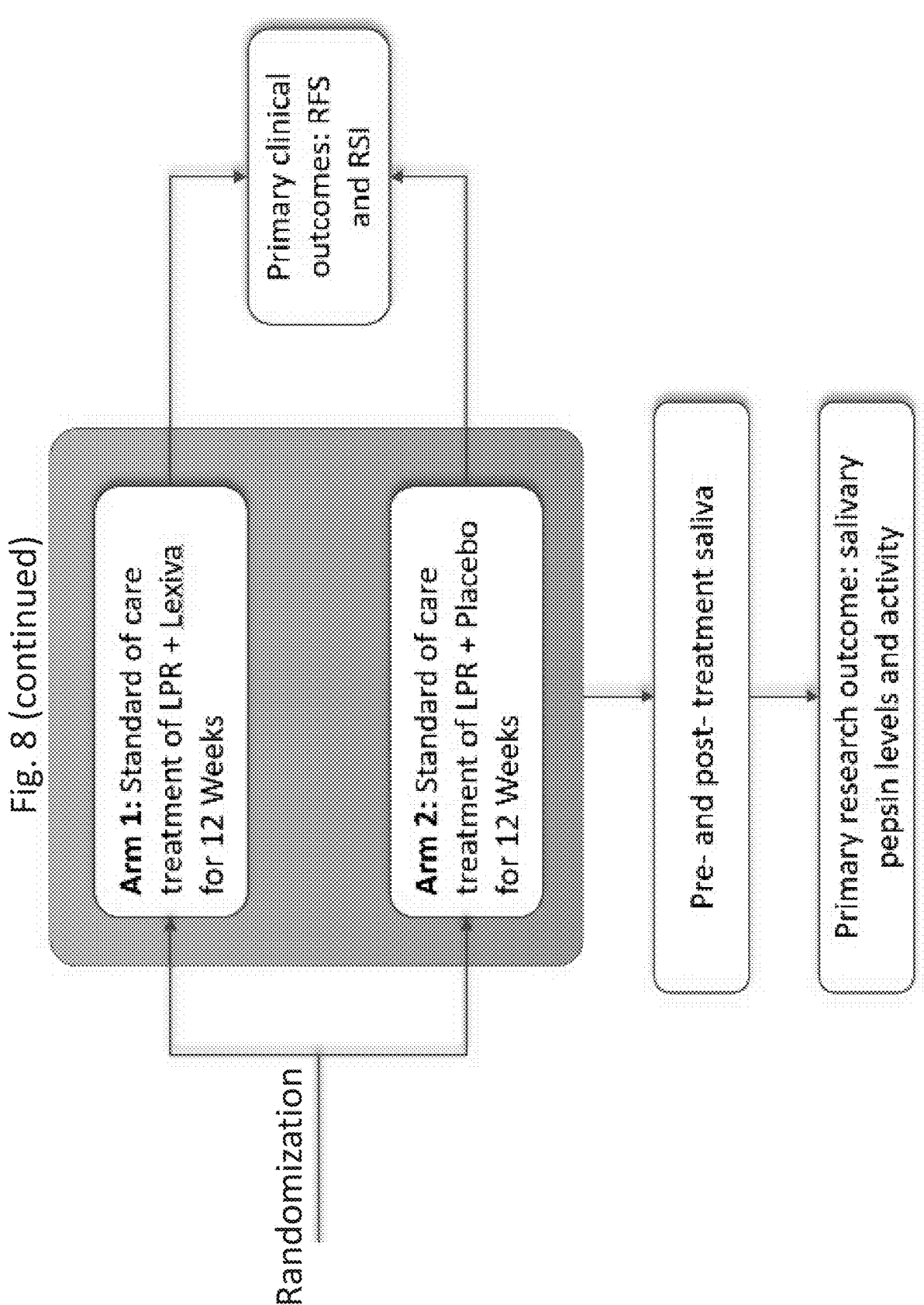

FIG. 8 is a schematic of a 12-week, randomized, double blind, placebo-controlled clinical trial designed to test the efficacy of the HIV protease inhibitor Lexiva for the treatment of LPR. While Lexiva is exemplified in this schematic, it is understood that other formulations of fosamprenavir may also be tested in a similar trial.

Figure 9:
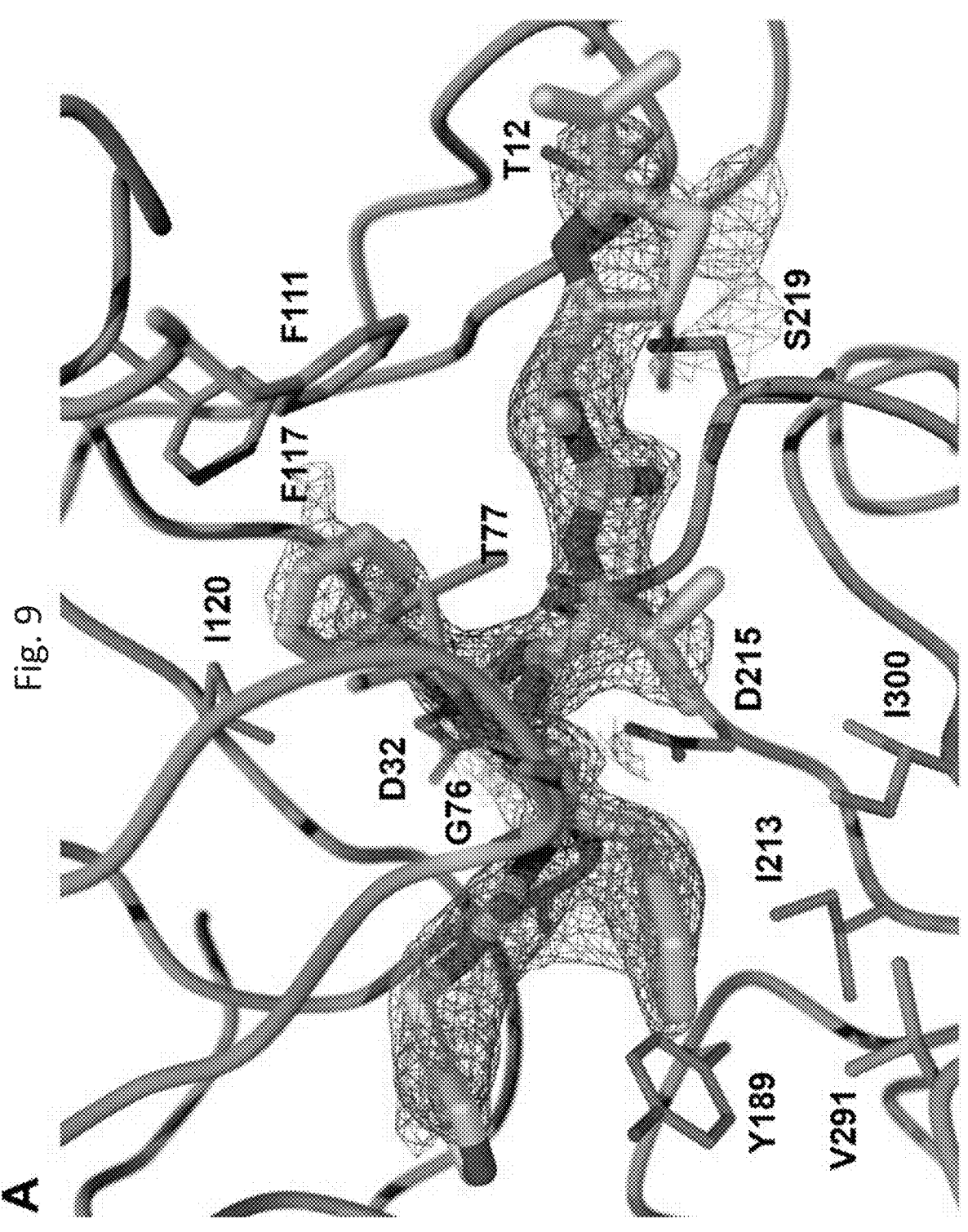
Figure 9:
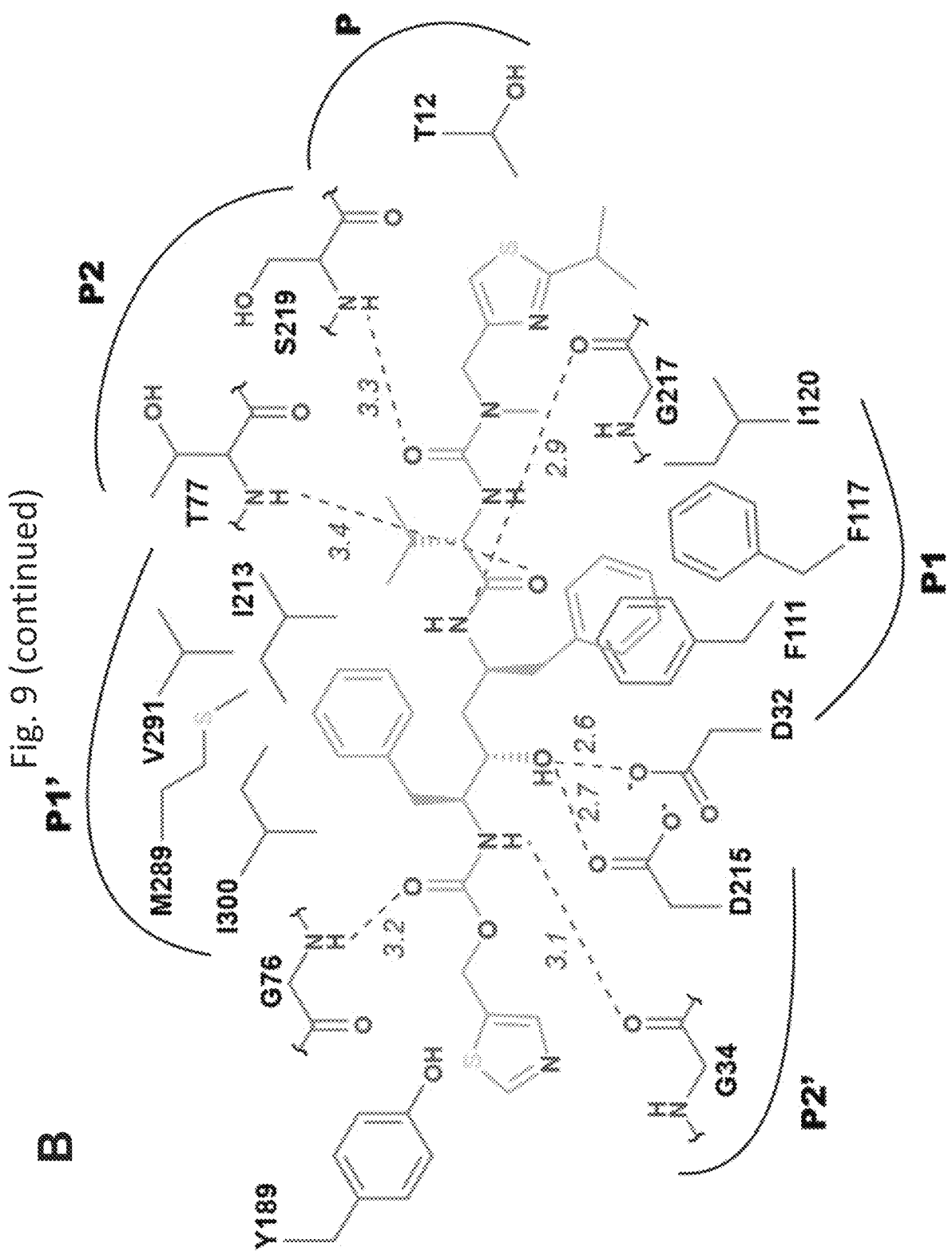

FIG. 9 shows the crystal structure of ritonavir bound to pepsin. (A) The active site of porcine pepsin with ritonavir bound. The $2F_o$-$F_c$ electron density map contoured at $1.0\sigma$ is shown as magenta mesh and the $2F_o$-$F_c$ simulated annealing composite omit map, also contoured at $1.0\sigma$, is shown as green mesh. (B) Schematic view of the active site with ritonavir bound showing potential hydrogen bonding interactions as green, dashed lines.

Figure 10:
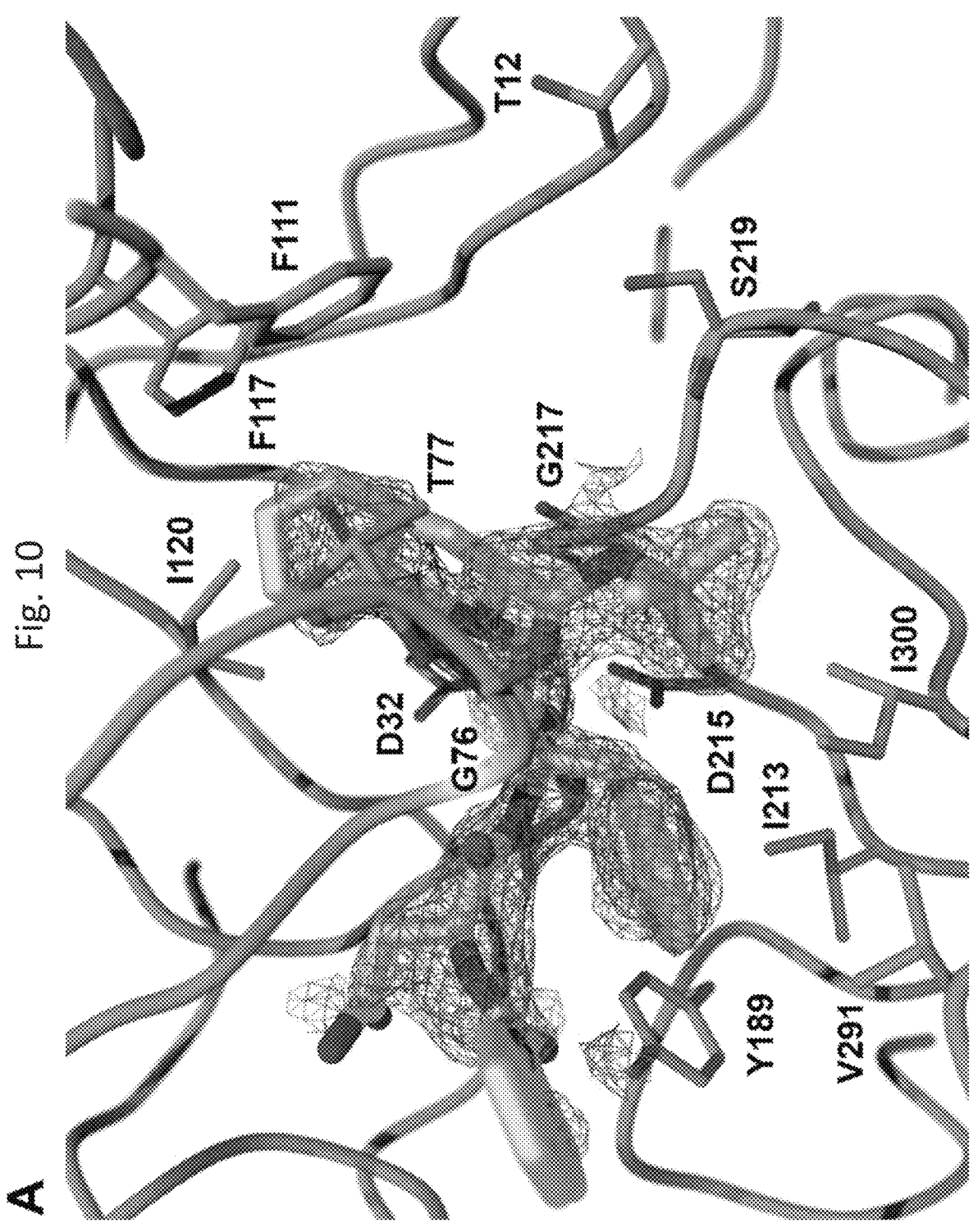
Figure 10:
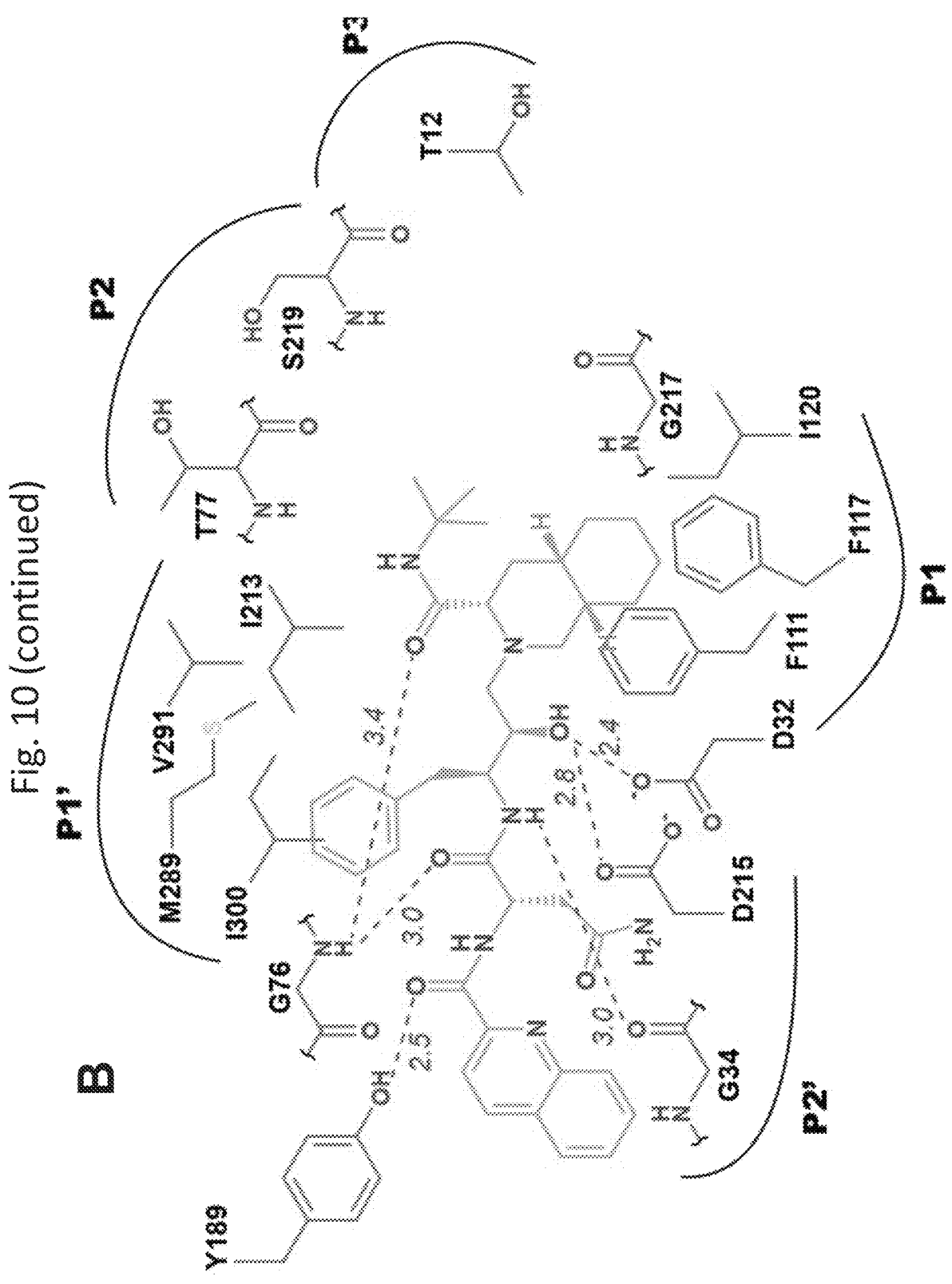

FIG. 10 shows the crystal structure of saquinavir bound to pepsin. (A) The active site of porcine pepsin with saquinavir bound. The $2F_o$-$F_c$ electron density map contoured at $1.0\sigma$ is shown as magenta mesh and the $2F_o$-$F_c$ simulated annealing composite omit map, also contoured at $1.0\sigma$, is shown as green mesh. (B) Schematic view of the active site with saquinavir bound showing potential hydrogen bonding interactions as green, dashed lines.

Figure 11:
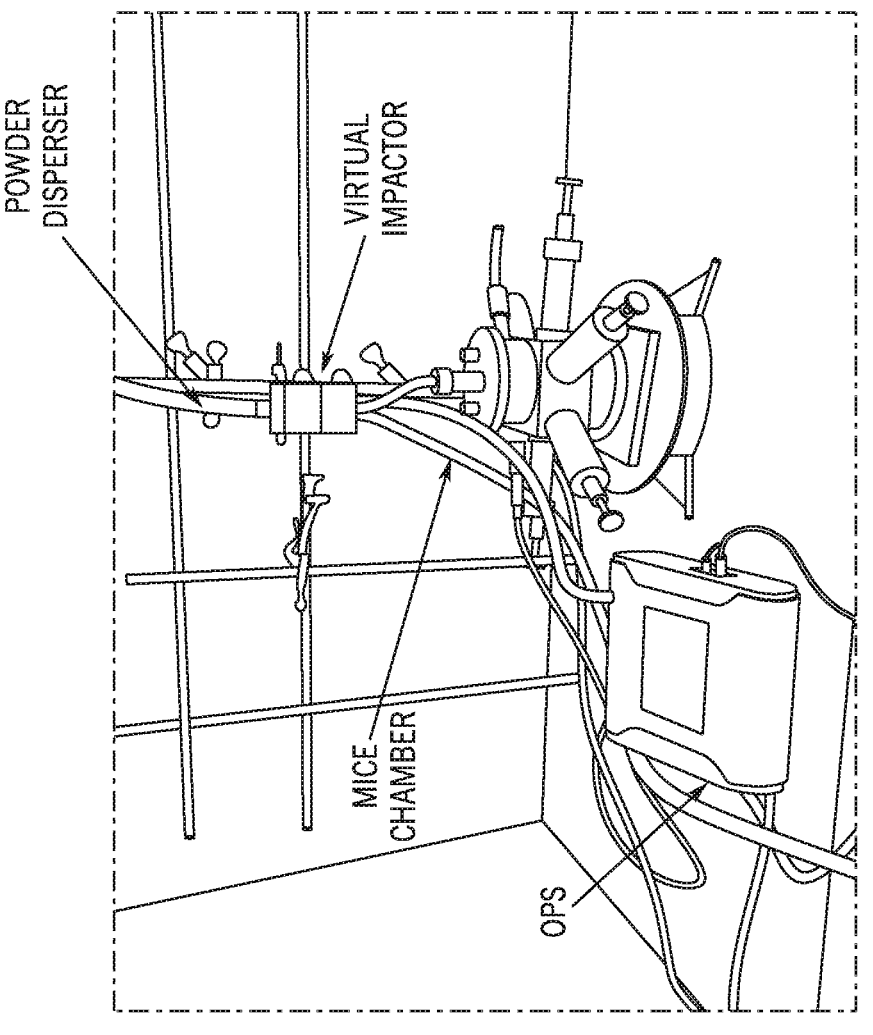

FIG. 11 shows an example experimental setup used to aerosolize fosamprenavir and measure particle size distribution.

Figure 12:
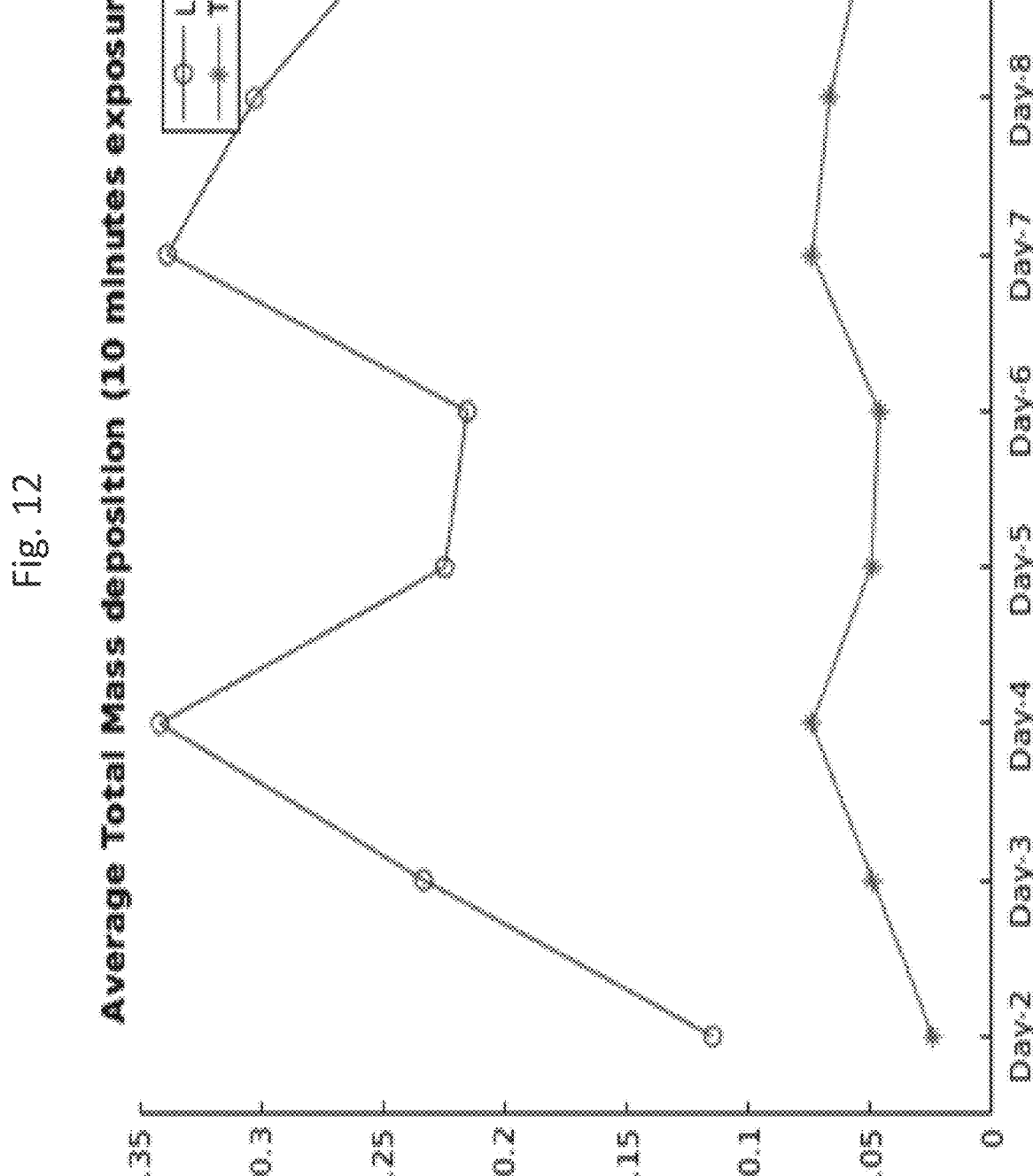
Figure 12:
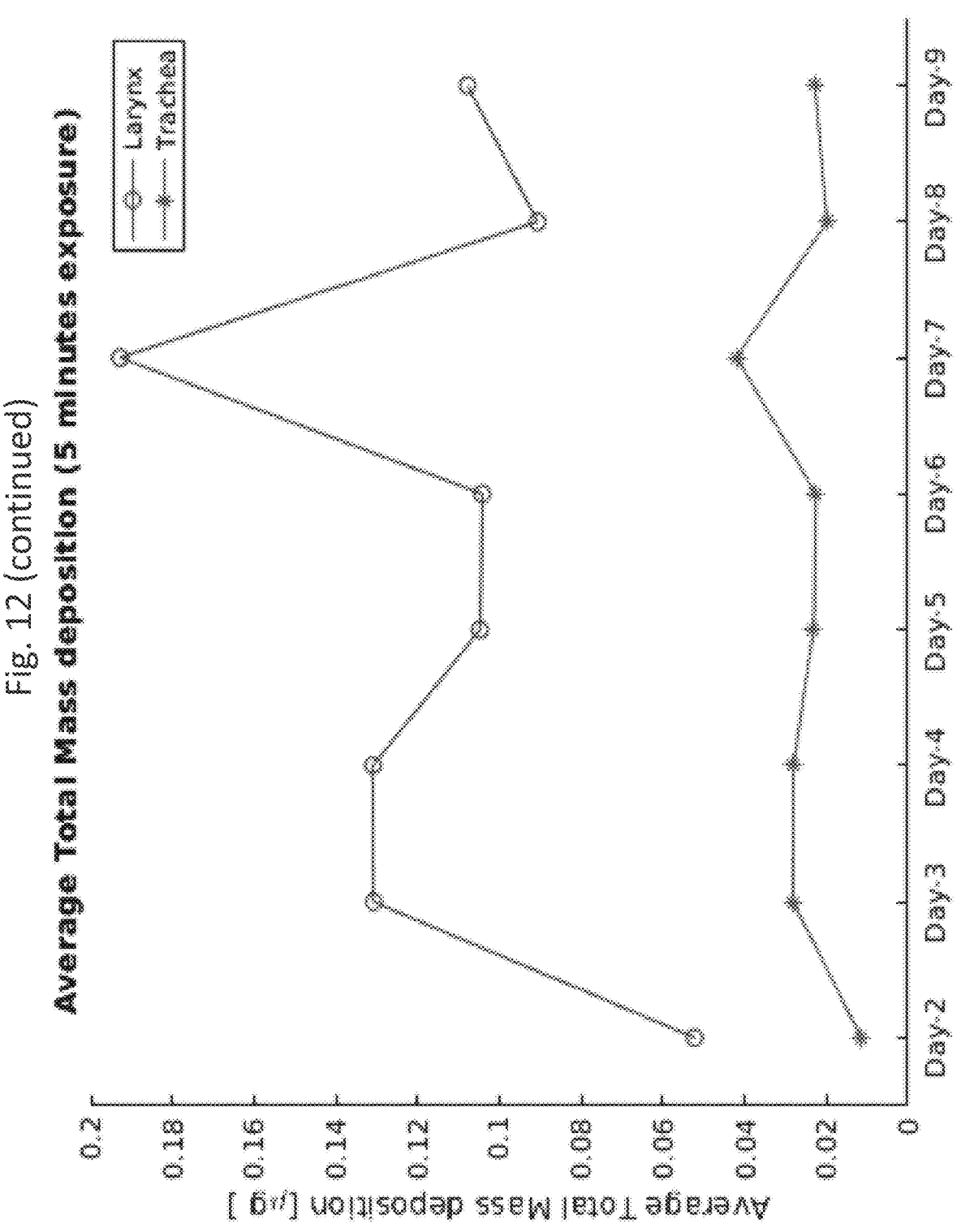

FIG. 12 shows plots of average total mass deposition fraction in the trachea and larynx measured over days following administration of aerosolized fosamprenavir at various exposure times.

Figure 13:
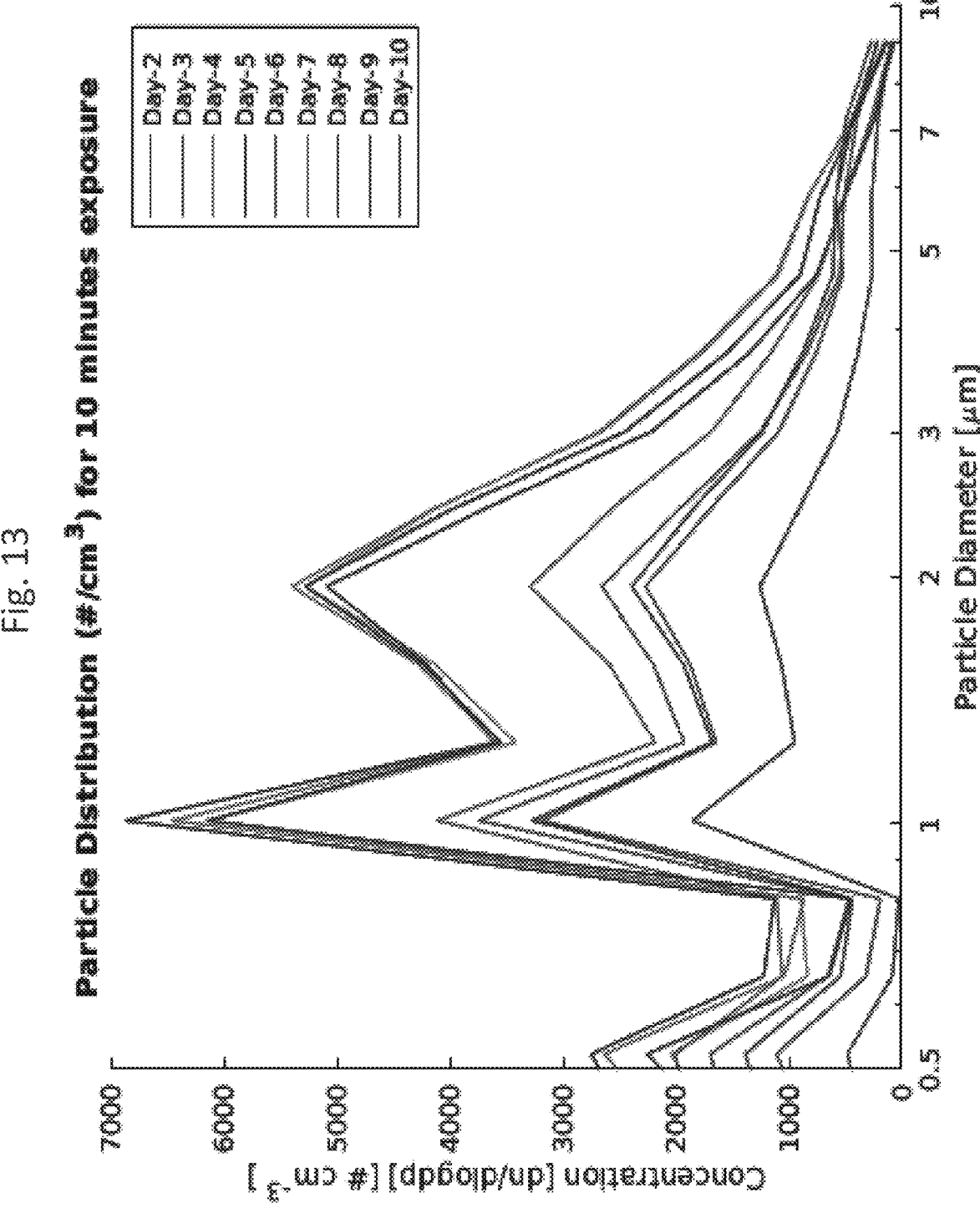
Figure 13:
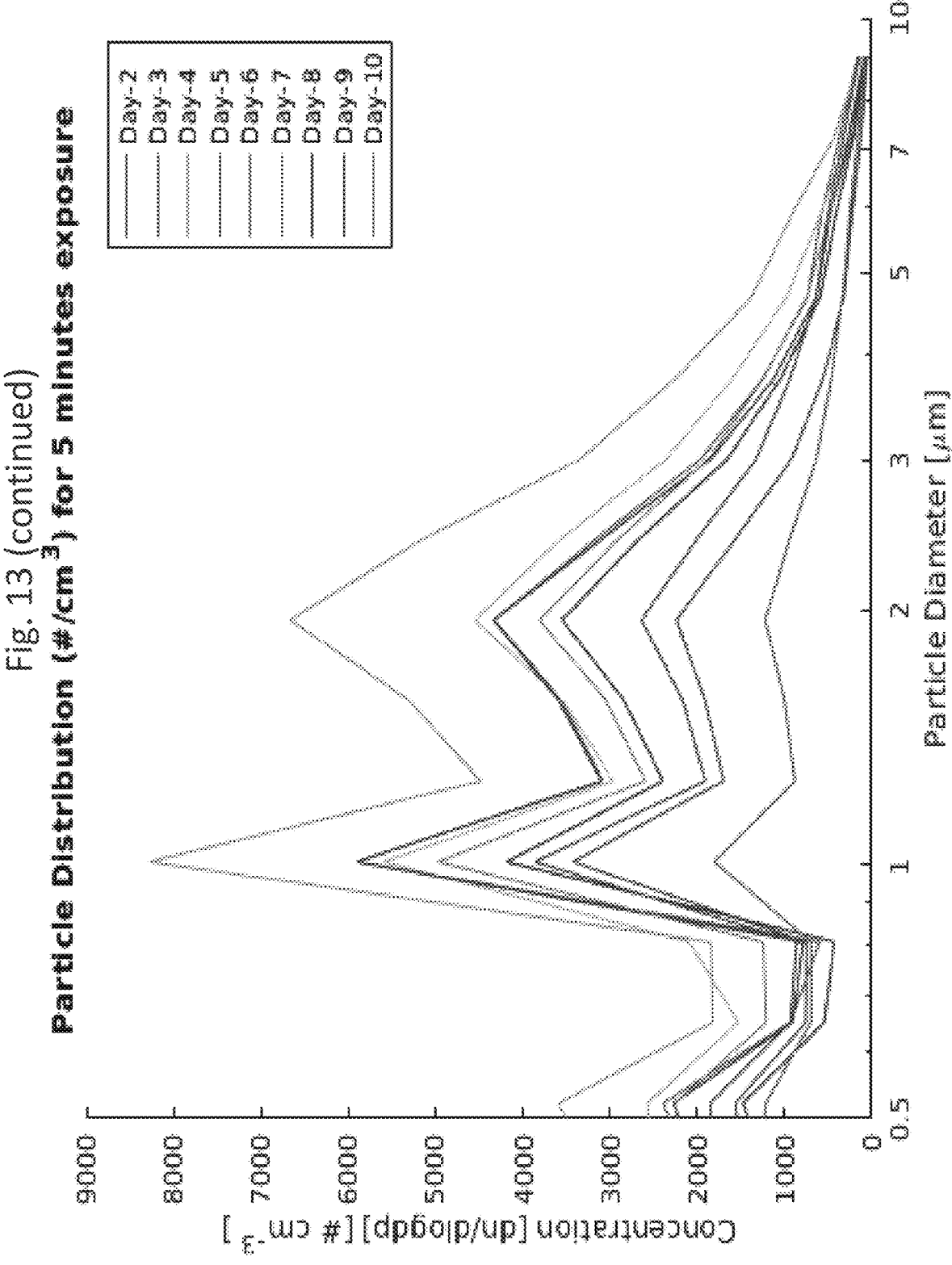
Figure 13:
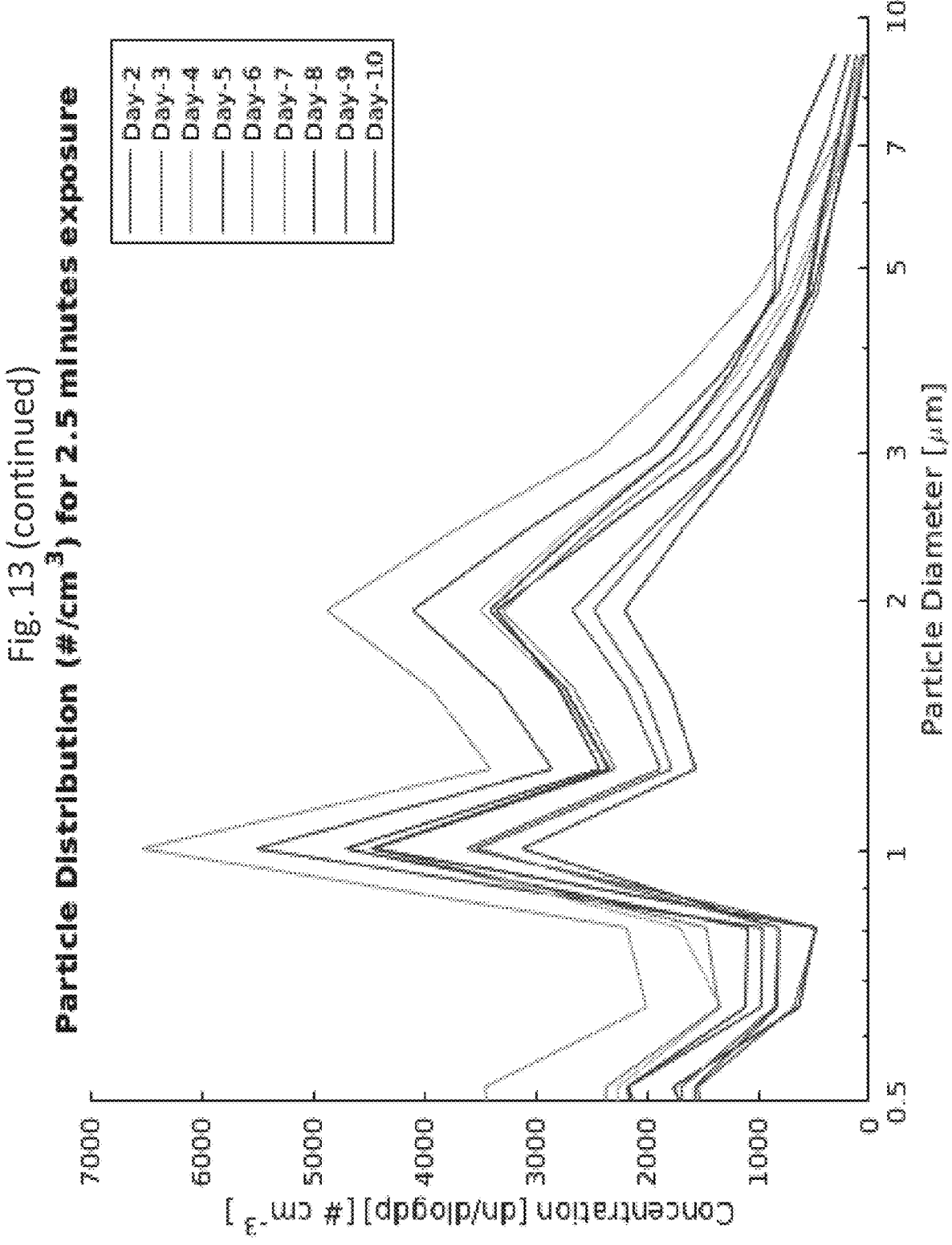

FIG. 13 shows plots of particle distribution measured over days following administration of aerosolized fosamprenavir at various exposure times.

Figure 14:
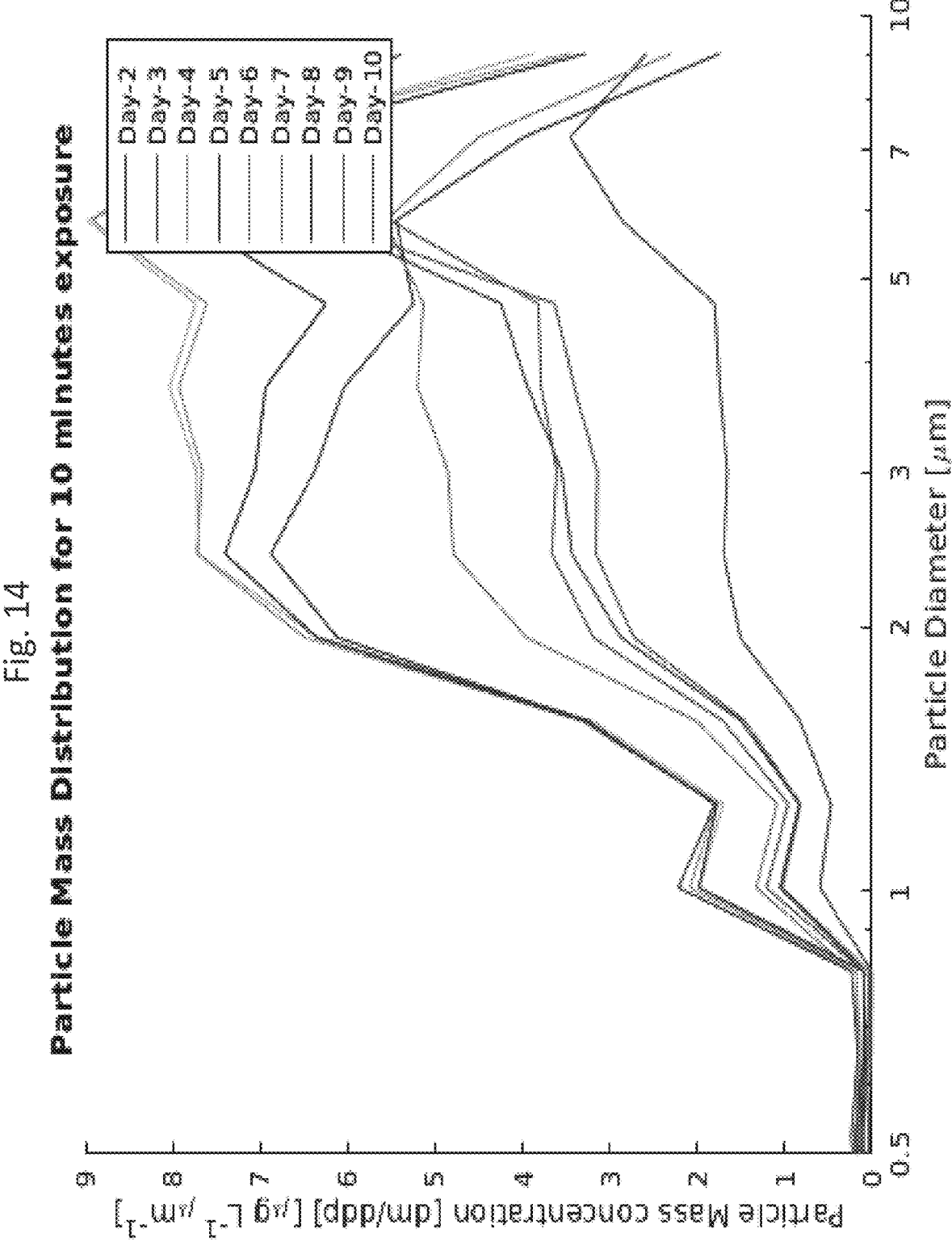
Figure 14:
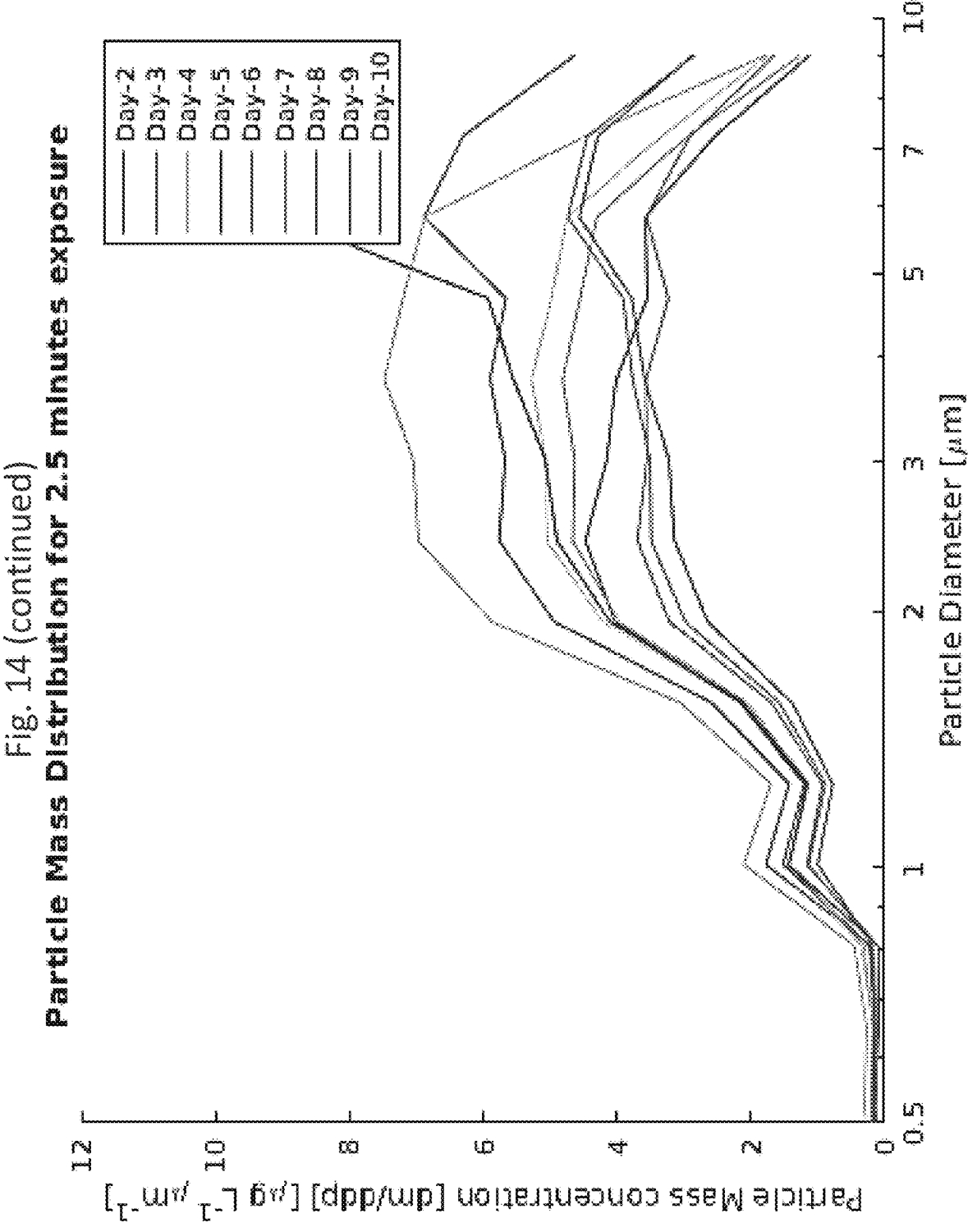

FIG. 14 shows plots of particle mass distribution measured over days following administration of aerosolized fosamprenavir at various exposure times.

Figure 15:
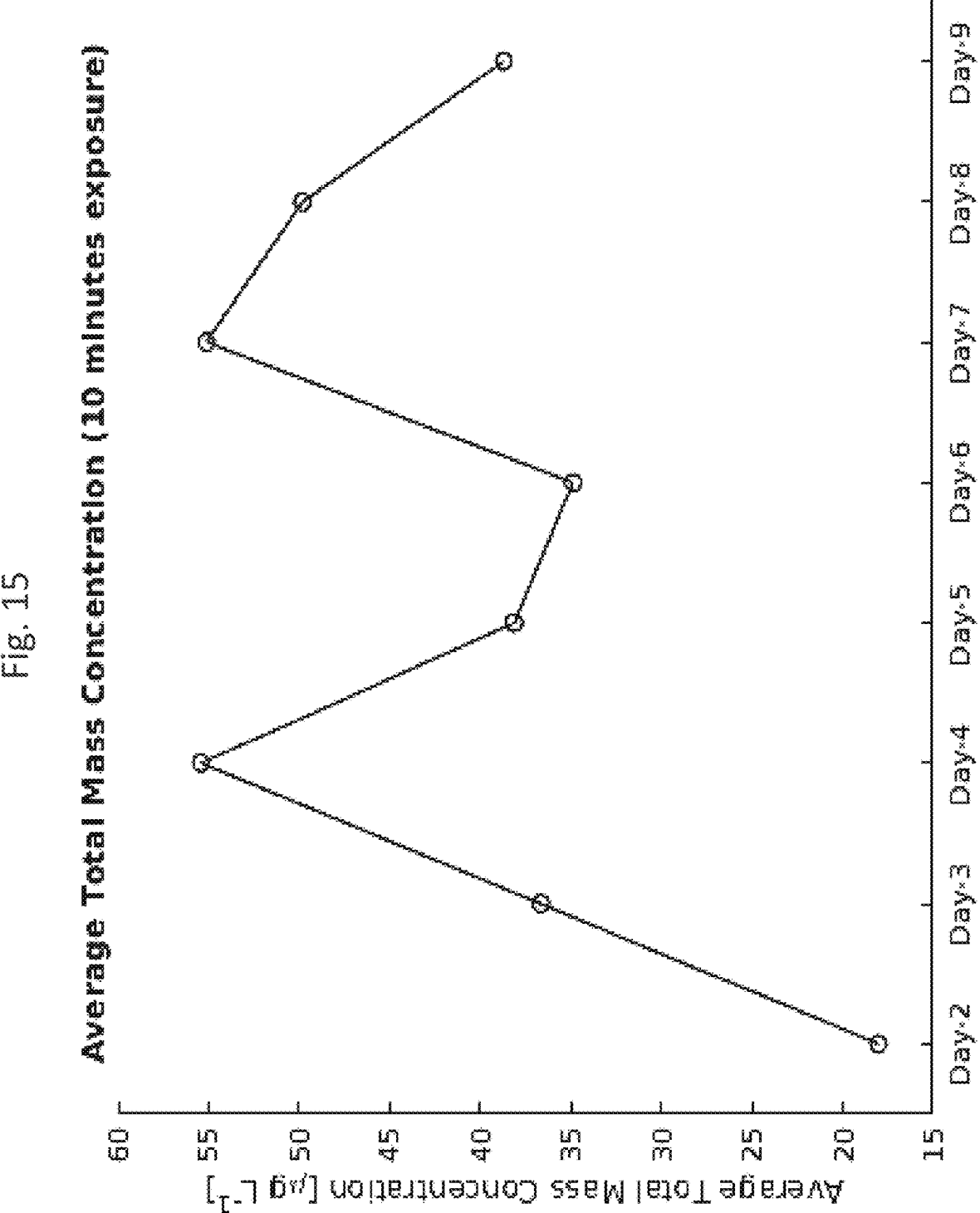
Figure 15:
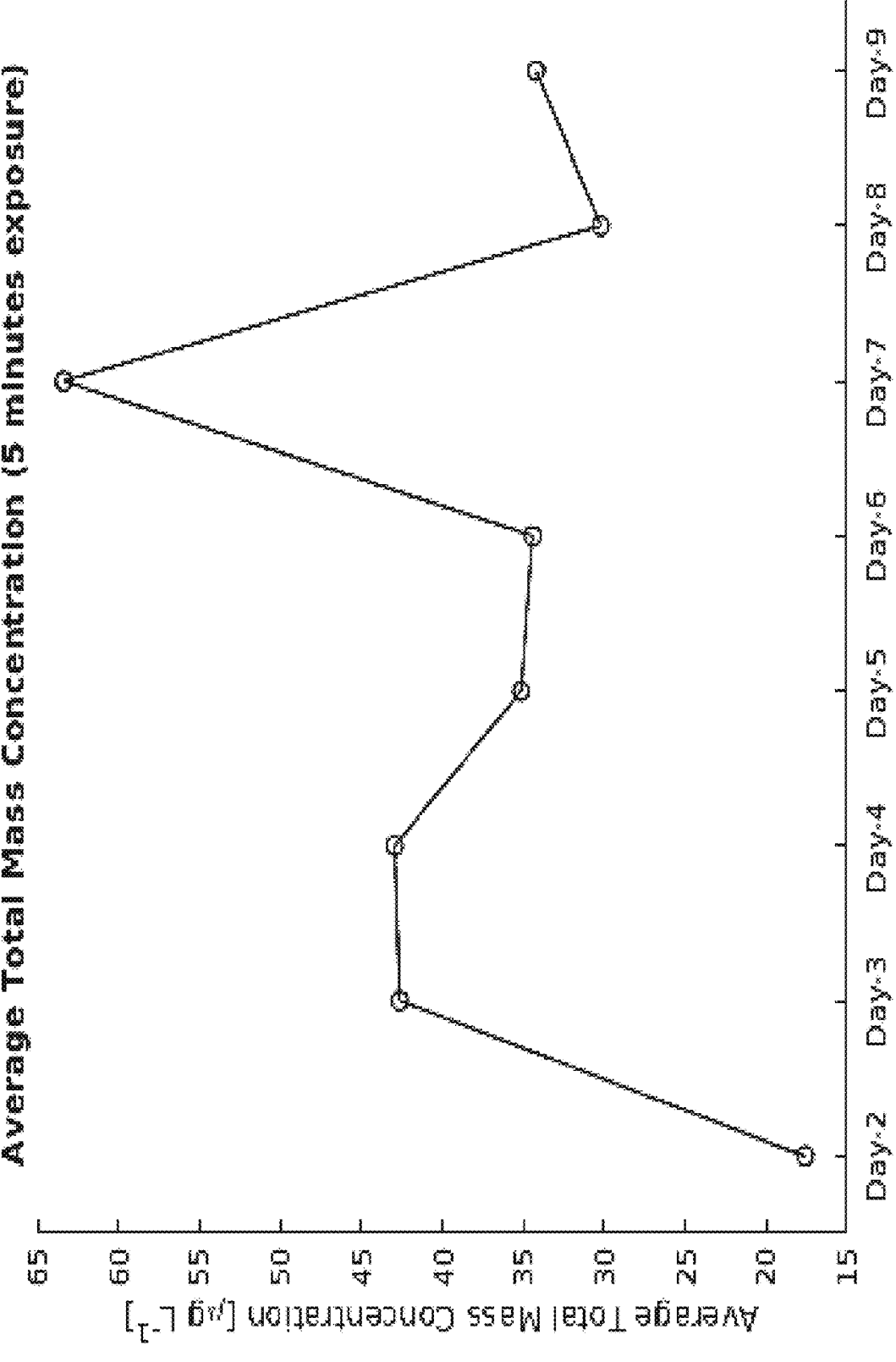
Figure 15:
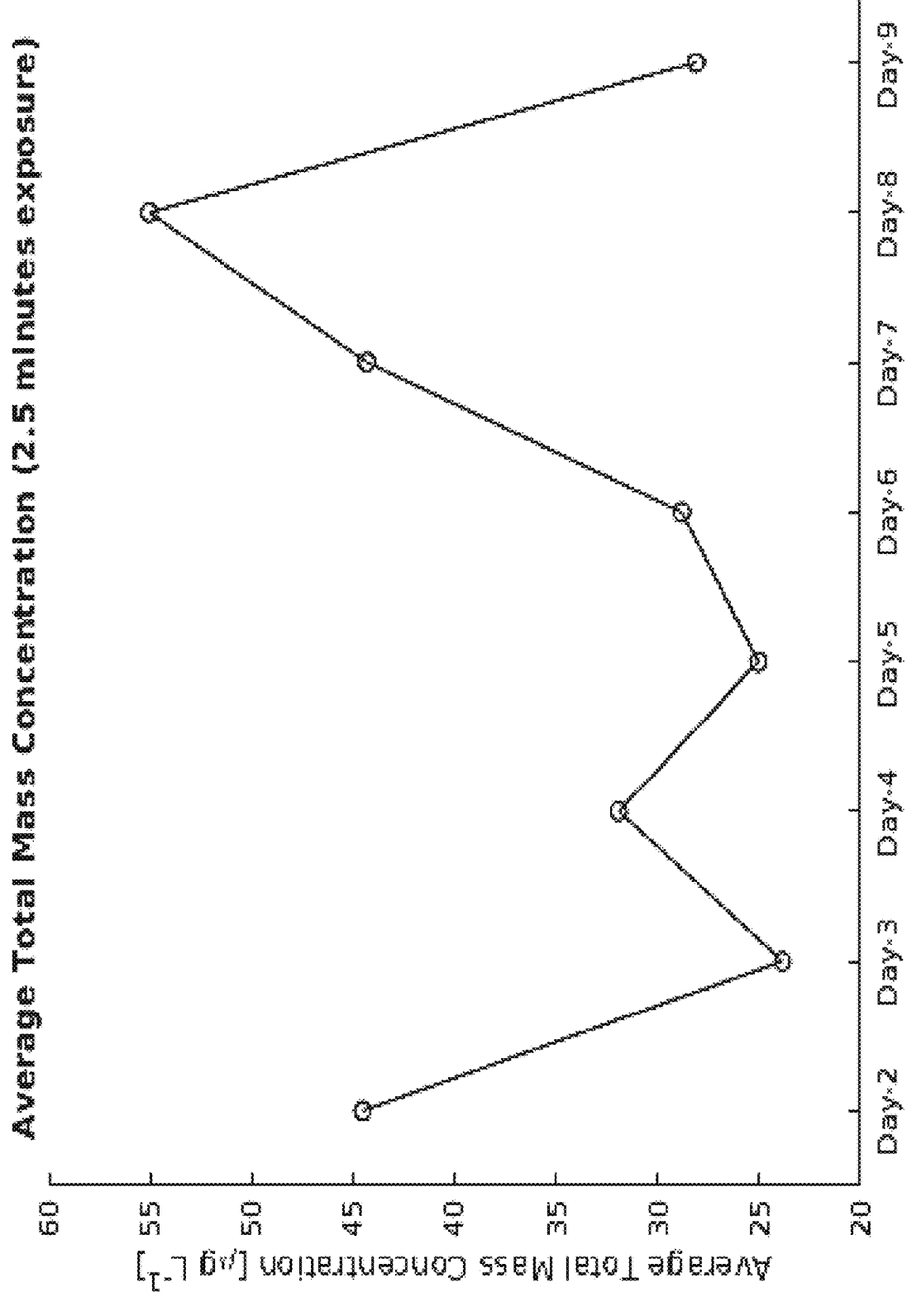

FIG. 15 shows plots of average total mass concentration measured over days following administration of aerosolized fosamprenavir at various exposure times.

Figure 16:
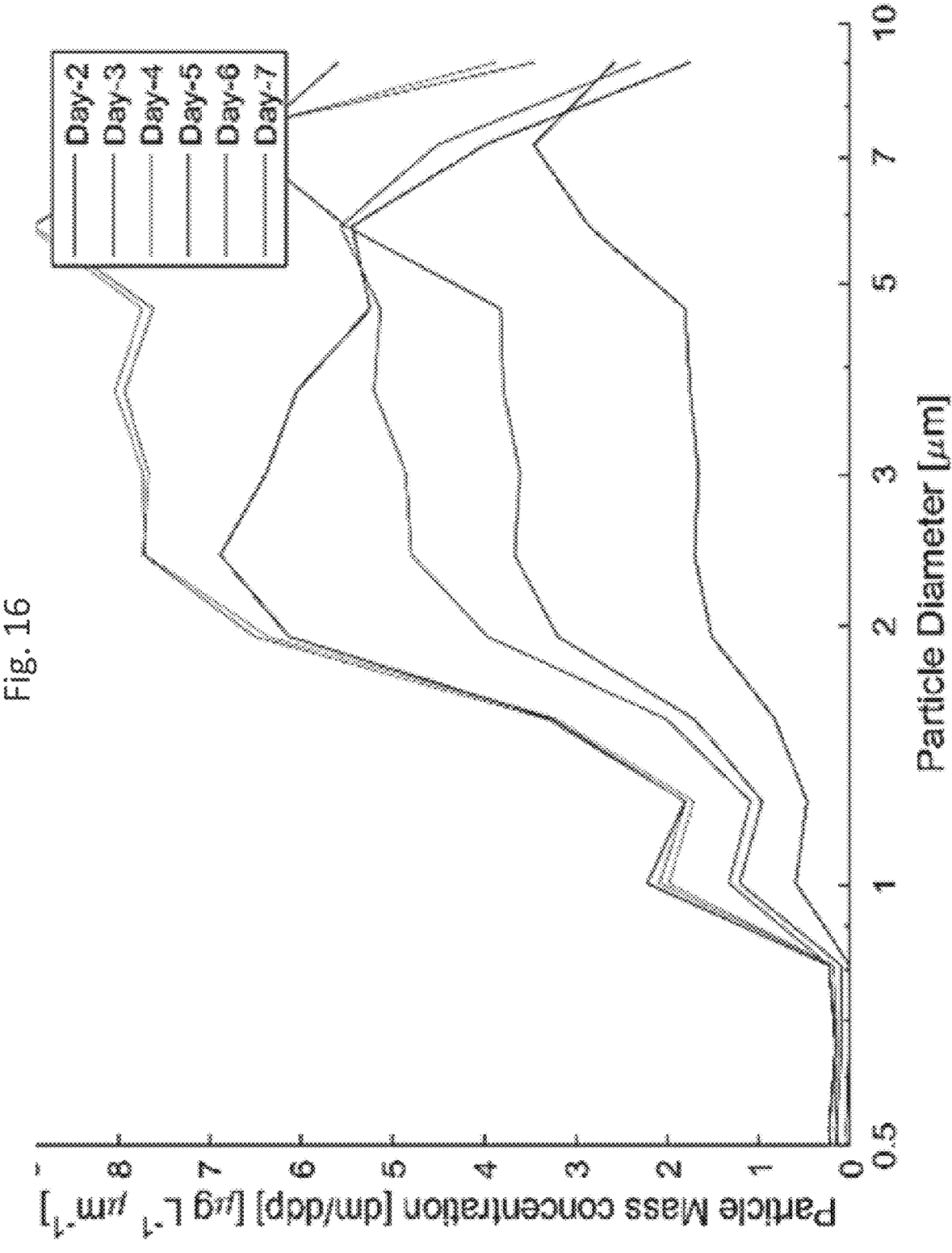

FIG. 16 shows plots of optically measured mass distribution functions for a 10-minute exposure of fosamprevanir aerosols generated with a small-scale powder disperser. Dry powder aerosolization yielded a distribution of particle diameters predominantly within the 2 µm-9 µm range.

Figure 17:
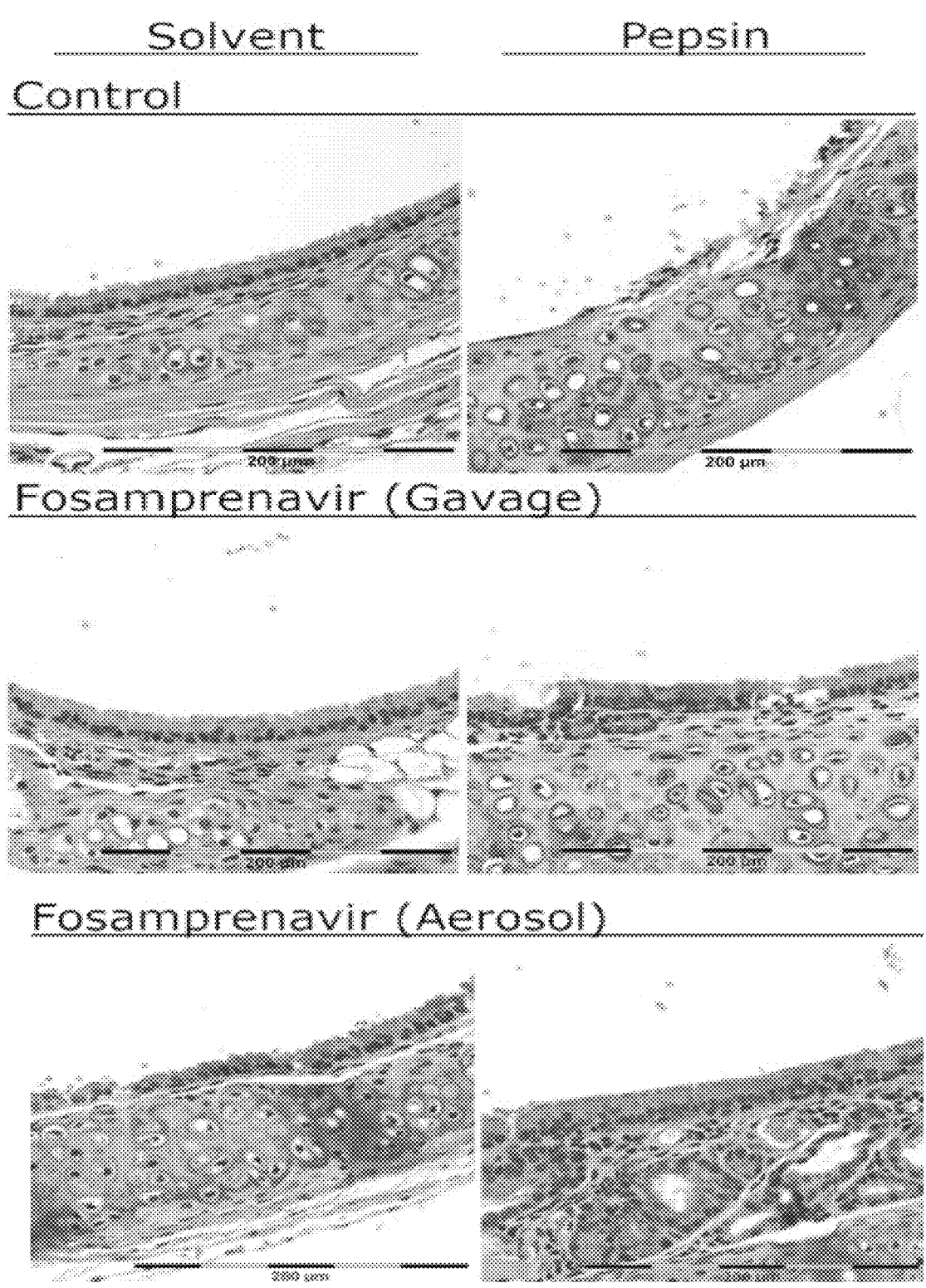
Figure 17:
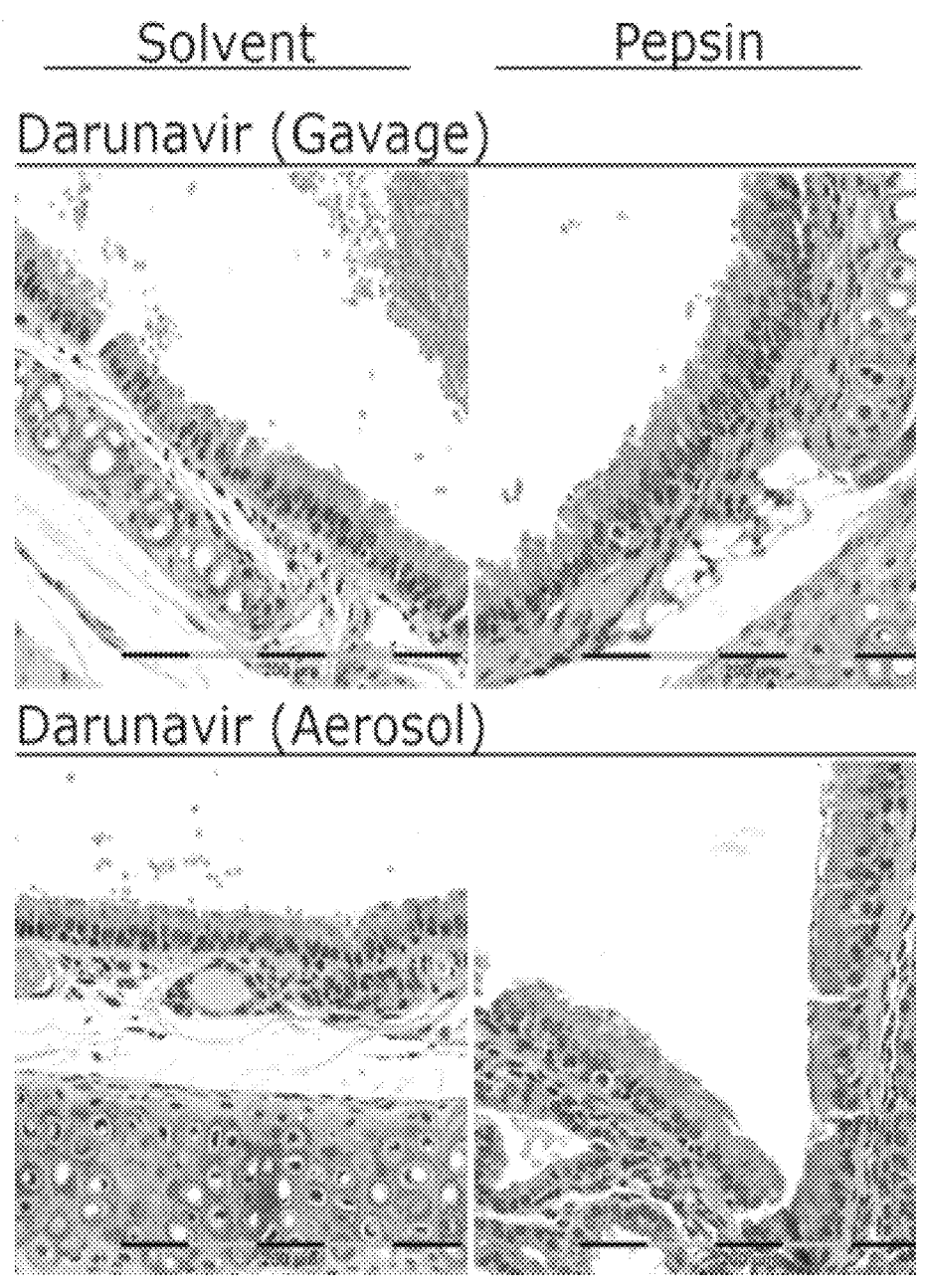

FIG. 17 shows Fosamprenavir gavage and aerosol and darunavir aerosol prevent pepsin-mediated laryngeal damage in vivo. Representative specimens at 400×. Solvent control group laryngeal epithelium was characterized by a single layer of respiratory epithelium with no reactive changes. In mice treated with pepsin-pH7, the laryngeal epithelium exhibited reactive epithelial changes and apoptotic debris. Fosamprenavir gavage and aerosol protected against pepsin-mediated laryngeal damage as indicated by normal histology in mice receiving fosamprenavir gavage or aerosol with saline (solvent), or fosamprenavir gavage or aerosol with pepsin-pH7. Darunavir gavage elicited mild reactivity (rare intraepithelial lymphocytes) in the saline treatment group; the darunavir gavage group with pepsin-pH7 appeared similar. Darunavir aerosol provided mild protection against pepsin-mediated damage. Epithelial injury was still present (mildly increased intraepithelial inflammatory cells and reactive epithelial cells); however no apoptosis was observed. Scale bar=200 um.

DETAILED DESCRIPTION

In the present application, the inventors disclose a novel means to treat reflux conditions, including airway reflux such as laryngopharyngeal reflux (LPR). The deleterious changes in the laryngopharynx observed in LPR develop following direct contact of the mucosa with refluxed gastric contents, which consist of acid as well as pepsin, bile, and pancreatic enzymes. Recent studies have brought about a shift in the perception regarding the underlying cause of LPR, and it is now understood that nonacid components of gastric refluxate significantly contribute to the disease. Studies using combined multichannel intraluminal impedance with pH (MII-pH) monitoring have shown that many episodes of LPR are nonacidic, and that weakly and nonacidic reflux is associated with persistent symptoms in acid-suppressed patients (39-42). Pepsin, the chief digestive enzyme in the stomach, has been increasingly implicated as contributing to the damage and inflammation associated with LPR (17-23). Importantly, while the stomach and esophagus have internal defense mechanisms against pepsin, such as mucus, peristalsis, and bicarbonate secretion, laryngeal tissues do not (26). In the airways, which have a neutral pH (below 8), pepsin is enzymatically inactive but stable. However, when pepsin is taken up by laryngeal and hypopharyngeal cells via receptor-mediated endocytosis, it is retained in intracellular vesicles of low pH where it is presumed to be reactivated and cause damage (20, 32, 33, 49, 52). While many episodes of LPR are weakly acidic or nonacidic, pepsin is present in all refluxate (24), and is frequently detected in airway tissue and secretions from patients with LPR. For example, the inventors have demonstrated that endocytosed nonacidic pepsin induces expression of proinflammatory cytokine genes in hypopharyngeal cells. This response is similar to the response that occurs in reflux esophagitis, which contributes to disease severity in GERD patients (21, 31). Importantly, inhibition of pepsin's proteolytic activity (i.e., using pepstatin, curcumin, ecabet sodium, anthocyanin, or pre-incubation at pH 8.0 before decreasing the pH to 7.0) has been shown to abrogate this damage and inflammation (5, 7, 22, 33, 52, 54-56), making pepsin a promising therapeutic target for the treatment of airway reflux.

The present inventors believe that LPR is more dependent on pepsin-mediated damage than on acid-mediated damage, and that drugs that specifically target pepsin should be effective for patients with nonacid reflux. These drugs could finally provide a treatment option for patients who are refractory to proton pump inhibitors (PPI). Pepsin can be inhibited by two mechanisms: (1) via irreversible inactivation, which prevents it from becoming reactivated inside intracellular compartments of lower pH, and (2) via a receptor antagonist, which prevents pepsin uptake by receptor-mediated endocytosis. While the pepsin inhibitor pepstatin is already commercially available, it has poor water-soluble characteristics and pharmacokinetic properties. Thus, new pepsin inhibitor compounds with greater bioavailability are needed.

Figure 3:
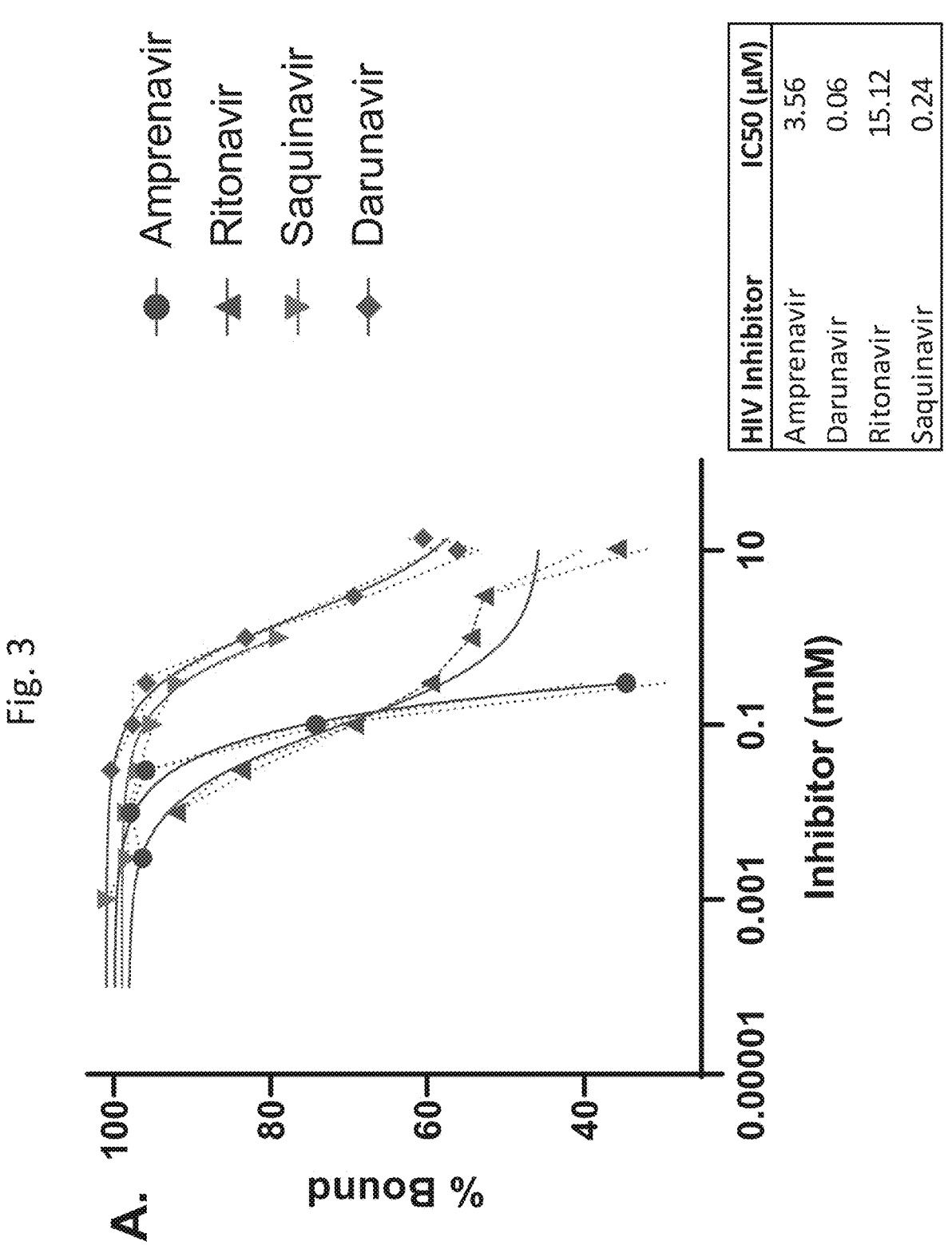
FIG. 3 shows binding (A) and activity (B) curves of pepsin in the presence of the indicated HIV protease inhibitors.
Figure 3:
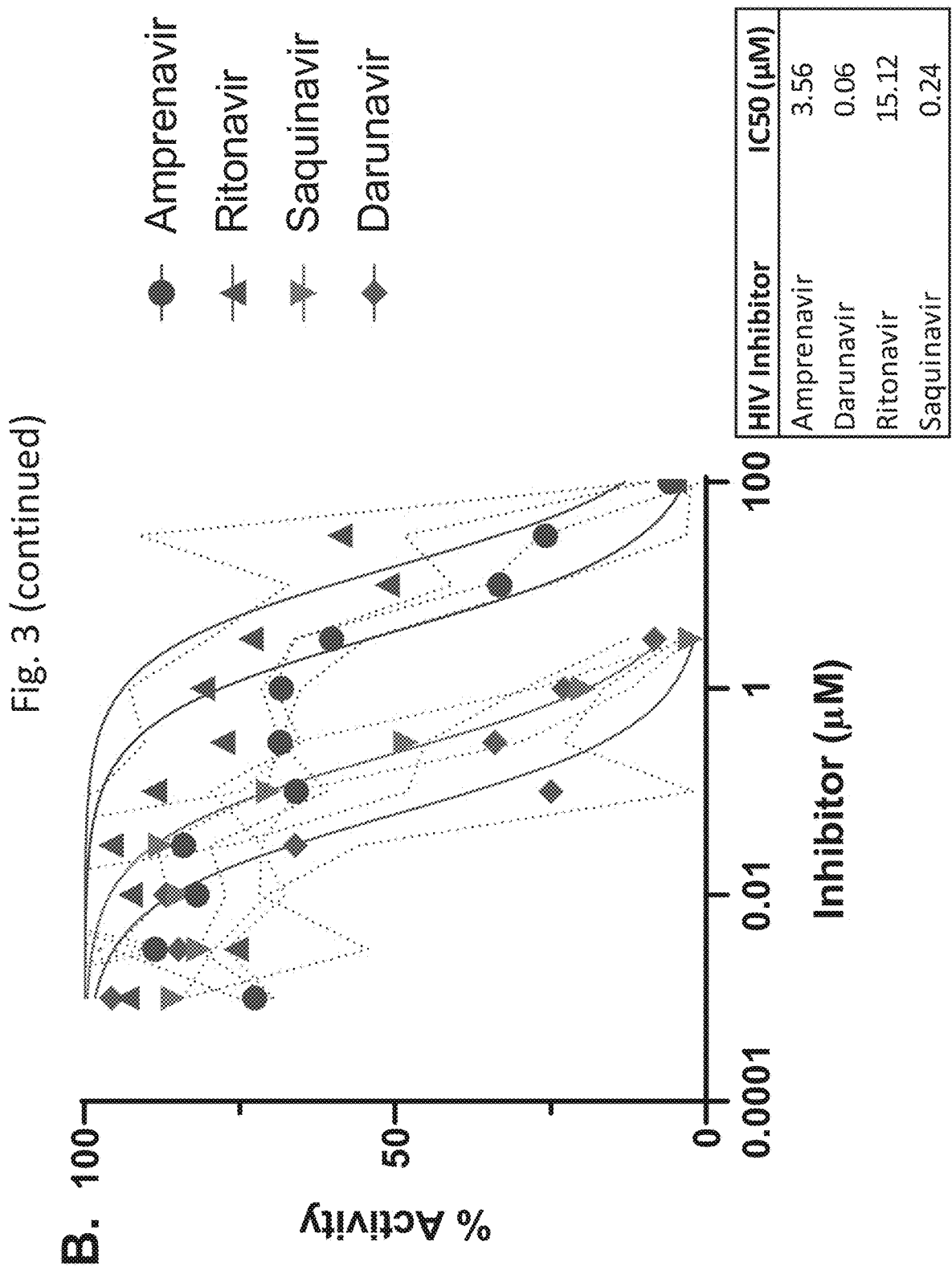
Figure 5:
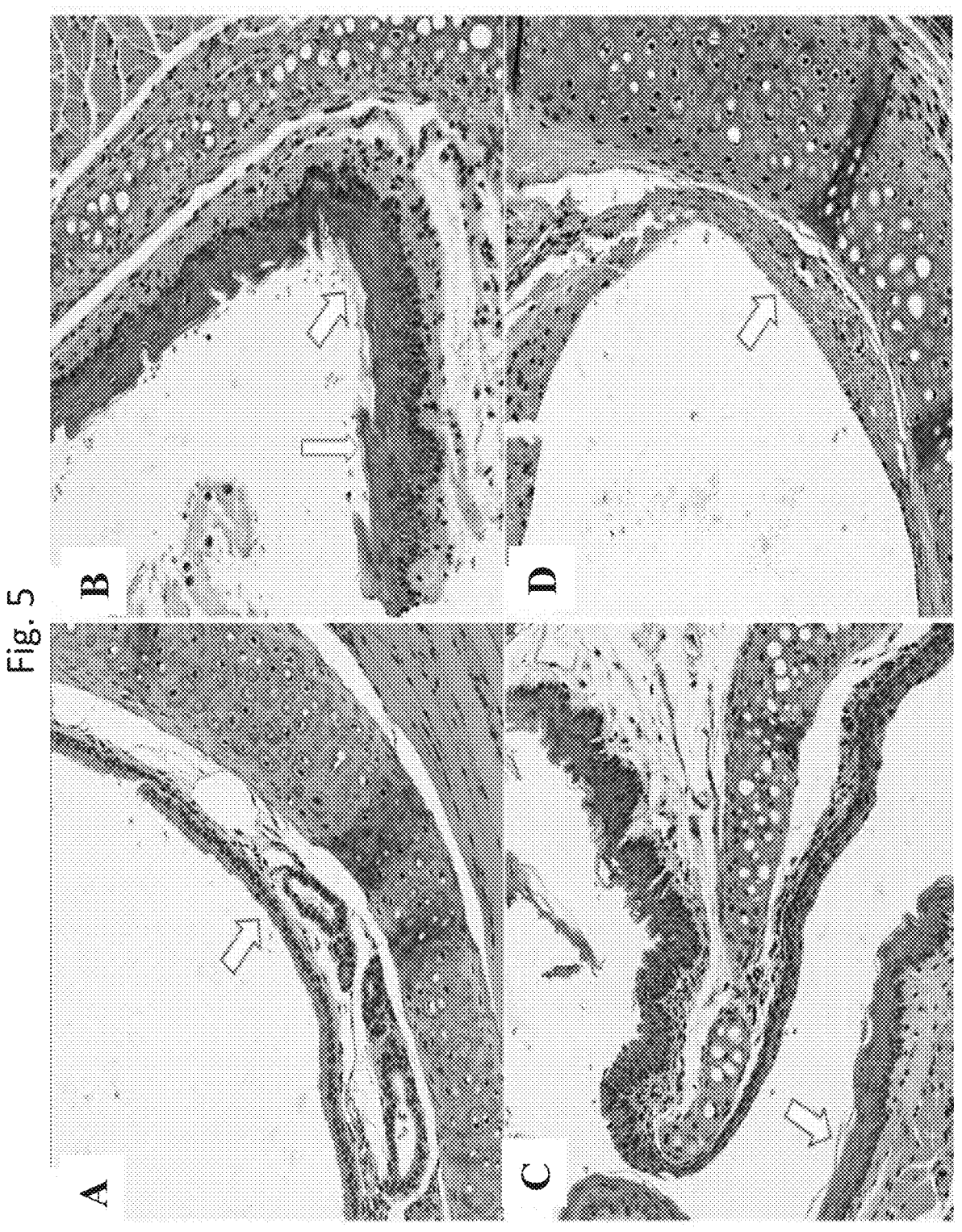
FIG. 5 depicts airway epithelial damage by pepsin in vivo. Representative animals from the different treatment protocols shown in each panel: pH 7 (panel A, E), pH 4 (panel B, F), 0.3 mg/ml pepsin at pH 7 (panel C, G), and 0.3 mg/ml pepsin at pH 4 (panel D, H). Panels A-D: 20× magnification; panels E-H: 50× magnification. (A, E) Normal respiratory epithelium (arrow) about one cell layer thick with basal polarization of the nuclei and ciliated apical surfaces. (B, F) Reactive respiratory epithelium characterized by thickening (fat arrow) and focal squamous metaplasia (long arrow) with loss of cilia. In other areas, relative thickening of the mucosa with moderately increased nuclear to cytoplasmic (N:C)
Figure 5:
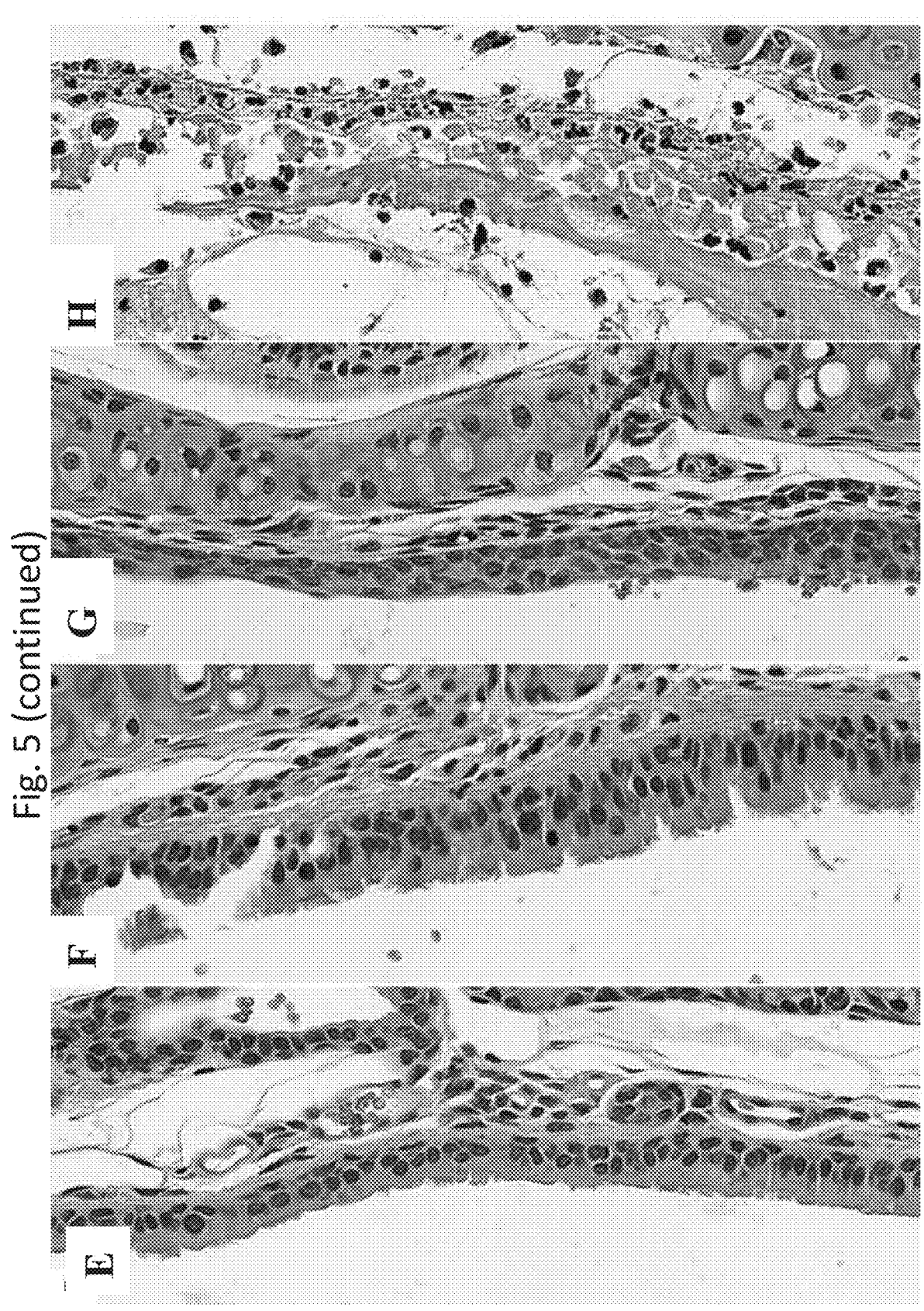

In the present application, the inventors screened therapeutic compounds for their ability to bind to pepsin and inhibit its enzymatic activity and identified specific HIV protease inhibitors with these abilities (see Example 1). Several HIV protease inhibitors have already been approved by the U.S. Food and Drug Administration (FDA) for the treatment of HIV, making these drugs ideal candidates to test the efficacy of pepsin inhibition for the treatment of LPR. Using epidemiological data, the inventors demonstrated that patients taking HIV protease inhibitors have a significantly lower incidence of airway reflux (0.2%) compared to the general population (10-34.4%), supporting the idea that these HIV drugs might be repurposed to treat LPR. Of the ten commercially available HIV protease inhibitors, the inventors determined that four (i.e., amprenavir, darunavir, ritonavir, and saquinavir) have the ability to bind to and inhibit pepsin activity in vitro (FIG. 3). To test these drug candidates in vivo, the inventors established a novel mouse model of LPR (FIG. 5). These mice were used to test the ability of HIV protease inhibitors to ameliorate pepsin-mediated laryngeal mucosal damage and inflammation. The mice were given HIV protease inhibitors both by oral gavage and by aerosolized delivery to compare the results of systemic and local delivery, respectively. Building on the results of these animal studies, the inventors will test the efficacy of promising HIV protease inhibitors in a 12-week randomized, double blind, placebo-controlled clinical trial (see Example 2).

Methods

The present invention provides methods of treating reflux in a subject in need thereof, preferably airway reflux. The methods involve administering a therapeutically effective amount of an HIV protease inhibitor to a subject to treat the reflux. As used herein, the term "airway reflux" refers to inflammation of the upper and lower airways caused by reflux of gastric contents. The term airway reflux is used interchangeably with the alternative terms "supraoesophageal reflux" and "extraoesophageal reflux." These broad terms encompass several related reflux conditions, which include gastropharyngeal reflux (GPR; the backflow of gastric contents up to the esophagus), laryngopharyngeal reflux (LPR; the backflow of gastric contents beyond the esophagus into the laryngopharynx), and esophagopharyngeal reflux (EPR; a similar condition to LPR that is characterized by esophageal abnormalities). Reflux also includes gastroesophageal reflux disease (GERD) which refers to irritation of the esophagus caused by reflux of stomach's contents back up into the esophagus. The reflux treated herein is preferably GERD patients that are refractory to protein pump inhibitor (PPI) therapy.

As used herein, the term "HIV protease inhibitor" refers to any antiviral drug that inhibits one or more HIV proteases. HIV protease inhibitors prevent viral replication by selectively binding to HIV proteases and blocking proteolytic cleavage of protein precursors that are necessary for the production of infectious viral particles. Suitable HIV protease inhibitors include those that have been approved by the Food and Drug Administration (FDA) for the treatment of HIV, including amprenavir (IUPAC: [(3S)-oxolan-3-yl] N-[(2S,3R)-4-[(4-aminophenyl)sulfonyl-(2-methylpropyl) amino]-3-hydroxy-1-phenylbutan-2-yl]carbamate), ritonavir (IUPAC: 1,3-thiazol-5-ylmethyl N-[(2S,3 S,5S)-3-hydroxy-5-[[(2S)-3-methyl-2-[[methyl-[(2-propan-2-yl-1,3-thiazol-4-yl)methyl]carbamoyl]amino]butanoyl]amino]-1, 6-diphenylhexan-2-yl]carbamate), lopinavir (IUPAC: (2S)—N-[(2S,4S,5 S)-5-[[2-(2,6-dimethylphenoxy)acetyl] amino]-4-hydroxy-1,6-diphenylhexan-2-yl]-3-methyl-2-(2-oxo-1,3-diazinan-1-yl)butanamide), saquinavir (IUPAC: (2S)—N-[(2S,3R)-4-[(3 S,4aS,8aS)-3-(tert-butylcarbamoyl)-3,4,4a,5,6,7,8,8a-octahydro-1H-isoquinolin-2-yl]-3-hydroxy-1-phenylbutan-2-yl]-2-(quinoline-2-carbonylamino)butanediamide), nelfinavir (IUPAC: (3 S,4aS, 8aS)-N-tert-butyl-2-[(2R,3R)-2-hydroxy-3-[(3-hydroxy-2-methylbenzoyl)amino]-4-phenyl sulfanylbutyl]-3,4,4a,5,6, 7,8,8a-octahydro-1H-isoquinoline-3-carboxamide), darunavir (IUPAC: [(3a S,4R,6aR)-2,3,3a,4,5,6a-hexahydrofuro[2,3-b]furan-4-yl] N-[(2S,3R)-4-[(4-aminophenyl) sulfonyl-(2-methylpropyl)amino]-3-hydroxy-1-phenylbutan-2-yl]carbamate), indinavir ((2S)-1-[(2S,4R)-4-benzyl-2-hydroxy-5-[[(1 S,2R)-2-hydroxy-2,3-dihydro-1H-inden-1-yl]amino]-5-oxopentyl]-N-tert-butyl-4-(pyridin-3-ylmethyl) piperazine-2-carboxamide), atazanavir (IUPAC: methyl N-[(2S)-1-[2-[(2S,3 S)-2-hydroxy-3-[[(2 S)-2-(methoxycarbonylamino)-3,3-dimethylbutanoyl]amino]-4-phenylbutyl]-2-[(4-pyridin-2-ylphenyl)methyl]hydrazinyl]-3,3-dimethyl-1-oxobutan-2-yl]carbamate), tipranavir (IUPAC: N-[3-[(1R)-1-[(2R)-4-hydroxy-6-oxo-2-(2-phenylethyl)-2-propyl-3H-pyran-5-yl]propyl]phenyl]-5-(trifluoromethyl) pyridine-2-sulfonamide), and cobicistat (IUPAC: 1,3-thiazol-5-ylmethyl N-[(2R,5R)-5-[[(2 S)-2-[[methyl-[(2-propan-2-yl-1,3-thiazol-4-yl)methyl]carbamoyl]amino]-4-morpholin-4-ylbutanoyl]amino]-1,6-diphenylhexan-2-yl] carbamate). The HIV protease inhibitor used with the present invention should be capable of binding to and inhibiting the enzymatic activity of pepsin. Thus, in some embodiments, the HIV protease inhibitor is amprenavir, darunavir, ritonavir, or saquinavir, which were shown to bind to and inhibit pepsin in Example 1. In some embodiments, the HIV protease inhibitor is amprenavir (IUPAC: [(3 S)-oxolan-3-yl]N-[(2S,3R)-4-[(4-aminophenyl)sulfonyl-(2-methylpropyl)amino]-3-hydroxy-1-phenylbutan-2-yl]carbamate) or its prodrug fosamprenavir (IUPAC: [(3 S)-oxolan-3-yl]N-[(2S,3R)-4-[(4-aminophenyl)sulfonyl-(2-methylpropyl)amino]-1-phenyl-3-phosphonooxybutan-2-yl] carbamate). HIV protease inhibitors are known in the art and commercially available.

Fosamprenavir is a prodrug of amprenavir that is marketed by ViiV Healthcare as a calcium salt under the trade names Lexiva (U.S.) and Telzir (Europe). The body must metabolize fosamprenavir to form amprenavir, which is the active form of the drug. Thus, administering amprenavir as a prodrug prolongs the duration of time that it is available in the body, acting like a slow release formulation. Further, fosamprenavir has shown excellent pharmacokinetics in mice and because it is already FDA approved, fosamprenavir could be fast-tracked into a pilot clinical trial. In some embodiments, the HIV protease inhibitors for use in the compositions and methods described herein have an $IC_{50}$ in the micromolar range (µm). In some preferred embodiments, the HIV protease inhibitors for use in the compositions and methods described herein have an $IC_{50}$ in the nanomolar (nm) range.

In the present methods, the HIV protease inhibitor may be administered using any route that is effective for the treatment of reflux, preferably airway reflux. As used herein, the terms "administering" and "administration" refer to any method of providing a pharmaceutical preparation to a subject. Such methods are well known to those skilled in the art and include, but are not limited to, oral administration, administration by inhalation, nasal administration, nebulizer administration, or other routes of administration that would reach the upper airways. Administration can be continuous or intermittent.

In some embodiments, the HIV protease inhibitor is administered orally for the treatment of the reflux. For example, in some embodiments, the HIV protease inhibitor is administered twice daily at about 0.7-1.4 g (i.e., a dosage that is FDA-approved for the treatment of HIV and thus safe). However, the inventors hypothesize that administrating the drugs in an aerosolized form would increase the local delivery and improve efficacy. (See the section titled Compositions for a more detailed discussion of aerosolized formulations.) Thus, in some embodiments, the HIV protease inhibitor is administered as an aerosol. For example, in certain embodiments, the HIV protease inhibitor is administered as a nasal spray, and in other embodiments, it is administered via an inhaler. In some embodiments, the HIV protease inhibitor is administered at dosages lower than 1.4 g twice daily, including, lower than 0.7 g twice daily, and may include, in some embodiments, dosages in the µg amount twice daily.

Oral administration of fosamprenavir, as Lexiva 20 mg/kg/day, equivalent to the dose used to treat HIV in humans, prevented pepsin-mediated laryngeal injury (defined as multi-layered, reactive epithelia and cell apoptosis) in our in vivo mouse model (FIG. 7). In contrast, oral administration of darunavir, as Prezista 8.6 mg/kg/day, also the human equivalent dose, did not abrogate pepsin mediated laryngeal injury (FIG. 7H). Fosamprenavir was administered by inhalation at a dose of 1 mg/kg/d prevented pepsin mediated laryngeal injury (FIG. 7F). Significantly, darunavir administered as an aerosol at a dose of 12 mg/kg/d (FIG. 7J) was also effective in preventing pepsin mediated injury. The inhalation dose is calculated from the measured exposure conditions and implicitly assumes that all drug is deposited. The actual deposition is likely near 10%.

The methods of the present invention are used to treat to reflux in a subject in need thereof. In some embodiments, the reflux may be airway reflux. In other embodiments, the reflux may be GERD, preferably GERD in a subject that is refractory to proton pump inhibition. As used herein, the term "subject in need thereof" or "patient" refers to any human or animal suffering from reflux. In some embodiments, the subject has an airway reflux. In some embodiments, the airway reflux condition selected from laryngopharyngeal reflux (LPR), gastropharyngeal reflux (GPR), and esophagopharyngeal reflux (EPR). In some embodiments, the subject is a subject with reflux episodes caused by weakly acidic or nonacidic reflux. In another embodiment, the subject is a subject refractory to proton pump inhibitor (PPI) therapy.

As used herein, the terms "treat", "treating" or "treatment" describes the management and care of a subject for the purpose of combating a disease, condition, or disorder. Treating includes the administration of protease inhibitor or composition of present invention to prevent the onset of the symptoms or complications, to alleviate the symptoms or complications, or to eliminate the disease, condition, or disorder. In preferred embodiments, the methods and compositions of the present reduce mucosal damage and inflammation in the airway of the subject. Treatment also includes reducing one or more symptoms of airway reflux, suitably LPR, GPR or ERP, for example, reduction of chronic cough, throat clearing, postnasal drip, hoarseness or dysphonia, globus sensation, dysphagia, dyspnea, or combinations thereof. Treatment also includes reducing chronic laryngeal irritation and inflammation. Treatment in one embodiment also includes reducing one or more symptom of GERD that is refractory to PPI, for example, reducing one or more of the following symptoms: a burning sensation in your chest (heartburn), usually after eating, which might be worse at night, chest pain, difficulty swallowing, regurgitation of food or sour liquid, sensation of a lump in your throat, among others.

The terms "effective amount" or "therapeutically effective amount" refer to an amount sufficient to effect beneficial or desirable biological or clinical results. That result can be reducing, alleviating, inhibiting or preventing one or more symptoms of a disease or condition, reducing, inhibiting or preventing laryngeal irritation, reducing or inhibiting laryngeal irritation or mucosal damage, or reducing, alleviating, inhibiting or preventing one or more symptoms of airway reflux, or any other desired alteration of a biological system. In some embodiments, the effective amount is an amount suitable to provide the desired effect, e.g., reduce mucosal damage and inflammation in the airway. The response to a treatment of airway reflux may be assessed using any standard clinical method including, without limitation, visual inspection of the larynx (e.g., fiberoptic laryngeal exam), a reflux symptom index (RSI), reflux finding score (RFS) (e.g., physician reported score based on visual inspection of the larynx), combined esophageal multichannel intraluminal impedance and pH monitoring (MII-pH), reflux symptom score (RSS), reflux sign assessment (RSA), or pepsin activity within the saliva. Alternatively, the response to a treatment of airway reflux may be assessed using by evaluating the inflammation in a tissue sample taken from the airway of the subject, for example, by hematoxylin and eosin (H&E) staining or by detection of the presence of neutrophil infiltrate, keratinization, and necrosis. Another suitable method is measure pepsin activity pre and post 12-week treatment. While it is not expected that the HIV inhibitor will prevent reflux or affect pepsin protein levels, it will inactivate the pepsin enzyme, therefore measuring pepsin activity in saliva post-treatment would confirm that the treatment is inactivating pepsin in the airway. This is currently a research tool to assess efficacy in vivo.

Patients with reflux episodes caused by weakly acidic or nonacidic reflux are largely refractory to proton pump inhibitor (PPI) therapy, which suppresses acid production but does not affect pepsin activity. The methods of the present invention will be of particular benefit to this group of refractory patients, who are in desperate need of an alternative to PPIs. As used herein, the phrase "refectory to treatment" refers to a condition that does not respond to treatment. For example, a patient's reflux may be deemed refractory to PPI therapy if a three-month long, twice-daily treatment with a PPI fails to improve the condition substantially. The response to a treatment of reflux may be assessed using any standard means known in the art including, without limitation, a reflux symptom index (RSI), reflux finding score (RFS), combined esophageal multichannel intraluminal impedance and pH monitoring (MII-pH), reflux symptom score (RSS), or reflux sign assessment (RSA). See the Examples section for a more detailed description of these measures. For example, an effective treatment would decrease the RSI and/or the RFS to normative values, e.g., RSI≤13, RFS≤7 or a combination thereof.

In some embodiments a subject may be administered a HIV protease inhibitor alone or in conjunction with one or more additional therapeutic agents. For example, a HIV protease inhibitor of the present disclosure may be administered in addition to a PPI. A combination of a HIV protease inhibitor and an additional therapeutic agent(s) may occur if, for example, a PPI provides partial, but not complete, relief from symptoms. The PPI and HIV protease inhibitor may be administered in routes and doses that are most therapeutically effective as determined by one skilled in the art, and maybe be changed or eliminated as therapeutically necessary.

Compositions:

The present invention also provides compositions comprising an aerosolized formulation of an HIV protease inhibitor and, optionally, a pharmaceutically acceptable carrier. Commercially available HIV protease inhibitors are commonly formulated as tablets or oral suspensions for systemic drug delivery. However, the present inventors submit that the HIV protease inhibitors that can inhibit pepsin for use herein may be more effective for the treatment of airway reflux when delivered locally. Thus, the present invention provides reformulated HIV protease inhibitors in aerosolized forms for delivery by inhalation. For example, in some embodiments, the aerosol is formulated for oral administration or nasal administration. In one example, the aerosol may be formulated for inhalation. The present invention also encompasses use of these aerosolized formulations of HIV protease inhibitors for the treatment of acid reflux in a subject in need thereof.

As used herein, the term "aerosolization" refers to a process by which a substance is converted into a fine spray or colloidal suspension in air. Aerosolization is typically accomplished using an aerosol generator, such as an aerosol drug delivery device. Suitable aerosol drug delivery devices for use with the present invention include, without limitation, pressurized metered-dose inhalers, dry-powder inhalers, spacers and holding chambers, and nebulizers. As is understood by those of skill in the art, each of these devices may require different drug formulations. For instance, for use with a pressurized metered-dose inhaler, drugs are mixed with propellants (e.g., halogenated fluoroalkanes, such as HFA227 and HFA134A). For use with a dry-powder inhaler, drugs are formulated as a powder that is often mixed with other powders (e.g., lactose) to reduce aggregation. Nebulizers vary widely in concept and can be designed for use with a broad range of liquid formulations. Thus, in some embodiments, the composition is a liquid or suspension. In other embodiments, the composition is a lyophilized or otherwise dried formulation.

Delivering drugs by inhalation requires a formulation that can be successfully aerosolized. The mouse inhalation studies involved optimized delivery to the mouse model with administration of pure drug contained in a relatively small aerosol particles (i.e. 1 μm). For translation from in vivo to clinical application, the drug can be reformulated to optimize inhalation delivery to humans. Here, a larger particle size would be generated to take advantage of the fact that humans can be instructed to take controlled forceful inhalations to maximize particle deposition. A computational fluid dynamics analysis of laryngeal particle deposition revealed an optimal particle size is 9 to 12 microns for deposition in the larynx (unpublished data) which is in good agreement with other studies (Perkins et al., 2018). Specifically, to generate a therapeutic effect, the particles or droplets of an aerosolized drug need to be of a sufficient size and mass to be carried to the section of the airway that requires treatment (i.e., the pharynx). As aerosol particles are inhaled orally or through the nose, larger particles (>10 μm) are filtered in the nose and/or the throat (largely by inertial impaction), whereas particles of 5-10 μm generally reach the proximal generations of the lower respiratory tract, and particles of 1-5 μm reach the lung periphery. Thus, in some embodiments, the HIV protease inhibitor particles within the aerosol are 1-15 μm in size on average. However, for increased laryngeal deposition, the HIV protease inhibitor particles within the aerosol are 5-15 μm in size on average. In some embodiments, the HIV protease inhibitor particles within the aerosol are 1-10 μm in size on average, or are 2-9 μm in size on average, or other average sizes in-between, for example, about 1 μm, 1.5 μm, 2 μm, 2.5 μm, 3.0 μm, 3.5 μm, 4.0 μm, 4.5 μm, 5.0 μm, 5.5 μm, 6.0 μm, 6.5 μm, 7.0 μm, 7.5 μm, 8 μm, 8.5 μm, 9 μm. In other embodiments, the HIV protease inhibitor particles within the aerosol are 8-12 μm in size on average, are 9-12 μm in size on average, or are 8-10 μm in size on average, or other average sizes in-between, for example, 8 μm, 8.5 μm, 9 μm, 9.5 μm, 10 μm, 10.5 μm, 11 μm, 12 μm, etc. For example, for use with the present invention, an HIV protease inhibitor may be aerosolized using an ultrasonic atomizer, as described in detail in the Materials and Methods section of Example 1. Additionally or alternatively, the HIV protease inhibitor may be aerosolized using a dry powder inhaler or small-scale powder disperser, as described in Example 3.

The compositions of the present invention may optionally include any pharmaceutically acceptable carrier that allows for aerosolized delivery. "Pharmaceutically acceptable carriers" are known in the art and include, but are not limited to, for example, suitable diluents, preservatives, solubilizes, emulsifiers, liposomes, nanoparticles, and adjuvants. Pharmaceutically acceptable carriers may be aqueous or non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include isotonic solutions, alcoholic/aqueous solutions, emulsions or suspensions, including saline and buffered media.

The compositions of the present invention may further include additional components to influence the physical state, solubility, stability, rate of in vivo release, and rate of in vivo clearance of the HIV protease inhibitor. Suitable components include, without limitation, buffers (e.g., Tris-HCl, acetate, phosphate), additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances, and tonicity modifiers (e.g., lactose, mannitol). Additionally, the compositions may be formulated for controlled or sustained release of the HIV protease inhibitor, for example, via formulation in lipophilic depots (e.g., fatty acids, waxes, oils).

The compositions may be prepared in unit dosage forms for administration to a subject. The amount and timing of administration are at the discretion of the treating clinician to achieve the desired outcome.

The HIV protease inhibitor included in the compositions of the present invention may be any HIV protease inhibitor that is suitable for the treatment of airway reflux, as discussed above. In some embodiments, the HIV protease inhibitor included in the composition is amprenavir, darunavir, ritonavir, saquinavir, or a derivative thereof. In preferred embodiments, the HIV protease inhibitor is amprenavir or its prodrug fosamprenavir. In another embodiment, the HIV protease inhibitor is darunavir.

The present invention has been described in terms of one or more preferred embodiments, and it should be appreciated that many equivalents, alternatives, variations, and modifications, aside from those expressly stated, are possible and within the scope of the invention.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. For example, with regard to sequences "consisting of" refers to the sequence listed in the SEQ ID NO. and does refer to larger sequences that may contain the SEQ ID as a portion thereof.

The references cited herein are explicitly incorporated by reference in their entireties.

The invention will be more fully understood upon consideration of the following non-limiting examples.

EXAMPLES

Example 1: In Vitro and Animal Assessment of HIV Protease Inhibitors for the Treatment of Airway Reflux In the following Example, the inventors used binding and enzymatic assays to assess the ability of ten commercially available, FDA-approved HIV protease inhibitors to bind to and inhibit pepsin. The inventors then used co-crystallization of these inhibitors with pepsin to help identify the best drug candidate to test in subsequent studies. Finally, the inventors established a mouse model of laryngopharyngeal reflux (LPR). The inventors used these mice to test the ability of the candidate drugs to abrogate pepsin-mediated laryngeal damage, both when administered by oral gavage and when administered by aerosolized delivery.

Background

The deleterious changes in the laryngopharynx observed in LPR develop following direct contact of the mucosa with refluxed gastric contents, which consist of acid as well as pepsin, bile, and pancreatic enzymes. Because the acidity of the reflux alone can cause tissue damage in the upper airway, LPR was once considered an acid-mediated disease. However, recent studies have brought about a shift in the perception regarding the underlying cause of LPR, and it is now understood that nonacid components of gastric refluxate significantly contribute to the disease. While in vitro studies report bile induced mucosal damage at nonacid pH, there is no evidence that the same process occurs in the human larynx, possibly because the concentration of bile reaching the proximal laryngopharynx is insufficient to cause cell membrane damage (19). Studies using combined multichannel intraluminal impedance with pH (MII-pH) monitoring have shown that many episodes of LPR are nonacidic, and that weakly and nonacidic reflux is associated with persistent symptoms in acid-suppressed patients (39-42).

Pepsin, the chief digestive enzyme in the stomach, has been increasingly implicated as contributing to the damage and inflammation associated with LPR (17-23). Pepsin is a proteolytic enzyme that is initially synthesized and secreted as the zymogen pepsinogen by chief cells in the gastric fundus, and is subsequently cleaved in an autocatalytic fashion to produce the mature form of pepsin upon introduction to the acidic environment of the stomach lumen. Importantly, while the stomach and esophagus have internal defense mechanisms against pepsin, such as mucus, peristalsis, and bicarbonate secretion, laryngeal tissues do not (26). Pepsin is maximally active at pH 2 and continues to have activity up to pH 6.5. In fact, the enzyme remains stable up to pH 8, above which the secondary structure of the molecule is lost and the enzyme is irreversibly inactivated (20, 25). In the airways, which have a neutral pH (below 8), pepsin is enzymatically inactive but stable. However, when pepsin is taken up by laryngeal and hypopharyngeal cells via receptor-mediated endocytosis, it is retained in intracellular vesicles of low pH where it is presumed to be reactivated and cause damage (20, 32, 33, 49, 52). While many episodes of LPR are weakly acidic or nonacidic, pepsin is present in all refluxate (24), and is frequently detected in airway tissue and secretions from patients with LPR. Further, studies have demonstrated that endocytosed pepsin causes mitochondrial damage and upregulates the expression of several genes implicated in stress and toxicity (53). For example, the inventors have demonstrated that endocytosed nonacidic pepsin induces expression of proinflammatory cytokine genes in hypopharyngeal cells. This response is similar to the response that occurs in reflux esophagitis, which contributes to disease severity in GERD patients (21, 31). Importantly, inhibition of pepsin's proteolytic activity (i.e., using pepstatin, curcumin, ecabet sodium, anthocyanin, or pre-incubation at pH 8.0 before decreasing the pH to 7.0) has been shown to abrogate this damage and inflammation (5, 7, 22, 33, 52, 54-56), making pepsin a promising therapeutic target for the treatment of airway reflux.

Materials and Methods

Competitive Binding and Activity Assays

Figure 1:
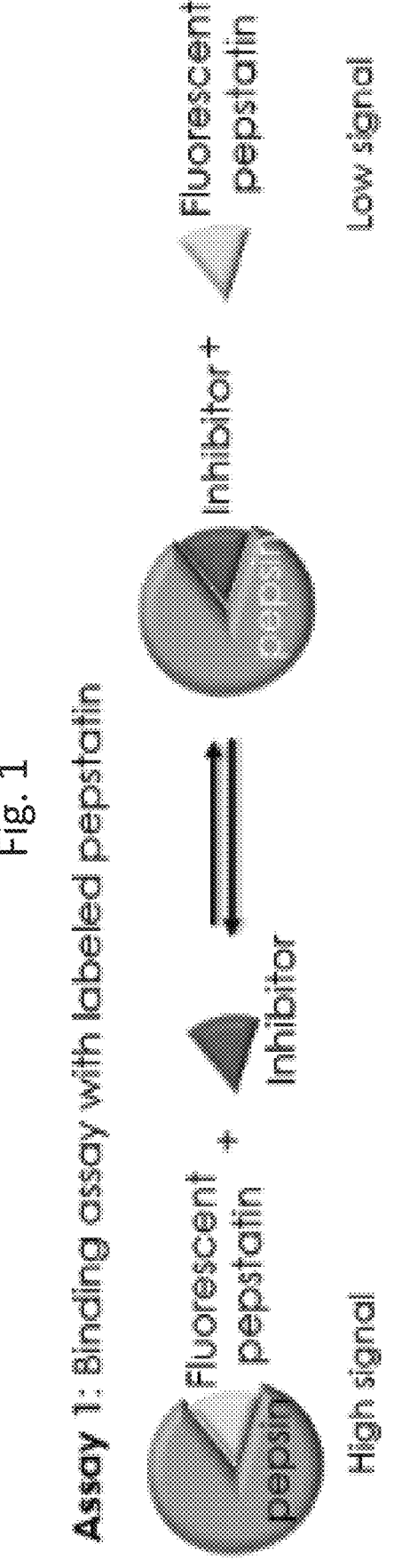
FIG. 1 shows a schematic of the assays used to screen for compounds that inhibit pepsin. Assay 1 (top) is a binding assay that measures how well a compound competes with fluorescently labeled pepstatin for its binding site on pepsin. Assay 2 (bottom) is a peptic activity assay that utilizes fluorescently labeled casein as an enzymatic substrate.
Figure 1:
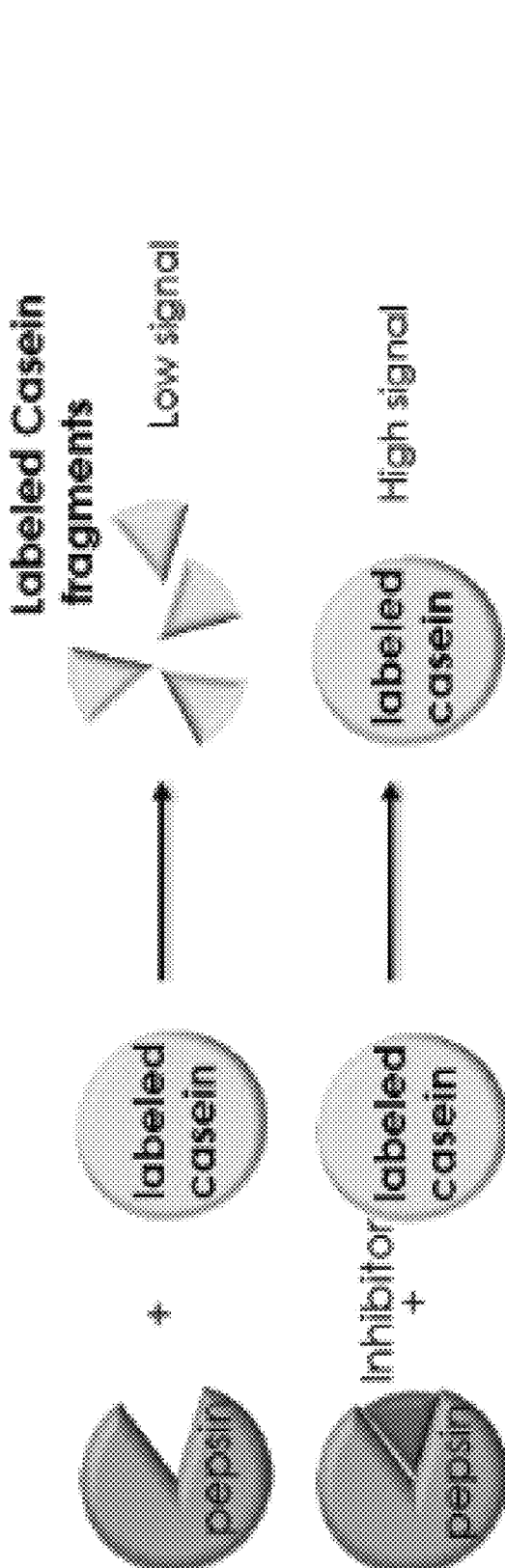

Fluorescent polarization assays were developed to test compound binding and inhibition of pepsin (FIG. 1). A competitive binding assay was developed using pepstatin, a known inhibitor of pepsin with subnanomolar affinity[91] (Roberts 2003). This binding assay measures the relative binding affinity but not the enzymatic inhibition of compounds. Thus, a separate peptic activity assay was developed, which uses fluorescently labelled alpha casein as substrate. Both assays are based on the principle of fluorescence polarization (FP), which holds that as the molecular size of a fluorescent species is altered through dissociation/breakdown or association/binding events, the degree of depolarization of plane polarized light changes accordingly, directly affecting the FP value.[92] (Lea 2011). In the assays used herein, millipolarization (mP) decreases as casein-Alexa647 is degraded by pepsin and increases with binding of pepsin to pepstatin-Alexa647.

Casein was labeled as described by Jolley (1996)[93] using a 2.5 ug/mg label to protein ratio. Specifically, 200 ul 10 mg/ml bovine alpha casein (C6780 Sigma Aldrich, St. Louis, MO) in 0.1M sodium bicarbonate was incubated with 5 ul 1 mg/ml Alexa Fluor 647 Carboxylic Acid, Succinimidyl Ester (in DMSO; A-20106 ThermoFisher Scientific, Waltham, MA) for 15 minutes at room temperature. The mixture was applied to a Sephadex G-25 column (90×5 mm) in a glass Pasteur pipette. Elution was performing using D-PBS pH7.4 (ThermoFisher Scientific) containing 0.1% sodium azide. The fast-moving band containing casein-bound fluorophore was collected in a volume of approximately 0.4 ml. Concentration of resultant probe (casein-Alexa647 in PBS-azide) was estimated via spectrophotometry using Beer's law (Implen Nanophotometer, Implen, Inc. Westlake Village, CA). Probe was aliquoted and stored at −20° C. until use.

Assays were performed in 20 ul volumes in 384-well black optical plates (Nunc, Roskilde, DK). Pepstatin dose response curves were used to optimize pepsin/inhibitor concentrations and assay incubation times. Dose response was performed using 0.3-1000 uM unlabeled pepstatin with 100-500 nM pepstatin-Alexa647 probe, 0.003-3U/µl porcine pepsin (Worthington, Lakewood, NJ), and 10-37% dimethyl sulfoxide (HIV protease inhibitor diluent) in 0.1M HCl, pH1+0.01% Tween-20. Reagents were combined (with pepsin added last) in 50% of the final reaction volume for mixing and immediately read on a BioTek Cytation (BioTek Instruments, Winooski, VT) with far-red FP filter cube at excitation/emission of 620/680 nM for five minutes, in at least triplicate. Averaged polarization values of replicate reads were plotted against probe or labeled pepstatin concentrations in GraphPad Prism 8 (La Jolla, CA). Reagent concentrations yielding greatest dynamic range were selected for the assay. The peptic activity assay was optimized similarly using casein-Alexa647 probe in 0.1M HCl, pH1+0.01% Tween-20. Reagents were combined (adding pepsin last) and read immediately at minimal intervals (<2 minutes apart) over 30 minutes. The assay was performed in triplicate and mean polarization value was plotted over time.

HIV protease inhibitors were dissolved in DMSO. Amprenavir, ritonavir, lopinavir, saquinavir mesylate, nelfinavir mesylate hydrate, darunavir ethanolate, indinavir sulfate salt hydrate were obtained from Sigma-Aldrich. Compounds were tested under optimized assay conditions over a range of three logs concentration in triplicate and plotted using GraphPad Prism 8. Half-maximal inhibitory concentration ($IC_{50}$) were calculated from kinetic traces analyzed using an online tool (icekat.herokuapp.com/icekat, Olp 2019[95]). Percent bound and percent activity were calculated by normalization to the measured polarization value without HIV protease inhibitor compound.

Crystallization

Lyophilized porcine pepsin A (Worthington Biochemical Corporation) was dissolved in water at 200 mg/mL. All ligand stock solutions, except for saquinavir mesylate, were prepared as saturated solutions in DMSO in order to dissolve the maximal amount of ligand. The solutions were centrifuged and an appropriate volume of the supernatant was added to the pepsin solution so that final mixture contained 1.6% of the ligand stock by volume. The mixtures were incubated at room temperature for 1 h, centrifuged for 10 min at 31,000 rcf, and the supernatant was used for crystallization experiments. Due to the low solubility of saquinavir, the compound was absent in our initial attempts to determine the structure of the pepsin saquinavir complex. In order to maximize the solubility of saquinavir in the crystallization solution, we tested solutions from the CryoSol screen (Molecular Dimensions) (PMID 28626721). Mixture SM2 consisting of 37.5% v/v dioxane, 25% v/v DMSO, 12.5% v/v ethylene glycol, 12.5% v/v 1,2-propanediol, and 12.5% v/v glycerol allowed us to increase the amount of ligand solution in the co-crystallization mixture without damaging the protein. The saturated solution of saquinavir in SM2 was treated in the same manner as solutions of other ligands except that its amount in the solution with pepsin was increased to 5% by volume.

The initial crystallization condition was identified by screening 200 mg/mL ligand-free porcine pepsin against the Salt RX screen (Hampton Research). Small bipyramid-shaped crystals were obtained in 3.5 M ammonium chloride and 0.1 M sodium acetate trihydrate pH 4.6 after 1 week of incubation at room temperature. These crystals were used to prepare a microseed stock via the method described by Luft and DeTitta (PMID 10216295) that was then used in co-crystallization of pepsin with amprenavir, ritonavir and darunavir. Diffraction quality crystals formed after 2-7 days from hanging drops containing 2 µL of pepsin at concentrations of 180-210 mg/mL and 1 µL of a microseed solution serially diluted 10-100× above a well solution containing 3 M-4 M ammonium chloride and 0.1 M sodium acetate trihydrate pH 4.6. The crystals were shaped as triangular bi-pyramids with dimensions approximately 200×100×100 µm. Crystals were cryoprotected by soaking them in 30% w/v glucose, 5 M ammonium chloride and 0.1 M sodium acetate trihydrate pH 4.6 and then plunging them in liquid nitrogen.

The complex with saquinavir was crystallized in the same manner except that we used 0.1 M acetic acid instead of 0.1 M sodium acetate trihydrate pH 4.6 because this change allowed us to grow large crystals without the need for a microseeding solution. Cryoprotection was accomplished using 30% w/v glucose, 3 M ammonium chloride and 0.1 M acetic acid, followed by plunging in liquid nitrogen. Crystallographic data collection and model refinement statistics are provided in Table 1.

TABLE 1

Crystallographic data collection and model refinement statistics.

| PDB Entry | Pepsin•Amprenavir 6XCT | Pepsin•Ritonavir 6XCY | Pepsin•Darunavir 6XD2 | Pepsin•Saquinavir 6XCZ |
|---|---|---|---|---|
| | | Data collection | | |
| Resolution (Å) (last shell)[a] | 53.22-1.99 (2.061-1.99) | 53.17-2.05 (2.123-2.05) | 49.34-1.901 (1.969-1.901) | 53.31-1.89 (1.958-1.89) |
| Space group | P 65 2 2 | P 65 2 2 | P 65 2 2 | P 65 2 2 |
| a, b, c (Å) | 66.1298, 66.1298, 288.082 | 66.16, 66.16, 285.522 | 66.245, 66.245, 290.049 | 66.39, 66.39, 284.572 |
| $\alpha, \beta, \gamma$ (°) | 90, 90, 120 | 90, 90, 120 | 90, 90, 120 | 90, 90, 120 |
| $R_{merge}$[a] | 0.01035 (0.02856) | 0.04473 (0.2287) | 0.08851 (0.2532) | 0.02623 (0.2343) |
| $R_{meas}$[a] | 0.01463 (0.04039) | 0.06326 (0.3234) | 0.09249 (0.2648) | 0.03709 (0.3314) |
| $R_{pim}$[a] | 0.01035 (0.02856) | 0.04473 (0.2287) | 0.02635 (0.07655) | 0.02623 (0.2343) |
| $CC_{1/2}$[a] | 1 (0.996) | 0.995 (0.732) | 0.995 (0.981) | 0.998 (0.781) |
| No. of unique reflections[a] | 26764 (2580) | 23751 (2360) | 30916 (2998) | 30079 (2948) |
| Completeness (%)[a] | 99.80 (99.35) | 97.28 (99.28) | 99.85 (99.90) | 97.01 (97.88) |
| Multiplicity[a] | 2.0 (2.0) | 1.8 (1.8) | 12.0 (11.8) | 1.8 (1.9) |
| $\langle I/\sigma(I) \rangle$[a] | 33.78 (19.79) | 6.71 (2.47) | 35.71 (10.34) | 8.41 (1.81) |
| | | Model Refinement | | |
| Reflections used in refinement[a] | 26760 (2580) | 23747 (2360) | 30888 (2995) | 30072 (2948) |
| Reflections used for $R_{free}$[a] | 1312 (114) | 1214 (116) | 1574 (125) | 1544 (145) |
| $R_{cryst}$ ($R_{free}$)[a] | 0.1907 (0.1906) | 0.2173 (0.2586) | 0.1997 (0.1887) | 0.2260 (0.2941) |
| Wilson B-factor (Å²) | 17.73 | 34.87 | 18.85 | 27.03 |
| Average B factor (Å²) | 20.66 | 45.32 | 22.66 | 38.38 |
| Protein atoms | 19.62 | 44.98 | 21.61 | 37.97 |
| Ligand atoms | 24.29 | 71.10 | 26.63 | 59.65 |
| Solvent | 27.46 | 40.81 | 29.22 | 38.11 |
| | | Root-mean-square (RMS) deviations | | |
| Bond lengths (Å) | 0.009 | 0.011 | 0.013 | 0.015 |
| Bond angles (°) | 0.77 | 1.48 | 1.02 | 1.68 |
| Coordinate error (Å)[b] | 0.14 | 0.12 | 0.15 | 0.10 |
| | | Ramachandran statistics | | |
| Favored/allowed/outliers (%) | 99.37/0.32/0.32 | 97.82/1.87/0.31 | 99.37/0.32/0.32 | 98.13/1.56/0.31 |
| Rotamer outliers (%) | 0.00 | 1.82 | 0.00 | 2.92 |
| Clashscore | 0.85 | 2.72 | 2.33 | 2.93 |

[a]Values in parentheses apply to the high-resolution shell indicated in the resolution row
[b]Maximum-likelihood based estimates of coordinate error Data Collection Pepsin·APV: A 1.9 Å diffraction data set was collected at the Life Sciences Collaborative Access Team beamline (LS-CAT) 21-ID-F at the Advanced Photon Source (APS) equipped with a MAR 300 CCD detector using a 50×50 μm beam at a wavelength of 0.97872 Å. A total of 262 frames were collected from φ=0 to 130.5° with an oscillation range of 0.5° and detector distance of 250 mm. Exposure time was 0.5 seconds. Diffraction data were indexed, integrated and scaled using MOSFLM (PMID 21460445).

Pepsin·RTV: A 2.1 Å diffraction data set was collected at LS-CAT beamline 21-ID-D equipped with a Dectris Eiger 9M detector using a 50×50 μm beam at a wavelength of 1.12721 Å. A total of 900 "frames" were collected from φ=0 to 180°, while oscillating at a rate of 1°/sec and slicing of 5 images/°. The crystal-to-detector distance was 160 mm. Diffraction data were indexed, integrated and scaled using MOSFLM (PMID 21460445).

Pepsin·DRV: A 1.9 Å diffraction data set was collected at LS-CAT beamline 21-ID-G equipped with a MAR 300 CCD detector using a 50×50 μm beam at a wavelength of 0.97856 Å. A total of 900 frames were collected from φ=0 to 180° with an oscillation range of 0.2° and detector distance of 260 mm. Exposure time was 0.3 seconds. Diffraction data were indexed, integrated and scaled using HKL2000 (PMID 27754618).

Pepsin·SQV: A 1.9 Å Diffraction data set was collected at LS-CAT beamline 21-ID-F equipped with a MAR 300 CCD detector using a 50×50 μm beam at a wavelength of 0.97872 Å. A total of 400 frames were collected from φ=20 to 100° with an oscillation range of 0.2° and detector distance of 200 mm. Exposure time was 0.5 seconds. Diffraction data were indexed, integrated and scaled using MOSFLM (PMID 21460445).

Model Refinement

Initial phases were obtained by molecular replacement in PHASER (PMID 19461840). The unliganded structure of porcine pepsin (PDB ID 4PEP) with B factors reset to 20.00 Å and solvent molecules removed was used as the search model. Model refinement was performed using phenix.refine from the PHENIX (PMID 20124702; PMID 21041930) suite and COOT (PMID 20383002; PMID 15572765). The geometric restraints for the compounds were obtained from CCP4 monomer library (PMID 28177307). The models were validated using the MolProbity (PMID 20057044) tools as implemented in the PHENIX suite. Models of ritonavir and saquinavir complexes were additionally optimized using PDB-REDO server (PMID 25075342) prior to deposition.

In Vivo Mouse Model

An in vivo mouse model of direct application of pepsin, to mimic laryngeal exposure during LPR, and treatment with select HIV protease inhibitors by either gavage (oral systemic delivery) or aerosolized delivery (inhaled local delivery) was used. Commercial formulations of Lexiva and Prezista were used in groups receiving oral/systemic treatment and equivalent doses of pure active drug, fosamprenavir (Anant Pharmaceuticals Pvt. Ltd., Ambernath, Maharashtra India) and darunavir (Ambeed, Inc., Arlington Heights, IL), were aerosolized for inhalation treatment; both referred to by the generic name throughout. Each group contained 3 mice. Six-week-old female Jackson A/J mice (Jackson Laboratory, Bar Harbor, ME), weighed one day after arrival, then weekly, on Mondays thereafter. There was no significant weight difference among the test groups. Mice were housed 3 per cage, fed D-62 powdered Wattenberg diet at 2 g/mouse/day upon arrival, and until terminated (Caicedo-Granado et al., 2014).

In the first two experiments examining the effect of: 1) pH 7 and pH 4+/–pepsin and, 2) oral fosamprenavir treatment, mice were anesthetized with Avertin (2,2,2-Tribromoethanol) at 225 to 240 mg/kg IP injection. Avertin was the preferred anesthetic for the brief application time needed as it has a rapid induction, produces a short surgical anesthesia, and has a rapid recovery. In the third experiment comparing oral and inhalation treatment with fosamprenavir and darunavir, IACUC requested a change in anesthetic due to the mice requiring consecutive days of anesthesia. For this experiment, isoflurane inhalation was used. The isoflurane, self-scavenging machine, was operated at 3% isoflurane with 2.5 liters of air per minute (LPM). The induction chamber was charged for 3-5 minutes prior to the mice being anesthetized. Mice were placed in the induction chamber for 3-5 minutes prior to any wounding or administrations. Anesthesia records were kept according to IACUC policy.

Anesthetized mice were placed on a slanted board slanted under an operating microscope (Caicedo-Granado et al., 2014). Animals secured by a copper wire attached to the board from which the mice were suspended by their upper teeth. This caused the lower jaw to fall open naturally, exposing the larynx and permitting visualization with a Zeiss microscope at 6× magnification. The wounding procedure was performed using a blunted needle bent at 135°. Under direct visualization, the subglottis, glottis, and supraglottis regions were superficially scratched interiorly from distal to proximal as the needle was pulled out gently, making a mild abrasion. This procedure was performed twice, with one week between woundings.

To examine the effect pepsin at acid and nonacid pH, animals were treated for 2 weeks with laryngeal instillation of pepsin (20 µL at 0.3 mg/ml, pH 7.0 or pH 4.0) at 24, 48, and 72 h post wounding procedure. During weeks 3 and 4, animals were treated with laryngeal instillation for 3 days per week. Mice were sacrificed and samples collected on Friday of the fourth week.

To examine the efficacy of HIV protease inhibitors and to compare oral and inhalation treatment, the groups were as follows: control/solvent, control/pepsin, Lexiva gavage/solvent, Lexiva gavage/pepsin, Prezista gavage/solvent, Prezista gavage/pepsin, darunavir aerosol/solvent, darunavir aerosol/pepsin, fosamprenavir aerosol/solvent and fosamprenavir aerosol/pepsin. The twelve mice in the aerosol groups were condition in the nose-only exposure chamber (Intox) on three separate days by exposure to dry air for 10 min. Beginning the Monday (day 1) of the next week, aerosols and gavages were performed on the mice Monday through Friday (5 exposures). The aerosols and gavages continued Monday-Friday for three more weeks, with the final week consisting of 4 total exposure days, Monday-Thursday, (19 total) with the mice sacrificed and tissues harvested on Friday. Each mouse received two woundings and 12 solvent or pepsin administrations. Wounding and intratracheal administrations were concurrent with the aerosol and gavage treatments. The first wounding was performed on day 2, followed by solvent or pepsin administrations on days 3, 4, and 5. The second wounding was performed on day 8, followed by solvent or pepsin administrations on days 9, 10, and 11. In weeks 3 and 4, mice received solvent or pepsin administrations on days 16, 17, and 18 and days 23, 24, and 25. Day 26 was sacrifice and tissue harvest.

Aerosol generation procedure was similar to that described earlier (Xie et al., 2010). A 10 mL suspension of drug in ethanol was placed in the baffle, such that the concentration would remain constant at the equilibrium solubility. Droplets of ethanol containing dissolve drug were generated by an ultrasonic atomizer (nominal frequency 1.7 MHz) entrained by air at a flow rate of 0.5 LPM with a custom-built glass baffle (University of Minnesota, Department of Chemistry Glass Shop). The aerosol cloud was then passed through a cylindrical drying column containing an annular ring of charcoal. The ethanol is removed and the emanating dry aerosol particles of pure drug were then directed into the exposure chamber.

The mass deposited on the filters in a fixed collection time was measured gravimetrically, and with the collection time, allowed calculation of the total output rate (mg/min). The aerosol concentration (mass/volume of air) was calculated by dividing the total output rate by the air flow rate (0.5 LPM).

The inhaled mass of drug (Minh) for each mouse was calculated as follows:

$$M\text{inh}=[\text{Aerosol}]*RMV*t$$

where [Aerosol] is the aerosol concentration of drug, RMV is the respiratory minute volume of the mice (0.025 L/min), and t is the time of aerosol exposure. The actual mass deposited in the mouse was not determined, but is expected to be only 10% of the inhaled mass, which is the deposition fraction in mice of aerosol particles with a size at 1 µm.

Notably, for translation into humans, we will re-formulate to a larger particle size (e.g. about 8 µm to 12 µm) and take advantage of having humans inhale to maximize particle deposition.

Aerosolization of HIV Protease Inhibitors

Aerosol generation will be performed as previously described (Xie et al. J Pharm Sci. (2010) 99(11):4658-68). Briefly, droplets will be generated by an ultrasonic atomizer (nominal frequency 1.7 MHz, purchased from Mainland-Mart.com), entrained by air with a custom-built glass baffle. To achieve the desired particle size distribution and mass deposition, the concentration of the compound of interest in the baffle will range from 0.75-20 mg/ml (i.e., baffle concentration). The baffle volume will be 10 ml, and the run time will be short to minimize changes in the baffle solution concentration, which will be assayed before and after each experiment. The aerosol cloud will then be carried through a drying column, and the resulting dried particles directed into the exposure chamber.

To determine the aerosol concentration, the mass deposited on the filters will be measured by absorption of extracted filters. The total output rate will be calculated from the total output (filter) and the collection time. The aerosol concentration (mass/volume of air) will be calculated by dividing the total output rate by the airflow rate, and the liquid output rate will be calculated by dividing the aerosol concentration by the concentration of iron in the baffle. The aerosol particle size distributions will be determined with a low flow rate cascade impactor (model 1403, In-Tox Products, Moriarty, New Mexico). Collections will be performed at the point just before the exposure chamber. The mass median aerodynamic diameter (MMAD) and associated geometric standard deviation (GSD) will be calculated from linear regression of an X-Y probability plot of the cumulative undersized mass as a function of the logarithm of the cutoff diameter using Kaleida-Graph (Synergy Software, Reading, PA). The values will be based on the pooling of three independent measurements.

The mass of inhaled fluorescent aerosol (Minh) for each mouse will be calculated as follows:

$$M\text{inh}=[\text{Aerosol}]*\text{RMV}*t$$

where [Aerosol] is the aerosol concentration of fluorescein, RMV is the respiratory minute volume of the mice (0.024 L/min, based on Guyton's formula 22), and t is the time of aerosol exposure. The deposition fraction of fluorescent aerosol within the airway will be calculated as the ratio of assayed tissue mass and the inhaled mass.

Notably, for translation into humans, we will re-formulate to a larger particle size (e.g. about 8 μm to 12 μm) and take advantage of having humans inhale to maximize particle deposition.

Results

Identification of Pepsin-Inhibiting Drug Candidates

Our team developed and optimized two high-throughput screening (HTS) assays to identify compounds that are specific and sensitive inhibitors of pepsin (FIG. 1). The first assay is a binding assay that measures the ability of a compound to compete with fluorescently labeled pepstatin for its binding site on pepsin. The second assay is a peptic activity assay that uses fluorescently labeled casein as an enzymatic substrate. The specificity of these assays was confirmed using three protease enzymes that are similar to pepsin: cathepsin D, trypsin, and renin. The optimal assay conditions (i.e., those yielding the maximal dynamic range in dose response curves) for the competitive binding assay were as follows: 100 nM pepstatin-Alexa647, 0.03U/ul pepsin, 37.5% DMSO, 20 ul reaction, and the optimal assay conditions for the peptic activity assay were: 200 nM casein-Alexa647, 0.01 U/μL pepsin, 5% DMSO, 20 μL reaction.

Figure 2:
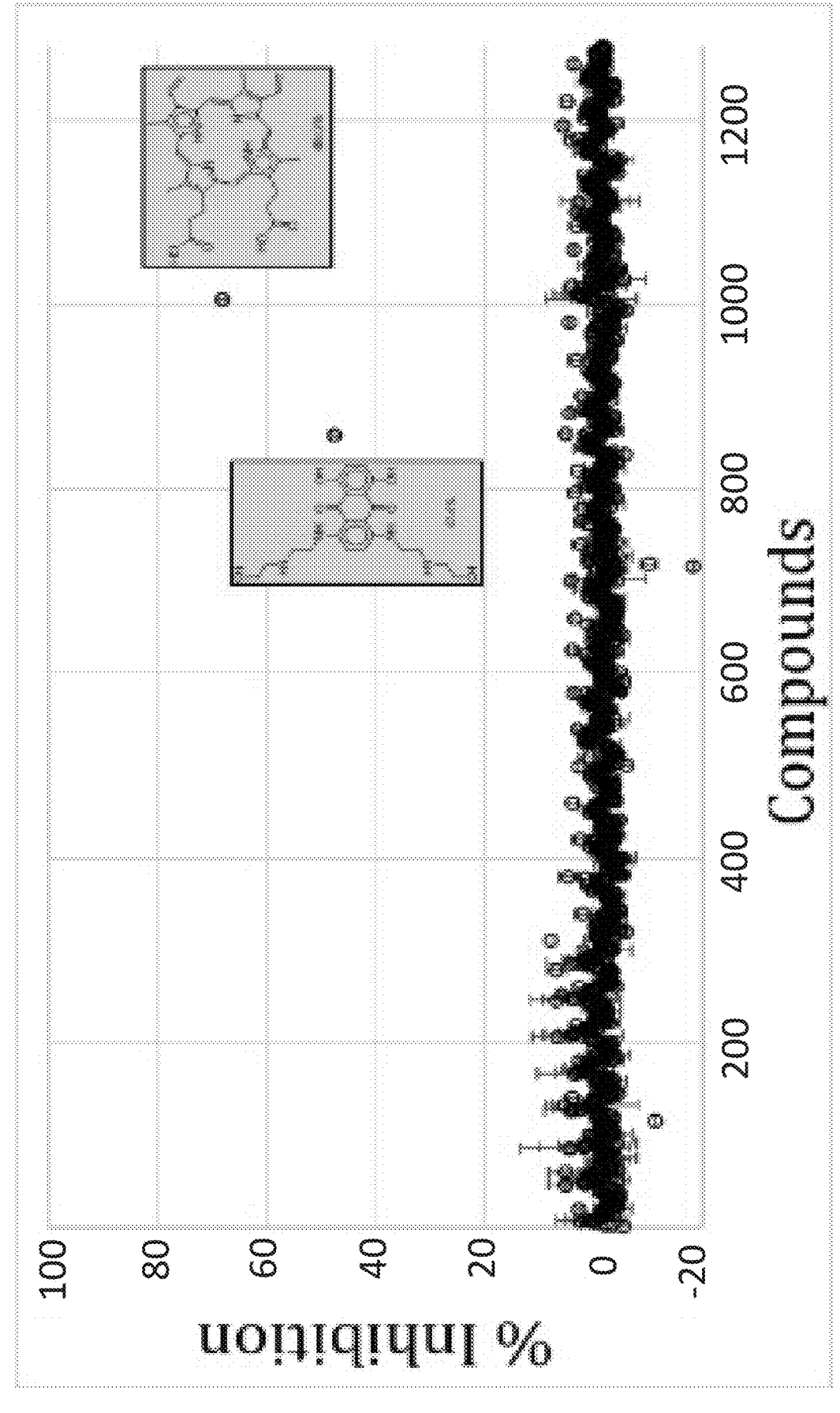
FIG. 2 shows the percent inhibition of pepsin produced by a library of pharmacologically active compounds that was screened using the binding assay.

FIG. 2 shows an example of one of the libraries that was screened with the binding assay. This library contains over 1300 compounds, of which only two showed significant binding, highlighting the specificity of our HTS assay system to determine pepsin inhibition. Ten commercially available HIV protease inhibitors were tested in our binding and enzymatic assays, four of which showed inhibition of pepsin, namely amprenavir, darunavir, ritonavir, and saquinavir (FIG. 3). Under optimized assay conditions, four of the seven HIV protease inhibitors showed both competitive binding to pepsin (FIG. 3A) and inhibition of pepsin activity (FIG. 3B). These were amprenavir, darunavir, ritonavir, and saquinavir. The $IC_{50}$ values of the binding are given in FIG. 3. The in vitro activity of these four HIV protease inhibitors against pepsin provide the foundational support to examine their use for the treatment of LPR.

For in vivo testing, the inventors selected the most promising of these pepsin-inhibiting drugs. Both fosamprenavir and darunavir are considered good candidates for clinical trial, however the other pepsin inhibitors are contemplated for use. Saquinavir was also removed from consideration because it is expensive and can cause QT prolongation, heart block, high blood lipids, and liver problems. Amprenavir and ritonavir are less expensive and cause only minimal side effects (e.g., diarrhea, nausea and vomiting). Amprenavir and its prodrug fosamprenavir are deemed promising candidate because it has superior pharmacokinetics and already tested in mice. Further, a prodrug of amprenavir (fosamprenavir) is commercially available.

Ritonavir, saquinavir and darunavir were also found to bind at the active site of pepsin by co-crystallization studies. Amprenavir, ritonavir, and darunavir have minimal side effects such as diarrhea, nausea and vomiting. Amprenavir and ritonavir are less expensive than darunavir. A prodrug of amprenavir, fosamprenavir, has improved oral bioavailability and favorable tolerability profile is commercially available and therefore deemed the best candidate to test in vivo for its potential efficacy to prevent pepsin mediated laryngeal damage/inflammation.

Crystallization

To provide structural data for interpreting the inhibition studies, commercially prepared porcine pepsin (EC 3.4.23.1) was used for crystallization experiments. Repeated attempts to crystallize human pepsin collected from volunteers met with failure likely due to the inherent sample heterogeneity. In evaluating the quality of porcine pepsin crystals, a data set was collected to determine our own pepsin structure in the absence of inhibitors (data not shown). This structure is nearly identical to that determined previously by Cooper et al. (PDB ID 5PEP [2115088]) based on the small value of the root mean square deviation (RMSD) for all Cα atoms of 0.51 Å. Given the high degree of sequence identity (86%), the structure of porcine pepsin is also nearly identical to that of the human enzyme (PDB ID 1PSN [PMID 7663352]), with a RMSD value for all Cα atoms of 0.50 Å. Most of the minor differences in the tertiary structures were localized in the loop comprising residues 277-282, whose RMSD values ranged from 1.6 to 3.6 Å. This loop is not part of the binding cleft but is involved in crystal contacts in both the human and porcine pepsin. The residues lining the active site cleft are highly conserved between the human and porcine enzymes. Of the 17 residues making direct contact with the inhibitors investigated here, only two differ between human and porcine pepsin: T12 and V291, which are methionine and leucine residues, respectively, in the human form. Thus, the porcine enzyme was deemed an acceptable substitute for human pepsin for assessing the structural biology as described below.

The same crystallization conditions that yielded crystals of the unbound porcine pepsin were used to crystallize complexes of the enzyme with each of the four inhibitors: ritonavir (pPEP·RTV; PDB ID 6XCY), amprenavir (pPEP·APV; PDB ID 6XCT), saquinavir (pPEP·SQV; PDB ID 6XCZ), and darunavir (pPEP·DRV; PDB ID 6XD2). All are peptidomimetics that contain chemical moieties to take advantage of the specificity subsites of the protease. In all four complexes, the alcohol of the central phenylalaninol residue, which mimics the transition state of peptide bond cleavage, is bound between the catalytic aspartate residues, D32 and D215. Furthermore, the directionality of binding is the same in each case, with the amino group of the phenylalaninol residue on the prime side of the binding site. This is the same directionality observed for pepstatin binding to human pepsin [PMID 7663352]. Binding of these compounds is dominated by van der Waals contacts between the side chains of the inhibitors and those of the residues lining the binding site and only involves a few hydrogen bonds. For example, in the pPEP·RTV complex (FIG. 9), the β-homophenylalanine side chain is bound in the P1 subsite, making van der Waals contacts with F111, F117, and I120. The phenylalaninol side chain is bound in the P1 subsite, contacting I213, M289, V291, and I300. The thiazole and isopropyl-thiazole groups of RTV do not have any stabilizing interactions with the active site. The electron density for these groups is correspondingly poorly defined, and the B-factors, which reflect the precision of the atomic positions, for these parts of the molecule are extremely high. The structure of the pPEP·SQV complex (FIG. 10) is similar in that the side chain of the phenylalaninol residue is interacting with the P1' subsite, but the two ends of the molecule, the quinoline and decahydroisoquinoline moieties, also have poor density and high B-factors.

Figure 4:
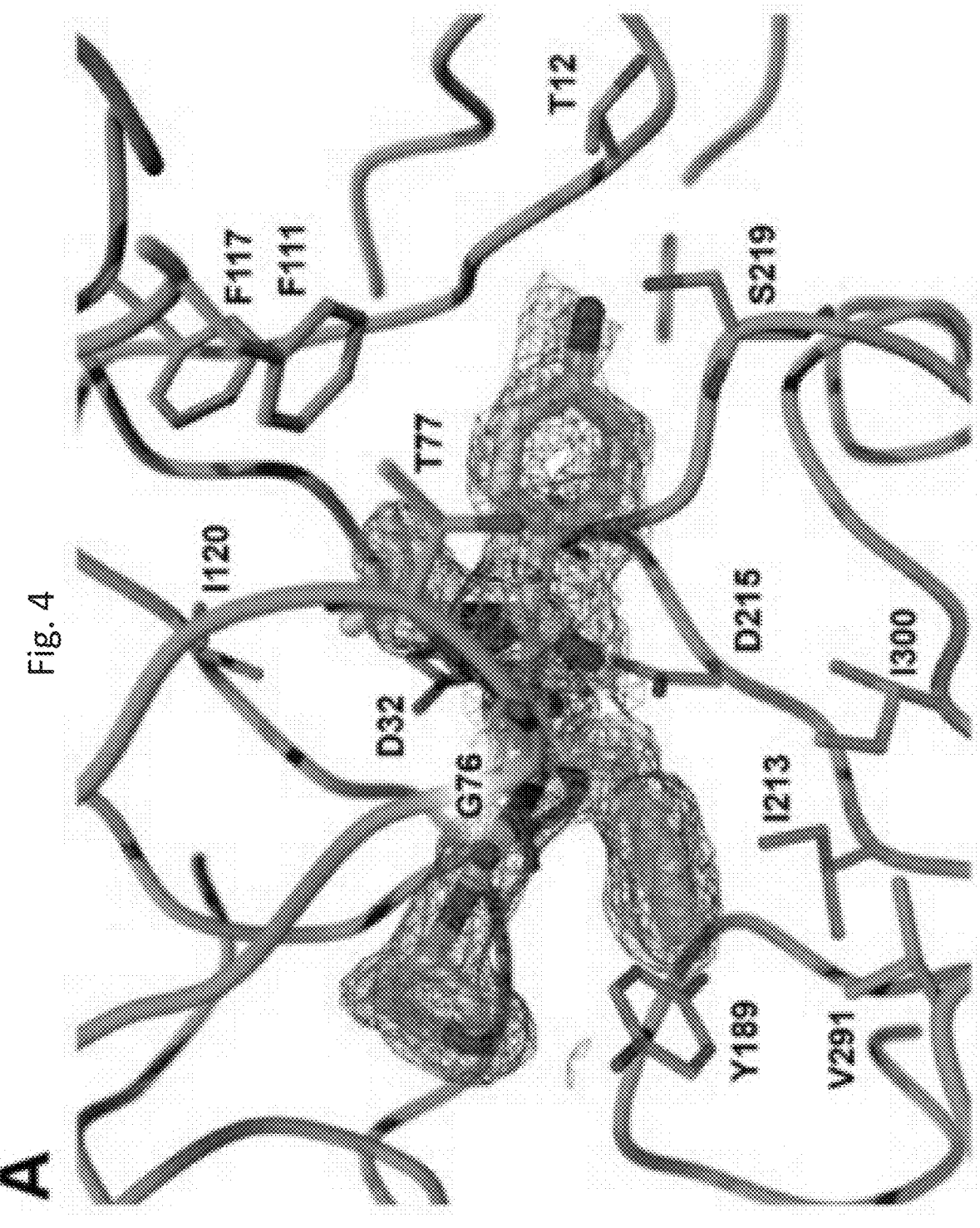
FIG. 4 shows the crystal structure of amprenavir bound to pepsin. (A) The active site of porcine pepsin with amprenavir bound. The $2F_o$-$F_c$ electron density map contoured at $1.0\sigma$ is shown as magenta mesh and the $2F_o$-$F_c$ simulated annealing composite omit map, also contoured at $1.0\sigma$, is shown as green mesh. (B) Schematic view of the active site with amprenavir bound showing potential hydrogen bonding interactions as green, dashed lines. Panels C and D show the structure and enzyme-inhibitor interactions in the active site of pepsin with darunavir bound. Panels A and C were generated using POVSCRIPT and POV-Ray. Panels B and D were created using a combination of MarvinSketch (www. ChemAxon.com) and Adobe Illustrator CC 2020.
Figure 4:
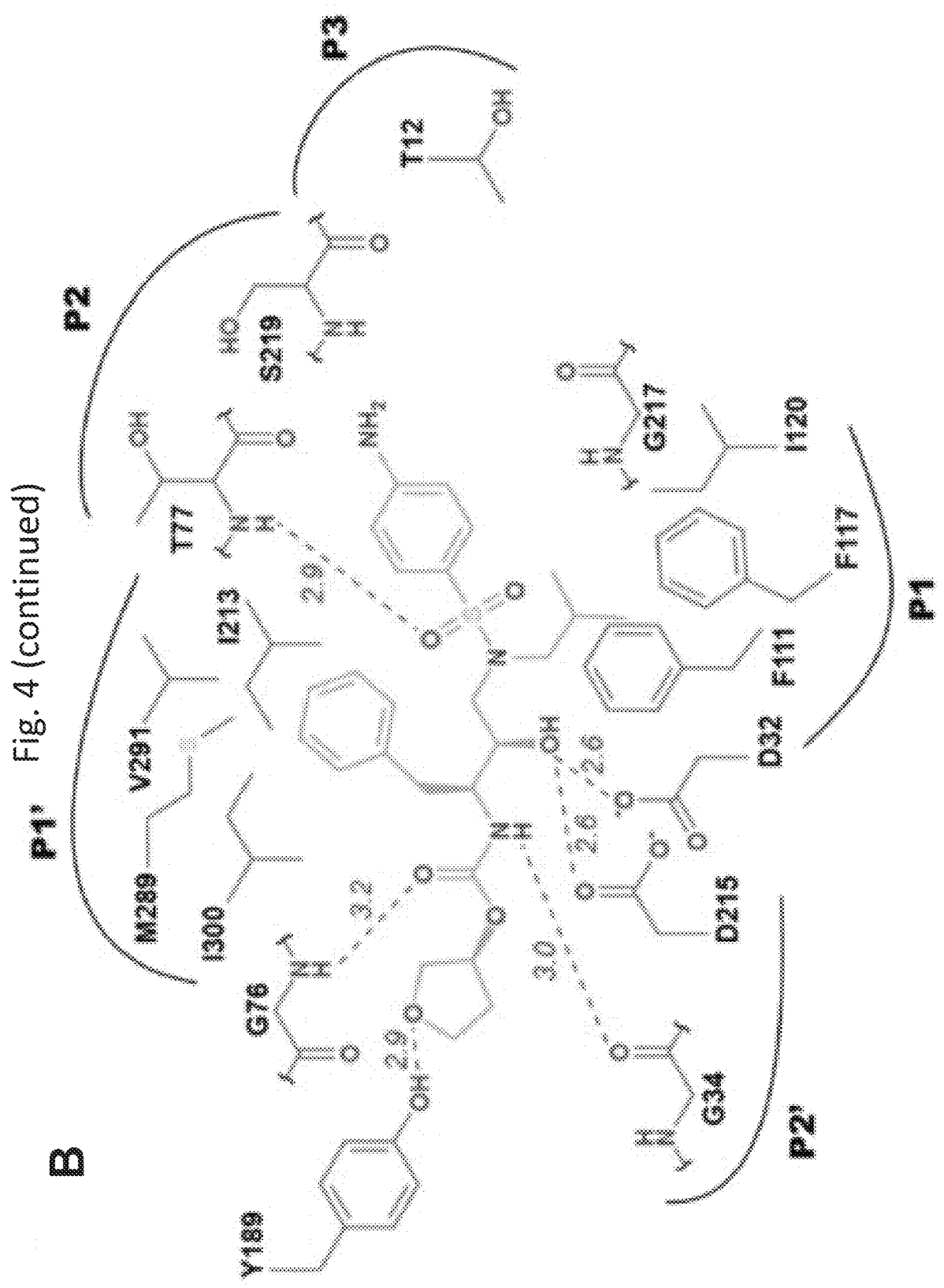
Figure 4:
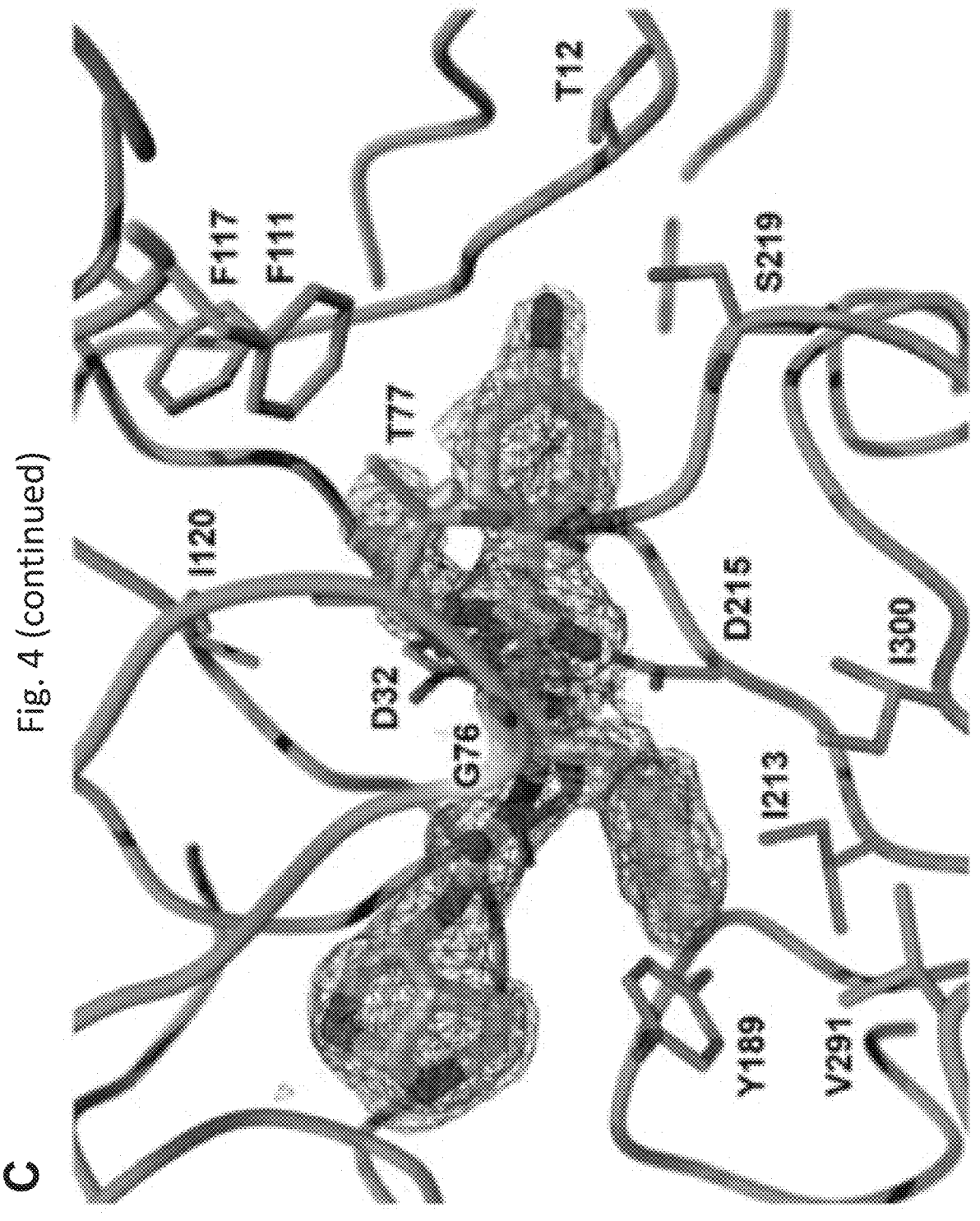
Figure 4:
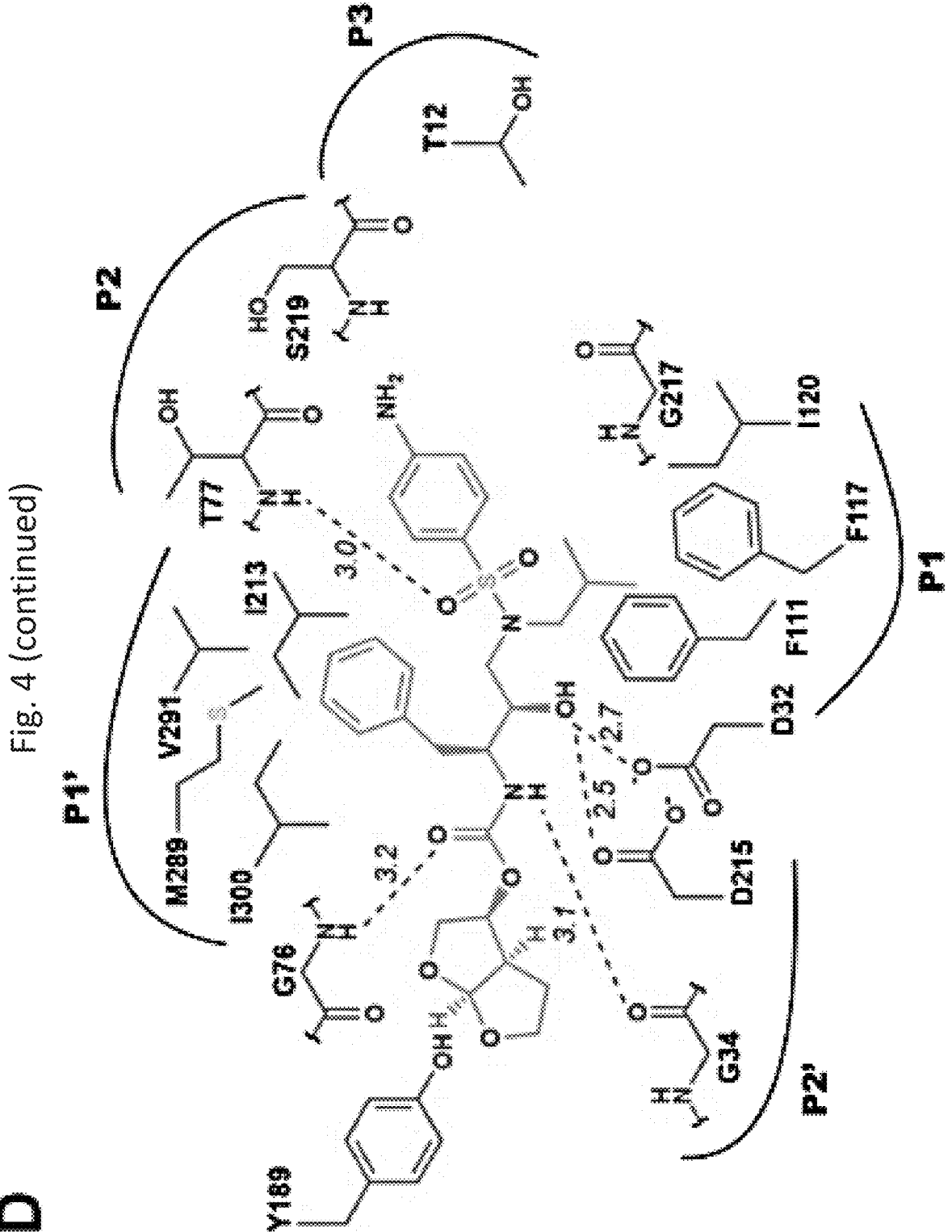

The amprenavir (FIG. 4) and darunavir structures follow the same pattern. The phenylalaninol residues of both inhibitors occupy the P1' site, interacting with I213, M289, V291, and I300. The isobutyl groups, mimicking leucine residues, occupy the P1 site, interacting with F111, F117, and I120. In both amprenavir and darunavir, one of the oxygen atoms of the sulfonamide moiety makes a hydrogen bond with the backbone amide of T77. The aminophenyl groups make no polar contacts with the active site. At the opposite end of the molecules where the two compounds differ, the tetrahydrofuran group of amprenavir forms a hydrogen bond with the phenolic oxygen of Y189. The bis-tetrahydrofuran group of darunavir, however, cannot have this interaction with the active site and is limited to van der Waals contacts with I73, T74, I128, and Y189. It is interesting to note that both amprenavir and darunavir bind in the pepsin active site in the opposite orientation to that seen in their complexes with the HIV protease [PMID: 20695887, PMID: 24785545].

Epidemiological Support for the Use of HIV Protease Inhibitors to Treat LPR

Clinical records were obtained using the Cohort Discovery Tool (CDT) of the Medical College of Wisconsin Clinical Data Warehouse (MCW CDW; PRO #13874). The MCW CDW provided totally de-identified clinical information for each subject, which included patient demographics, ICD coded diagnoses, ICD and CPT coded procedures, laboratory test results, inpatient pharmacy orders, and text with clinical documents including pathology reports. This database was used to determine that of 2062 HIV patients that are taking a HIV protease inhibitor, only five (0.2%) have LPR. Using this data, the inventors discovered that patients taking HIV protease inhibitors have a significantly lower incidence of airway reflux (0.2%) compared to the general population (10-34.4%) (76, 77). However, this query included all HIV protease inhibitors, some of which do not inhibit pepsin. Thus, there was an insufficient number of patients to query each HIV protease inhibitor individually.

Generation of a Mouse Model of LPR

To test the efficacy of HIV protease inhibitors for the treatment of pepsin-mediated laryngeal mucosal damage and inflammation, a novel mouse model was established. There is currently no perfect animal model for LPR, and proximal reflux into the laryngopharynx is not consistent in surgical models. Accordingly, an established mouse model (78) was modified using a wounding procedure for use in this study. Briefly, after anesthetization, the larynx was exposed with a suspension apparatus and visualized with a Zeiss microscope at 6× magnification. Anesthetized animals were placed in suspension and pepsin was applied topically in volumes of 20 ul. These mice showed pepsin-mediated airway epithelial damage at both pH 4 and pH 7 (FIG. 5), demonstrating the ability of this treatment to mimic the effects of LPR. FIG. 5 further shows that pepsin causes laryngeal epithelial damage at pH7 in vivo, as in non-acid laryngopharyngeal reflux.

This mouse model was the first to test the ability of the HIV protease inhibitors fosamprenavir (brand name: Lexiva) and darunavir (brand name: Prezista) to alleviate laryngeal damage. Oral administration of fosamprenavir, as Lexiva 20 mg/kg/day, equivalent to the dose used to treat HIV in humans, prevented pepsin-mediated laryngeal injury (defined as multi-layered, reactive epithelia and cell apoptosis) in this in vivo mouse model (FIG. 7). In contrast, oral administration of darunavir, as Prezista 8.6 mg/kg/day, also the human equivalent dose, did not abrogate pepsin mediated laryngeal injury (FIG. 7H). Fosamprenavir was administered by inhalation at a dose of 1 mg/kg/d prevented pepsin mediated laryngeal injury (FIG. 7F). Significantly, darunavir administered as an aerosol at a dose of 12 mg/kg/d (FIG. 7J) was also effective in preventing pepsin mediated injury. HIV protease inhibitors will be aerosolization (see Materials and Methods above), and a second group of mice will be given the HIV protease inhibitor via inhalation to determine whether local delivery would be more effective. Specifically, mice that underwent the wounding procedure and pepsin treatment will be assigned to one of four groups: (1) ritonavir by gavage, (2) ritonavir by aerosol, (3) fosamprenavir by gavage, (4) fosamprenavir by aerosol, and will be compared to mice that underwent the wounding procedure but did not receive the pepsin treatment. Hematoxylin and eosin (H&E) stained laryngeal tissue sections were evaluated for inflammation. Specifically, the epithelial thickness (i.e., 0, 1-2, 3-4, 5+ cells and the thickness in microns) and the presence of neutrophil infiltrate, keratinization, and necrosis was recorded. Specifically, slides were cut 4 microns thick on a microtome and stained with hematoxylin and eosin (H&E) using an automated stainer. Slides were reviewed by a board-certified pathologist. The upper airway epithelium was identified based upon histological morphology. The effect of pepsin-mediated damage was determined by cytological alterations including increased nuclear to cytoplasmic ratio, multilayered epithelium, loss of cilia, individual cell apoptosis, and inflammatory infiltrates.

FIG. 6 further demonstrates that Lexiva treatment, equivalent to the current FDA approved dose and formulation for HIV, prevents pepsin mediated laryngeal injury in our in vivo mouse model. Thus, Lexiva could be used for the treatment of laryngopharyngeal reflux.

This study was approved by the University of Minnesota's Institutional Care and Use Committee. Thirty, 6 week old female A/J mice were purchased from Jackson Labs, Bar Harbor, ME for use in this study. Mice were housed three per cage, under standard conditions. Mice were provided with ad libitum access to water and D-62 modified pellets, a standard rodent diet purchased from Research Diets, New Brunswick, NJ Mice were weighed the day after arrival, and weekly, thereafter. The week after arrival, mice were randomized by weight and divided into experimental groups. There was no significant weight difference among the test groups.

The groups contained 3 mice each and were designated as follows: control/solvent, control/pepsin, Lexiva gavage/solvent, Lexiva gavage/pepsin, Prezista gavage/solvent, Prezista gavage/pepsin, darunavir aerosol/solvent, darunavir aerosol/pepsin, fosamprenavir aerosol/solvent and fosamprenavir aerosol/pepsin. This same week, the 12 mice designated as aerosols were trained to the aerosol exposure machine on three separate days, for ten minutes each, each time. Beginning the Monday (day 1) of the next week, aerosols and gavages were performed on the mice Monday through Friday (5 exposures). The aerosols and gavages continued Monday-Friday for three more weeks, with the final week consisting of 4 total exposure days, Monday-Thursday, (19 total) with the mice sacrificed and tissues harvested on Friday. Each mouse received two woundings and 12 solvent or pepsin administrations. Wounding and intratracheal administrations were concurrent with the aerosol and gavage treatments. The first wounding was performed on day 2, followed by solvent or pepsin administrations on days 3,4,5. The second wounding was performed on day 8, followed by solvent or pepsin administrations on days 9,10,11. In weeks 3 and 4, mice received solvent or pepsin administrations on days 16,17,18 and days 23,24,25. Day 26 was sacrifice and tissue harvest.

All aerosol training or experimental exposures were 10 minute duration, per mouse. The training was identical to the experimental exposures, completed with air only. Once aerosol exposures begin, darunavir or fosamprenavir was nebulized in the air stream. For this experiment each aerosol set had a dedicated nebulizer and mouse exposure tubes. On day 1, darunavir aerosol was first, followed by fosamprenavir. Day 2, fosamprenavir was first, followed by darunavir. Switching daily, this cycle was continued for the duration of the exposures. The nose cones of the exposure chamber were wiped clean with 70% ethanol and dried each day, between exposures, and the dedicated exposure tubes were replaced to prevent cross contamination. Aerosols and gavages were completed daily on the mice prior to any wounding or solvent or pepsin administrations. Solvent was PBS pH7. Pepsin was diluted in PBS pH7.0. The concentration of pepsin was 0.3 mg/mL. Solvent and pepsin administration volume was 30 ul, delivered with a Hamilton syringe and the custom dispensing needle for intratracheal administrations.

This study was performed identically to our previously published work using this intratracheal procedure with the exception of the anesthetic used. Previously, we used injectable Avertin anesthetic, however the IACUC requested we change anesthetic due to the mice requiring consecutive days of anesthesia. For this study we used Isoflurane inhalation for the mice. The Isoflurane machine is a self-scavenging machine rented from the University Research Animal Resources. The Isoflurane machine was operated at 3% Isoflurane with 2.5 litres of air per minute. The induction chamber was charged for 3-5 minutes prior to the mice being anesthetized. Mice were in the induction chamber for 3-5 minutes prior to any wounding or administrations. Anesthesia records were kept according to IACUC policy.

All gavages began on day 1. Lexiva gavage volume was 0.2 mL. Prezista gavage volume was 0.5 mL. Each oral medication had a dedicated gavage tip. Each oral medication was shaken for 1 minute daily before volumes were drawn from the bottles. Each dose was checked for accuracy and bubbles, prior to administration. Mice receiving oral gavage doses received a total of 19 doses each.

Lexiva and Prezista both prevent pepsin-mediated laryngeal injury when given by aerosol (FIG. 7). A) Solvent control: single layer of respiratory epithelium with no reactive changes. B) Pepsin control: multi-layered epithelium and individual cell apoptosis (arrows): i) Higher magnification of multi-layered epithelium and ii) Higher magnification of cell apoptosis. C) Fosamprenavir gavage: normal histology in the solvent group. [This tissue section is more proximal than the others, almost at the oropharynx and thus some transitional-type epithelium can be seen]. D) Fosamprenavir gavage: normal histology in the pepsin group. E) Fosamprenavir aerosol: normal histology in the solvent group. F) Fosamprenavir aerosol: normal histology in the pepsin group. G) Darunavir gavage: mild reactive epithelia in the solvent group, but less than pepsin control. H) Darunavir gavage: mild reactive epithelia in the pepsin group but less than pepsin control. I) Darunavir aerosol: normal histology in the solvent group. J) Darunavir aerosol: normal histology in the pepsin group. A-J are 20× magnification with scale bar=50 μm. Bi and Bii are 40× magnification with scale bar=20 μm.

FIG. 7 suggests that oral delivery of Lexiva, but not Prezista, prevents pepsin mediated laryngeal injury at the equivalent FDA approved dose for HIV. Inhalation delivery of both Lexiva and Prezista prevents pepsin mediated laryngeal injury in vivo. Inhalation treatment better maintained normal laryngeal histology than oral treatment during pepsin challenge experiments. Local, inhalation delivery will allow reduction in the amount of drug given to the patient as opposed to oral delivery where high doses are needed to produce therapeutically effective drug levels in the laryngopharynx, limiting side effects. This may prove particularly beneficial for these drugs since the main side effects are GI-related. Thus, local, inhalation (nasal/oral spray) would have greater efficacy and be more efficient for the treatment of laryngopharyngeal reflux.

Discussion

For the past two decades, treatment of LPR has focused on suppressing gastric acid production. With the introduction of MII-pH technology, it is now known that LPR is commonly nonacidic and nonacid proximal events are associated with throat symptoms and findings on laryngeal fiberoptic examination (Sharma and Castell, 2009; Tamhankar et al., 2004; Tutuian et al., 2006; Tutuian et al., 2008; Iqbal et al., 2008; Mainie et al., 2006; Klimara et al., 2020; Zhang et al., 2017; Falk et al., 2017; Sidwa et al., 2017; Lechien et al., 2019; 2020). These findings sparked investigations into the other non-acidic components of gastric refluxate. In vitro studies revealed that both pepsin and bile can cause laryngeal inflammation at nonacid pH. Although in vitro studies report bile induced mucosal damage at nonacid pH, it has been argued that "there is no evidence that the same mechanism occurs in the human larynx" (Campagnolo et al., 2014). In vitro exposure to bile acids causes cell membrane 'blebbing' (Hopwood et al., 1981), but to our knowledge this has never been reported in laryngeal mucosa from patients with LPR. Perhaps the concentration of bile reaching the proximal laryngopharynx is insufficient to cause cell membrane damage. The concentrations of bile salts and acids used in previous in vitro studies ranged from 5 to 50 mM. The physiological bile acid/salt content in gastric refluxate reaching the laryngopharynx is expected to be several orders of magnitude lower and range from 10 to 100 μM (Ali et al., 2013). This low concentration has not been shown to cause laryngeal damage. It should also be noted that the unconjugated bile acids that cause damage at higher pH, consistent with the environment of the laryngopharynx, are rarely found in gastric refluxate (Ali et al., 2013; Pearson et al., 2011).

In contrast, pepsin is present in all refluxate (Samuels and Johnston, 2010). Moreover, it is frequently detected in airway tissue and secretions from patients with LPR but absent in MII-pH-confirmed reflux-free control subjects. As such, gastrin may be predictive of reflux-attributed symptoms and disease (Klimara et al., 2019; 2020; Bardhan et al., 2012; Samuels and Johnston, 2009; 2010; Johnston et al., 2009; 2010; 2018; Zalvan et al., 2017; Lechien et al., 2020; Calvo-Henriquez et al., 2017; Weitzendorfer et al., 2019). Pepsin-mediated damage and inflammatory changes in vitro are consistent with that observed in LPR patients (Axford et al., 2001; Johnston et al., 2003; 2004; Gill et al., 2005). Compelling evidence from multiple groups (Bardhan et al., 2012; Niu et al., 2020; Martinucci et al., 2013) highlights a major role for pepsin (independent of gastric acid) in reflux-attributed laryngeal symptoms and findings refractory to PPI therapy. The data presented herein provide additional support that a drug, which specifically targets pepsin, will be therapeutically efficacious.

It should be noted that pepstatin, a commercially available potent inhibitor of pepsin, has poor water-solubility and poor pharmacokinetic properties and therefore would make a poor in vivo candidate. Thus, preclinical evaluations of other pepsin inhibitors to document efficacy were performed.

Given the pepsin binding in the four crystal structures (FIGS. 9, S1 and S2), it is difficult to rationalize the IC50 values observed. Aside from the interactions of the alcohol groups with the catalytic aspartic acid residues, and the hydrogen bonding interactions that amprenavir and saquinavir make with Y189, all polar contacts occur with the main chain. Binding is thus predominantly stabilized by van der Waals contacts. As a whole, this set of crystal structures, together with biochemical data from inhibition assays, suggests that it will be difficult to rationally design inhibitors of pepsin. The strategy to test existing inhibitors of other aspartic proteases was therefore deemed the most direct route to identify a potent inhibitor of pepsin activity for treatment of LPR.

Select HIV protease inhibitors were found to bind to the active site of pepsin and inhibit the enzyme. HIV protease inhibitors target a foreign virus, and thus the therapeutic activity is not directly related to any possible pharmacologic effect in humans. As such, HIV protease inhibitors are ideal drugs to repurpose as well as allow testing the proof-of-concept that a pepsin inhibitor will be effective for patients with LPR disease. There are currently ten commercially available HIV protease inhibitors, seven of which were amenable to testing in our assays. Co-crystallization studies with pepsin, competitive binding assays with fluorescently-labeled pepstatin, and enzymatic assay with labeled protein substrate (casein) revealed amprenavir, ritonavir, saquinavir and darunavir bind to and inhibit pepsin with IC50 values in the low micromolar range. Saquinavir is likely to be excluded from clinical trial based on known side effects and interactions (QT prolongation, heart block, high blood lipids and liver problems) and cost. Amprenavir, ritonavir, and darunavir have minimal side effects, such as diarrhea, nausea and vomiting. Amprenavir and ritonavir are less expensive than darunavir, but darunavir had the lowest IC50 for pepsin. A prodrug of amprenavir, fosamprenavir, with improved oral bioavailability and favorable tolerability profile is commercially available. Thus, darunavir and fosamprenavir were deemed lead candidates and subsequently tested in an established in vivo mouse model to assess their efficacy to abrogate pepsin-mediated laryngeal damage and inflammation.

Oral, systemic administration of fosamprenavir, but not darunavir, prevented pepsin mediated laryngeal injury in vivo. However, treatment with both of these HIV protease inhibitors maintained normal laryngeal histology despite pepsin exposure when administered locally by inhalation. Reformulation of these drugs for local inhaled delivery (oral or nasal) would likely be beneficial for the treatment of LPR. Besides the obvious advantage in delivering drug directly to the site of reflux-attributed injury, inhaled delivery also allows reduction in the amount of drug given to the patient as opposed to oral delivery. With the latter approach, high doses are needed to overcome the evident poor oral bioavailability and achieve efficacious drug concentrations in laryngeal tissue, which may pose dose limiting side effects. The latter aspect may prove particularly beneficial for the drugs used here as the main side effects are GI-related.

The current inhalation studies involved optimized delivery to the mouse model with administration of pure drug contained in a relatively small aerosol particles (i.e. 1 μm). For translation from in vivo to clinical application, the drug can be reformulated to optimize inhalation delivery to humans. Here, a larger particle size would be generated to take advantage of the fact that humans can be instructed to take controlled forceful inhalations to maximize particle deposition. A computational fluid dynamics analysis of laryngeal particle deposition revealed an optimal particle size is 9 to 12 microns for deposition in the larynx (unpublished data) which is in good agreement with other studies (Perkins et al., 2018).

Pilot epidemiological data on the incidence of LPR in patients taking a HIV protease inhibitor supports our hypothesis, with only 5/2062 (0.2%) patients taking a HIV protease inhibitor having any report of LPR in their medical record. It should be noted that this included all HIV protease inhibitors, some of which do not inhibit pepsin. Unfortunately, there were insufficient patients to query each HIV protease inhibitor individually. In comparison, the reported incidence of LPR is 10-34.4% of the general population (Kamani et al., 2012; Lowden et al., 2009), similar to the incidence of LPR in matched populations in the MCW CDW. While limited, this epidemiological data supports our hypothesis. Given the aggregate of these data, a 12-week randomized, double-blind, placebo-controlled clinical trial will be performed to assess the efficacy of Lexiva or Prezista for LPR.

Conclusion

Compelling evidence highlights a major role for pepsin (independent of gastric acid) in reflux-attributed laryngeal symptoms and endoscopic findings refractory to PPI therapy. As demonstrated in this Example, fosamprenavir and darunavir, FDA-approved retroviral therapies for HIV/AIDS, bind to and inhibit pepsin, abrogating pepsin-mediated laryngeal inflammation and mucosal damage in vivo. These drugs target a foreign virus so are ideal to repurpose, allowing a clinical trial to assess efficacy for a much-needed medical treatment for patients faster than could be achieved with novel compounds. If the FDA-approved oral formulation resolve symptoms and endoscopic findings of LPR in the clinical trial, reformulation for local inhaled delivery could further improve outcomes and limit side effects.

Example 2: Clinical Trials

In Example 1, the inventors identified an FDA-approved HIV protease inhibitor (fosamprenavir, brand name: Lexiva) that binds to and inhibits pepsin. After the inventors confirmed that this drug abrogates pepsin-mediated laryngeal inflammation and mucosal damage in a mouse model of LPR, they aim to subject it to clinical trials.

Reformulation of HIV protease inhibitors that bind to and inhibit pepsin, for local inhaled delivery (oral or nasal) may be beneficial for the treatment of LPR. Besides the obvious logic of applying topical delivery, inhaled delivery also allows reduction in the amount of drug given to the patient as opposed to oral delivery where high doses are needed to get enough of the drug from the gastrointestinal tract via the bloodstream to laryngeal tissue, limiting side effects.

For translation of our mouse in vivo data into humans, we will re-formulate to a larger particle size and take advantage of having humans inhale to maximize particle deposition. A computational fluid dynamics analysis of laryngeal particle deposition revealed optimal particle size is 9 to 12 microns for deposition in the larynx (unpublished data) which is in good agreement with other studies (Perkins E L, Basu S, Garcia G J M, Buckmire R A, Shah R N, Kimbell J S. Ideal Particle Sizes for Inhaled Steroids Targeting Vocal Granulomas: Preliminary Study Using Computational Fluid Dynamics. Otolaryngol Head Neck Surg. 2018; 158(3):511-9. Epub 2017, Nov. 22. doi: 10.1177/0194599817742126. PubMed PMID: 29160160; PMCID: PMC5832637).

The following example describes the proposed 12-week, randomized, double blind, placebo-controlled clinical trial that the inventors have designed to test the ability of the HIV protease inhibitor Lexiva to resolve the symptoms and endoscopic findings of LPR. Additionally, this study has been designed to assess the predictive value of pepsin protein and activity in saliva for the efficacy of Lexiva treatment. If the results of this trial suggest that Lexiva is able to inactivate pepsin in saliva, the formulation of this drug will be optimized for local delivery by inhaler or nasal spray.

Materials and Methods

Study Design

A prospective, placebo-controlled clinical trial of Lexiva will be performed for 12 weeks in medically refractory patients with clinically diagnosed moderate/severe LPR (Reflux symptom index (RSI)≥20, reflux finding score (RFS)≥11 and combined esophageal multichannel intraluminal impedance and pH monitoring (MII-pH) confirmed laryngeal reflux events). Twelve weeks is a conventional time to determine the efficacy of LPR treatment (1). Routine clinical outcome measures for LPR (RSI and RFS) will be documented pre- and post-treatment with Lexiva or placebo. Saliva will be collected pre- and post-treatment and subjected to both pepsin protein analysis and kinetic activity assay to compare with pre- and post-treatment RSI, RFS, and MII-pH data. A study schema is shown in FIG. 8.

Patients, 18 years of age or older, with a clinical diagnosis of moderate/severe that have been medically refractory for at least 3 months to treatment with proton pump inhibitors (PPI) will be recruited for this study. An experienced clinical research coordinator will obtain informed consent. Patients will be randomized by Froedtert Hospital Pharmacy Investigational Drug Service to receive either Lexiva, given at the same dose and frequency that is FDA-approved for treatment of HIV, or placebo for 12 weeks. Patients will provide a saliva sample for pepsin concentration (ELISA) and activity (kinetic) analyses before they begin Lexiva/placebo treatment. A study incentive of $200 (to be paid at the conclusion of the study) will be provided to encourage patients to follow-up after the 12-week treatment period.

The Sandhill Scientific, ZepHr Sleuth MII device (Z07-2000-B) and the Sandhill Scientific ComforTec Z/pH single use impedance/pH probe (ZAI-BL-56) will be used for this clinical trial to monitor total reflux, esophageal reflux, and LPR. A proximal reflux event will be defined as an episode that reaches both impedance sensors in the hypopharynx.

In addition to RFS, RSI, and MII-pH, measures which are routinely used in clinical practice to assess LPR, a Reflux Symptom Score (RSS) and Reflux Sign Assessment (RSA) were recently developed for the assessment of LPR at time of diagnosis and throughout treatment (81-84) and will also be obtained for this study. The RSS is a patient-administered questionnaire, similar to the RSI. An RSS>13 is considered suggestive of LPR. A reduction in RSS of 20-39.9% is defined as a mild response, 40-59.9% is defined as a moderate response, 60-79.9% is defined as a high response, and >80% or a posttreatment RSS≤13 is defined as a complete therapeutic response (83). The RSA is used to rate the physical findings of LPR, similar to the RFS. An RSA>14 is suggestive of LPR. Notably, both the RSS and RSA assessment have demonstrated high intra- and interrater reliabilities and responsiveness to change (82-84).

Rationale for Choice of Clinical and Research Measures

Patients with moderate/severe confirmed LPR who are refractory to acid suppression therapy and are, therefore, likely benefit from pepsin inhibition will be selected for this study. Patients will be selected based on: confirmation of proximal reflux into the laryngopharynx by MII-pH testing, RSI≥20, RFS≥11, and failed 3-month bid PPI therapy. While RSI≥13 and RFS≥7 is used to diagnose LPR, higher values were chosen for inclusion in this trial to increase the chance of seeing an effect after a 12-week treatment period. In 2001, Belafsky et al. reported a RFS of 11.5 (+/−5.2 SD) at entry, which improved to 9.3 (+/−4.7 SD) at 2 months and to 7.3 (+/−5.5 SD) at 4 months (79). In 2002, the same group reported a RSI of 21.2 (+/−10.7 SD) at entry, which improved to 12.8 (+/−10 SD) after 6 months (80). Thus, a RSI≥20, RFS≥11 is expected to decrease close to normative values after 12-week treatment with Lexiva if a pepsin inhibitor is effective. A 'responder' is defined as a patient who has reduction of ≥6 points in the RSI score after treatment, based on the United States Food and Drug Administration guideline published in 2015 (85). Changes in each item on the RSI questionnaire, relative to the chief complaint upon initial presentation in clinic, will also be assessed.

The selected patients will undergo a MII-pH test and fiberoptic laryngeal exam as per routine clinical care, preventing additional expensive and invasive testing and exams for this research study. Based on our experience, patients with medically refractory LPR are desperately seeking options to resolve their symptoms and improve their quality of life. Furthermore, Lexiva is a FDA approved medication with minimal side effects. Thus, we do not anticipate any problems with enrollment.

The presence and levels of pepsin protein in saliva will be measured by ELISA, and pepsin proteolytic activity will be measured by kinetic assay, as described below. Pepsin is a sensitive and specific biomarker for reflux and its presence in saliva is indicative of proximal airway reflux (30, 34, 86, 88). We hypothesize that its presence in saliva pre-treatment will predict efficacy of Lexiva for decreasing RFS and RSI. Treatment with Lexiva should have no effect on pepsin protein levels, but is expected to inactive the enzyme, preventing pepsin-mediated mucosal damage and inflammation. Loss of peptic activity is expected to correlate with a reduction in RFS and RSI post-treatment. We have previously shown that pepsin in saliva correlates with RSI and proximal reflux events measured by MII-pH (86). Patents with a higher number proximal reflux events and a higher percent time of proximal reflux during the study duration (measured by MII-pH) are therefore expected to exhibit the greatest improvements following treatment with Lexiva.

For saliva sample collection, patients will be asked to cough to clear their throat and spit into an empty tube during their appointment to demonstrate the collection technique. Patients will then take their tube home in a bag containing cold. They will be asked to spit into the tube if they experience a symptom (coughing, throat clearing, post-nasal drip; up to three times) and when they wake and stand the following morning, before eating, drinking, or brushing their teeth. Each patient will cough and spit into their tube a minimum of two times and up to 5 times if they experience symptoms during the 24-hour period following their appointment. We have shown that repeated saliva collection into a single vial increases sensitivity without affecting sensitivity of pepsin detection by ELISA (unpublished data). As was done for other studies, patients will be given a pre-addressed, pre-stamped box to ship their sample to our research laboratory by FedEx Priority. Some groups collect saliva in citric acid as a preservative, but we have shown significant agreement between saliva samples collected in the presence and absence citric acid (87). We have also shown pepsin is stable at room temperature without degradation, and have previously reported pepsin concentration and activity analyses by ELISA and kinetic assay (20, 24, 30, 38, 88, 89).

Pepsin ELISA

The presence and concentration of pepsin in saliva specimens will be determined by noncompetitive indirect sandwich ELISA, as previously described (75, 90). Nunc-ImmunoMaxisorp 96-well flat bottom microtiter plates (Thermo FisherScientific, Inc.) will be coated with affinity purified rabbit anti-Hu3 antibody (3 µg/mL), produced against the N-terminus of mature human pepsin in a volume of 100 µL, 0.2M sodium carbonate buffer, pH 9.6, per well, and incubated at room temperature for 18 to 20 hours. Plates will be washed three times for 2 minutes per wash in PBS, pH 7.4 with 0.1% Tween-20 (PBS-T) and incubated with blocking buffer (SuperBlock PBS Blocking Buffer; Thermo Fisher Scientific, Inc.) for 90 minutes at 37° C. and 200 rpm on an orbital shaker. Plates will be rinsed three times for 2 minutes per wash with shaking in PBS, pH 7.4. Saliva specimens and pepsin standards will be prepared in sample diluent (1% bovine serum albumin [BSA] [Sigma-Aldrich] in PBS). Saliva specimens will be prepared at 1:25 in sample diluent. Sample diluent alone will be used as a blank control. After specimens and standards are applied to the microtiter plate in triplicate in a volume of 100 µL per well, the plate will be incubated for 1 hour at 37° C. and 200 rpm. Samples will be removed from the plate by vacuum aspiration, and wells washed three times for 2 minutes per wash with shaking in PBS-Tween (PBS-T). Captured pepsin will be detected by incubation with goat anti-human pepsin antibody diluted to 26 µg/mL in 1% BSA/PBS-T for 40 minutes at 37° C. and 200 rpm. The plate will be washed three times for 2 minutes per wash in PBS-T and incubated for 40 minutes at 37° C. and 200 rpm with peroxidase-conjugated mouse anti-goat immunoglobulin G (Sigma-Aldrich) diluted 1:30,000 in 1% BSA/PBS-T. Enzymatic color development will be carried out using 1-Step Ultra TMB ELISA (ThermoFisher Scientific). Color development will be stopped by the addition of an equal volume of 1N sulfuric acid and the wells read at 450 nm in the microplate reader (SpectraMax Plus; Molecular Devices, Sunnyvale, CA). Triplicate readings for each standard, specimen, and the blank will be averaged, and the average absorbance at 450 nm (A450) of the blank specimen subtracted from average absorbances of specimens and standards. A standard curve will be plotted using blank-subtracted mean absorbances and concentrations of pepsin standard dilutions. The concentration of pepsin (ng/ml) in saliva samples will be calculated using a best-fit curve model. Samples with an A450 less than two-fold the absorbance the A450 of the blank will be considered negative for pepsin.

Pepsin Activity Assay

The synthetic peptide substrate for pepsin (Lys-Pro-Ala-Glu-Phe-PNP-Arg-Leu-COOH (SEQ ID NO:1), molecular weight=1,052.18; PNP=paranitrophenylalanine) is cleaved specifically by pepsin between Phe-5 and PNP-6. Cleavage will be monitored by decreasing absorbance at 300 nm (20, 24). The rate of hydrolysis of the synthetic peptide substrate (70 µmol/L) by saliva specimens will be measured by kinetic assay at 300 nm. The rate of the first 10% hydrolysis will be calculated for each reaction and a graph of the mean (±SEM) rate (nmol/L per min, n=3) for each specimen plotted. Activity (U/ml, where 1U=pepsin that produces change in A300 of 0.001 per second) will be calculated.

Inclusion Criteria

Clinical diagnosis of LPR

Age≥18 years

RSI≥20

RFS≥11

Documented LPR by MII-pH testing (>1 proximal event)

Failed 3 month bid PPI therapy

Attending laryngology clinic and having flexible laryngoscopy and MII-pH testing per routine clinical care with a minimum of three months between clinic visits (standard practice)

Patients must be deemed able to comply with the saliva sample collection, treatment plan, and follow-up schedule Patients must provide study-specific informed consent prior to study entry Exclusion Criteria Elderly, pregnant (or plan to be) and nursing mothers as Lexiva not recommended for those populations Currently taking a HIV inhibitor History of hepatic impairment Sulfa Allergy Hemophilia Currently being treated with another investigational medical device and/or drug A history of gastric or esophageal surgery GI disease that might interfere symptom questionnaire, e.g. IBD A history of laryngeal or neck surgery including thyroidectomy and laryngomicroscopic surgery Suspected esophageal cancer Nasopharyngeal cancer Previously undergone anti-reflux surgery Polypharmacy (five or more concurrent medications due to comorbidities)

Potential contradictions or known interactions with Lexiva

Anticipated poor understanding or compliance of the study protocol

Data/Efficacy Analyses

REDCap, a secure web platform for online databases and surveys, will be used to record and analyze the data obtained for this study. REDCap provides automated export procedures for seamless data downloads to Excel and common statistical packages (SPSS, SAS, Stata, R), as well as a built-in project calendar, a scheduling module, ad hoc reporting tools, and advanced features, such as branching logic, file uploading, and calculated fields. REDCap will allow record of signed informed consent electronically. The two patient administered questionnaires for this study (RSI and RSS) will be completed by patients electronically on a tablet in the clinic and the data will be saved automatically in REDCap.

Data to be Recorded in REDCap

Age, sex, race

History of smoking (yes/no), current smoker (yes/no)

Alcohol intake (>1 drink/day)

Hypertension (yes/no)

Diabetes mellitus (yes/no)

Psychiatric illness (yes/no)

Duration of symptoms (≥6 months)

Reflux medications, pre and during trial (Proton Pump Inhibitors, H2 receptor antagonists, alginate)

MII-pH data: total number proximal reflux events, percent time of proximal events, percent time proximal events<pH4.0, total number distal reflux events, percent time of distal events, percent time distal events<4.0, DeMeester score Reflux Symptom Index (RSI)

Reflux Finding Score (RFS)

Pepsin protein in saliva—yes/no

Pepsin protein concentration (ng/ml)

Pepsin activity—yes/no

Pepsin activity (U/ml)

Reflux Symptom Score (RSS)

Reflux Sign Assessment (RSA)

Power Analysis

To determine the sample size required for the proposed study, we used means and standard deviations (SD) of RFS and RSI from previous reports (79, 80) and assumed a mean difference of 4.2(6.5) and SD of 6(10) for RFS(RSI) change after a 12 week treatment with Lexiva. With these assumptions and a test for the significant difference of RFS/RSI changes between the two arms, sample sizes of 44 and 44 in Lexiva and placebo group achieve 80% power to detect a minimum effect size of 0.6 at a significance level of 0.05 using a two-sided two-sample equal-variance t-test. We anticipate a 15% drop-out rate during the 3-month treatment course. Therefore, we plan to recruit a total of 104 patients.

A sample size of 44 in the Lexiva group achieves 80% power to detect a minimum correlation of 0.41 between pepsin level at baseline and change of RFS and RSI after a 12-week treatment with Lexiva using a two-sided hypothesis test with a significance level of 0.05.

Data Management

The accuracy of the data collected and entered into REDCap will be validated at the time of entry. Data will be obtained from the patient, EPIC, VPS, PC4, and the billing office (via a CDR request). All data will be kept secure via protected password access to the REDCap (www.project-redcap.org/).

Missing Data

Every effort will be made to avoid missing data, using all available sources. Using logistic regression (LR), the assumption of missing at random data will be explored. If the data appear missing at random (MAR) multiple imputations for items will be used. A sensitivity analysis will be employed, using clinical information and different assumptions to substitute values.

Statistical Analysis

The distribution of and relationship between variables will be explored with statistical summaries such as the mean, median, standard deviation (SD), range, and correlations with plots such as box plots, scatter plots, and Loess smooth curves. Where necessary for parametric assumptions, appropriate transformations will be employed with justification for their use. To test the efficacy of treatment with Lexiva, a two-sample t test will be performed by comparing the mean changes in RFS and RSI between the treatment and placebo groups. Pearson correlation analysis or linear regression will be employed to evaluate the association of the presence and levels of pepsin in saliva pre-treatment and changes of RFS and RSI post-treatment. If needed, such as may be the case where there are outliers, non-parametric tests such as the Wilcoxon and Mann Whitney test or Spearman correlation will be used.

Risks and Safeguarding Against Risks

An oral suspension of Lexiva (50 mg/ml, prodrug of amprenavir, generic name: fosamprenavir) is currently FDA approved for treatment of HIV-1 infection. In adults, the oral suspension is to be taken without food. Therapy-naïve patients are to take 1.4 g twice daily. The same route of administration and dosage level of Lexiva will be used in this clinical trial to assess its efficacy for laryngopharyngeal reflux (LPR).

A medical therapy for patients with LPR is desperately needed. LPR patients present with symptoms that substantially affect quality of life, such as chronic cough, throat clearing, postnasal drip, hoarseness or dysphonia, globus sensation, dysphagia, and dyspnea. Further, chronic LPR contributes to life-threatening illness such as laryngeal cancer. It is estimated that LPR affects more than 20% of the United States population and is present in up to 10% of patients presenting to an otolaryngologist's office. Given that HIV protease inhibitors such as Lexiva target a foreign virus, investigation of Lexiva in LPR patients should not cause significant side effects and should not decrease the acceptability of the risks of this disease.

The procedures utilized in this study will be of minimal risk to the patients. MII-pH test and flexible laryngoscopy (to obtain RFS and RSI) are routine clinical care for this patient population. Research specific tests include collection of saliva for pepsin analysis, RSS and RSA. The RSS is a patient administered questionnaire, which will be obtained at the same time as the clinical RSI. The RSA will be obtained by the study physician when he obtains the clinical RFS during the fiberoptic laryngeal examination.

Example 3: Optimal Particle Size for Use with DPI

Method

In the following Example, the inventors used a small-scale powder disperser (SSPD) to aerosolize Fosamprenavir powder, and monitored particle size distribution by an Optical Particle Sizer (OPS). The SSPD inhales the powder through a venturi aspirator, which is then sampled through OPS at 1 L/min of flow (FIG. 11).

Results

Mass Deposition Calculation in Larynx and Trachea:

$$M_{deposited} = Q \cdot t \int \left[ \eta_{dep} \cdot \left( \frac{\partial m}{\partial d_p} \right) \right] dd_p, \, [\mu g]$$

where Q is the volume inhaled by the mouse, 25 ml/min (0.025 L/min). The factor Q·t represents the total volume inhaled during the exposure (10 mins, 5 mins, and 2.5 mins). $\eta_{dep}$ is the deposition fraction interpolated from Raabe et al. for the larynx and trachea. Raabe et al. has deposition percentages for specific diameters, which were interpolated to the diameters present in the measurements made in this Example.

TABLE

| Deposition data from Raabe paper. | | |
| --- | --- | --- |
| Aerodynamic resistance diameter (μm) | Larynx (%) | Trachea (%) |
| 0.27 | 0.8 | 0.48 |
| 1.09 | 0.8 | 0.18 |
| 3.45 | 2.1 | 0.7 |
| 4.49 | 3.7 | 0.23 |
| 5.98 | 2.3 | 0.8 |
| 9.65 | 3.3 | 0.26 |

The $$\left(\frac{\partial m}{\partial d_p}\right)$$

is calculated from dn/d log dp [#/cm$^3$] measurement data from OPS. Data were converted from dn/d log dp to dn/ddp [#/(cm$^3$ μm)] with the following conversion:

$$\frac{\partial n}{\partial d_p} = \frac{\partial n}{\partial \log_{10} d_p} \cdot \frac{\partial \log_{10} d_p}{\partial d_p} [\#/(cm^3 \mu m)]$$

$$\frac{\partial n}{\partial d_p} = \frac{\partial n}{\partial \log_{10} d_p} \cdot \frac{1}{d_p \log_e 10} [\#/(cm^3 \mu m)]$$

The mass distribution was obtained from number distribution by multiplying by density as shown below:

$$\frac{\partial m}{\partial d_p} = \rho[Kg/m^3] \cdot \frac{\partial n}{\partial d_p} [num/(cm^3 \mu m)] \cdot \frac{\pi}{6} \cdot d_p^3 [\mu m]$$

$$\frac{\partial m}{\partial d_p} = \rho[10^6 mg/m^3] \cdot \frac{\partial n}{\partial d_p} [num/(cm^3 \mu m)] \cdot \frac{\pi}{6} \cdot (d_p^3 \cdot 10^{-6}[m]),$$

$$[mg/cm^3(\mu m)]$$

$$\frac{\partial m}{\partial d_p} = \rho[10^6 mg/m^3] \cdot \frac{\partial n}{\partial d_p} [num/(cm^3 \mu m)] \cdot \frac{\pi}{6} \cdot (d_p^3 \cdot 10^{-6}[m]) \times 10^6,$$

$$[\mu g/L(\mu m)]$$

The above formula can be implemented in a Matlab code, or the like, to get the mass deposited in the trachea and larynx.

A preliminary 12-day toxicity study was conducted in mice. No pathology was observed in the nasal cavity, larynx, esophagus, trachea, lung, liver, and kidney tissues from either the control or fosamprenavir exposed mice. In one of the fosamprenavir-treated mice, the heart did demonstrate significant inflammation. This was the only animal affected, across 15 treated mice, so this is suspected to be unrelated to the fosamprenavir treatment.

Bronchiolar lavage samples were collected from all mice and a Luminex assay was used to measure 14 relevant biomarkers for inflammation and toxicity. One comparison in particular showed significance: IL-6 between control and the lowest dose of fosamprenavir.

Summary

For a dry powder inhaler (DPI), a stationary bed of powder is fluidized as an aerosol, and then, in some instances, aggregates are disrupted to generate particles in a size range appropriate for deposition in the larynx. It is an aspect of the present disclosure that such an aerosol be generated by a small-scale powder disperser that utilizes the Venturi effect to fluidize the particles. As described above, the particle size was measured with an optical particle spectrometer. The output was also determined, which is expressed as the aerosol mass distribution function; that is, mass of particles per unit volume of air per unit size, as a function of diameter. The mass distribution can be integrated to yield the total mass concentration and used to directly calculate the deposition mass in all regions of the respiratory system.

As can be seen in FIG. 16, aerosols were readily generated with fosamprenavir, and the particle size was appropriate to carry out preliminary toxicity studies. Based on these results, a size range of 2-9 μm represented an optimal choice in terms of higher deposition fraction in the larynx and lower deposition elsewhere in the respiratory tract.

REFERENCES

1. Ford C N. Evaluation and management of laryngopharyngeal reflux. JAMA. 2005; 294(12):1534-40. Epub 2005, Sep. 29. doi: 10.1001/jama.294.12.1534. PubMed PMID: 16189367.
2. Koufman J A. The otolaryngologic manifestations of gastroesophageal reflux disease (GERD): a clinical investigation of 225 patients using ambulatory 24-hour pH monitoring and an experimental investigation of the role of acid and pepsin in the development of laryngeal injury. Laryngoscope. 1991; 101(4 Pt 2 Suppl 53):1-78. Epub 1991, Apr. 1. doi: 10.1002/lary.1991.101.s53.1. PubMed PMID: 1895864.
3. Vaezi M F. Extraesophageal manifestations of gastroesophageal reflux disease. Clin Cornerstone. 2003; 5(4): 32-8; discussion 9-40. Epub 2004, Apr. 23. doi: 10.1016/s1098-3597(03)90097-4. PubMed PMID: 15101493.
4. Gabriel C E, Jones D G. The importance of chronic laryngitis. J Laryngol Otol. 1960; 74:349-57. Epub 1960, Jun. 1. doi: 10.1017/s0022215100056693. PubMed PMID: 13825824.
5. Johnston N, Yan J C, Hoekzema C R, Samuels T L, Stoner G D, Blumin J H, Bock J M. Pepsin promotes proliferation of laryngeal and pharyngeal epithelial cells. Laryngoscope. 2012; 122(6):1317-25. Epub 2012, May 10. doi: 10.1002/lary.23307. PubMed PMID: 22570308; PMCID: PMC3816638.
6. Kelly E A, Samuels T L, Johnston N. Chronic pepsin exposure promotes anchorage-independent growth and migration of a hypopharyngeal squamous cell line. Otolaryngol Head Neck Surg. 2014; 150(4):618-24. Epub 2014, Jan. 1. doi: 10.1177/0194599813517862. PubMed PMID: 24376122; PMCID: PMC4423599.
7. Kim S Y, Park B, Lim H, Kim M, Kong I G, Choi H G. Increased risk of larynx cancer in patients with gastroesophageal reflux disease from a national sample cohort. Clin Otolaryngol. 2019; 44(4):534-40. Epub 2019, Mar. 19. doi: 10.1111/coa.13328. PubMed PMID: 30884136.
8. Parsel S M, Wu E L, Riley C A, McCoul E D. Gastroesophageal and Laryngopharyngeal Reflux Associated With Laryngeal Malignancy: A Systematic Review and Meta-analysis. Clin Gastroenterol Hepatol. 2019; 17(7): 1253-64 e5. Epub 2018, Oct. 27. doi: 10.1016/j.cgh.2018.10.028. PubMed PMID: 30366155.
9. Riley C A, Wu E L, Hsieh M C, Marino M J, Wu X C, McCoul E D. Association of Gastroesophageal Reflux With Malignancy of the Upper Aerodigestive Tract in Elderly Patients. JAMA Otolaryngol Head Neck Surg.

2018; 144(2):140-8. Epub 2017, Dec. 23. doi: 10.1001/jamaoto.2017.2561. PubMed PMID: 29270624; PMCID: PMC5839296.

10. Tae K, Jin B J, Ji Y B, Jeong J H, Cho S H, Lee S H. The role of laryngopharyngeal reflux as a risk factor in laryngeal cancer: a preliminary report. Clin Exp Otorhinolaryngol. 2011; 4(2):101-4. Epub 2011, Jul. 1. doi: 10.3342/ceo.2011.4.2.101. PubMed PMID: 21716948; PMCID: PMC3109325.

11. Wight R, Paleri V, Arullendran P. Current theories for the development of nonsmoking and nondrinking laryngeal carcinoma. Curr Opin Otolaryngol Head Neck Surg. 2003; 11(2):73-7. Epub 2003, Sep. 30. doi: 10.1097/00020840-200304000-00002. PubMed PMID: 14515082.

12. Altman K W, Stephens R M, Lyttle C S, Weiss K B. Changing impact of gastroesophageal reflux in medical and otolaryngology practice. Laryngoscope. 2005; 115 (7):1145-53. Epub 2005, Jul. 5. doi: 10.1097/01.MLG.0000165464.75164.E5. PubMed PMID: 15995499.

13. Koufman J A, Amin M R, Panetti M. Prevalence of reflux in 113 consecutive patients with laryngeal and voice disorders. Otolaryngol Head Neck Surg. 2000; 123(4):385-8. Epub 2000, Oct. 6. doi: 10.1067/mhn.2000.109935. PubMed PMID: 11020172.

14. Reulbach T R, Belafsky P C, Blalock P D, Koufman J A, Postma G N. Occult laryngeal pathology in a community-based cohort. Otolaryngol Head Neck Surg. 2001; 124 (4):448-50. Epub 2001, Apr. 3. doi: 10.1067/mhn.2001.114256. PubMed PMID: 11283505.

15. Francis D O, Rymer J A, Slaughter J C, Choksi Y, Jiramongkolchai P, Ogbeide E, Tran C, Goutte M, Garrett C G, Hagaman D, Vaezi M F. High economic burden of caring for patients with suspected extraesophageal reflux. Am J Gastroenterol. 2013; 108(6):905-11. Epub 2013, Apr. 3. doi: 10.1038/ajg.2013.69. PubMed PMID: 23545710.

16. Gelardi M, Ciprandi G. Focus on gastroesophageal reflux (GER) and laryngopharyngeal reflux (LPR): new pragmatic insights in clinical practice. J Biol Regul Homeost Agents. 2018; 32(1 Suppl. 2):41-7. Epub 2018, Feb. 3. PubMed PMID: 29436209.

17. Ali M S, Parikh S, Chater P, Pearson J P. Bile acids in laryngopharyngeal refluxate: will they enhance or attenuate the action of pepsin? Laryngoscope. 2013; 123(2):434-9. Epub 2012, Oct. 17. doi: 10.1002/lary.23619. PubMed PMID: 23070961.

18. Bardhan K D, Strugala V, Dettmar P W. Reflux revisited: advancing the role of pepsin. Int J Otolaryngol. 2012; 2012:646901. Epub 2012, Jan. 14. doi: 10.1155/2012/646901. PubMed PMID: 22242022; PMCID: PMC3216344.

19. Campagnolo A M, Priston J, Thoen R H, Medeiros T, Assuncao A R. Laryngopharyngeal reflux: diagnosis, treatment, and latest research. Int Arch Otorhinolaryngol. 2014; 18(2):184-91. Epub 2015, May 21. doi: 10.1055/s-0033-1352504. PubMed PMID: 25992088; PMCID: PMC4297018.

20. Johnston N, Dettmar P W, Bishwokarma B, Lively M O, Koufman J A. Activity/stability of human pepsin: implications for reflux attributed laryngeal disease. Laryngoscope. 2007; 117(6): 1036-9. Epub 2007, Apr. 10. doi: 10.1097/MLG.0b013e31804154c3. PubMed PMID: 17417109.

21. Samuels T L, Johnston N. Pepsin as a causal agent of inflammation during nonacidic reflux. Otolaryngol Head Neck Surg. 2009; 141(5):559-63. Epub 2009, Oct. 29. doi: 10.1016/j.otohns.2009.08.022. PubMed PMID: 19861190.

22. Tan J J, Wang L, Mo T T, Wang J, Wang M G, Li X P. Pepsin promotes IL-8 signaling-induced epithelial-mesenchymal transition in laryngeal carcinoma. Cancer Cell Int. 2019; 19:64. Epub 2019, Apr. 3. doi: 10.1186/s12935-019-0772-7. PubMed PMID: 30936780; PMCID: PMC6425698.

23. Lechien J R, Bock J M, Carroll T L, Akst L M. Is empirical treatment a reasonable strategy for laryngopharyngeal reflux? A contemporary review. Clin Otolaryngol. 2020. Epub 2020/02/26. doi: 10.1111/coa.13518. PubMed PMID: 32097534.

24. Samuels T L, Johnston N. Pepsin as a marker of extraesophageal reflux. Ann Otol Rhinol Laryngol. 2010; 119(3):203-8. Epub 2010, Apr. 16. doi: 10.1177/000348941011900310. PubMed PMID: 20392035.

25. Piper D W, Fenton B H. pH stability and activity curves of pepsin with special reference to their clinical importance. Gut. 1965; 6(5):506-8. Epub 1965, Oct. 1. doi: 10.1136/gut.6.5.506. PubMed PMID: 4158734; PMCID: PMC1552331.

26. Axford S E, Sharp N, Ross P E, Pearson J P, Dettmar P W, Panetti M, Koufman J A. Cell biology of laryngeal epithelial defenses in health and disease: preliminary studies. Ann Otol Rhinol Laryngol. 2001; 110(12):1099-108. Epub 2002, Jan. 5. doi: 10.1177/000348940111001203. PubMed PMID: 11768697.

27. Hopwood D, Bateson M C, Milne G, Bouchier I A. Effects of bile acids and hydrogen ion on the fine structure of oesophageal epithelium. Gut. 1981; 22(4):306-11. Epub 1981/04/01. doi: 10.1136/gut.22.4.306. PubMed PMID: 7239322; PMCID: PMC1419165.

28. Eto T, Tompkins R K. Further studies on the inhibition of pepsin by bile salts. Ann Surg. 1986; 203(1):8-12. Epub 1986, Jan. 1. doi: 10.1097/00000658-198601000-00002. PubMed PMID: 3079997; PMCID: PMC1251031.

29. Pearson J P, Parikh S, Orlando R C, Johnston N, Allen J, Tinling S P, Johnston N, Belafsky P, Arevalo L F, Sharma N, Castell D O, Fox M, Harding S M, Morice A H, Watson M G, Shields M D, Bateman N, McCallion W A, van Wijk M P, Wenzl T G, Karkos P D, Belafsky P C. Review article: reflux and its consequences—the laryngeal, pulmonary and oesophageal manifestations. Conference held in conjunction with the 9th International Symposium on Human Pepsin (ISHP) Kingston-upon-Hull, UK, 21-23 Apr. 2010. Aliment Pharmacol Ther. 2011; 33 Suppl 1:1-71. Epub 2011, Mar. 5. doi: 10.1111/j.1365-2036.2011.04581.x. PubMed PMID: 21366630.

30. Calvo-Henriquez C, Ruano-Ravina A, Vaamonde P, Martinez-Capoccioni G, Martin-Martin C. Is Pepsin a Reliable Marker of Laryngopharyngeal Reflux? A Systematic Review. Otolaryngol Head Neck Surg. 2017; 157(3):385-91. Epub 2017, Jun. 7. doi: 10.1177/0194599817709430. PubMed PMID: 28585488.

31. Johnston N, Dettmar P W, Ondrey F G, Nanchal R, Lee S H, Bock J M. Pepsin: biomarker, mediator, and therapeutic target for reflux and aspiration. Ann N Y Acad Sci. 2018; 1434(1):282-9. Epub 2018, May 19. doi: 10.1111/nyas.13729. PubMed PMID: 29774546.

32. Johnston N, Wells C W, Samuels T L, Blumin J H. Pepsin in nonacidic refluxate can damage hypopharyngeal epithelial cells. Ann Otol Rhinol Laryngol. 2009; 118(9):677-85. Epub 2009, Oct. 9. doi: 10.1177/000348940911800913. PubMed PMID: 19810610.

33. Johnston N, Wells C W, Samuels T L, Blumin J H. Rationale for targeting pepsin in the treatment of reflux disease. Ann Otol Rhinol Laryngol. 2010; 119(8):547-58. Epub 2010/09/24. doi: 10.1177/000348941011900808. PubMed PMID: 20860281.

34. Weitzendorfer M, Antoniou S A, Schredl P, Witzel K, Weitzendorfer I C, Majerus A, Emmanuel K, Koch 00. Pepsin and oropharyngeal pH monitoring to diagnose patients with laryngopharyngeal reflux. Laryngoscope. 2019. Epub 2019, Oct. 12. doi: 10.1002/lary.28320. PubMed PMID: 31603541.

35. Zalvan C H, Hu S, Greenberg B, Geliebter J. A Comparison of Alkaline Water and Mediterranean Diet vs Proton Pump Inhibition for Treatment of Laryngopharyngeal Reflux. JAMA Otolaryngol Head Neck Surg. 2017; 143(10):1023-9. Epub 2017, Sep. 8. doi: 10.1001/jamaoto.2017.1454. PubMed PMID: 28880991; PMCID: PMC5710251.

36. Gill G A, Johnston N, Buda A, Pignatelli M, Pearson J, Dettmar P W, Koufman J. Laryngeal epithelial defenses against laryngopharyngeal reflux: investigations of E-cadherin, carbonic anhydrase isoenzyme III, and pepsin. Ann Otol Rhinol Laryngol. 2005; 114(12):913-21. Epub 2006, Jan. 24. doi: 10.1177/000348940511401204. PubMed PMID: 16425556.

37. Johnston N, Bulmer D, Gill G A, Panetti M, Ross P E, Pearson J P, Pignatelli M, Axford S E, Dettmar P W, Koufman J A. Cell biology of laryngeal epithelial defenses in health and disease: further studies. Ann Otol Rhinol Laryngol. 2003; 112(6):481-91. Epub 2003/07/02. doi: 10.1177/000348940311200601. PubMed PMID: 12834114.

38. Johnston N, Knight J, Dettmar P W, Lively M O, Koufman J. Pepsin and carbonic anhydrase isoenzyme III as diagnostic markers for laryngopharyngeal reflux disease. Laryngoscope. 2004; 114(12):2129-34. Epub 2004, Nov. 27. doi: 10.1097/01.mlg.0000149445.07146.03. PubMed PMID: 15564833.

39. Agrawal A, Roberts J, Sharma N, Tutuian R, Vela M, Castell D O. Symptoms with acid and nonacid reflux may be produced by different mechanisms. Dis Esophagus. 2009; 22(5):467-70. Epub 2009, Feb. 19. doi: 10.1111/j.1442-2050.2009.00940.x. PubMed PMID: 19222535.

40. Tamhankar A P, Peters J H, Portale G, Hsieh C C, Hagen J A, Bremner C G, DeMeester T R. Omeprazole does not reduce gastroesophageal reflux: new insights using multichannel intraluminal impedance technology. J Gastrointest Surg. 2004; 8(7):890-7; discussion 7-8. Epub 2004, Nov. 9. doi: 10.1016/j.gassur.2004.08.001. PubMed PMID: 15531244.

41. Tutuian R, Mainie I, Agrawal A, Adams D, Castell D O. Nonacid reflux in patients with chronic cough on acid-suppressive therapy. Chest. 2006; 130(2):386-91. Epub 2006/08/11. doi: 10.1378/chest.130.2.386. PubMed PMID: 16899836.

42. Tutuian R, Vela M F, Hill E G, Mainie I, Agrawal A, Castell D O. Characteristics of symptomatic reflux episodes on Acid suppressive therapy. Am J Gastroenterol. 2008; 103(5):1090-6. Epub 2008, May 1. doi: 10.1111/j.1572-0241.2008.01791.x. PubMed PMID: 18445095.

43. Falk G L, Van der Wall H, Burton L, Falk M G, O'Donnell H, Vivian S J. Fundoplication for laryngopharyngeal reflux despite preoperative dysphagia. Ann R Coll Surg Engl. 2017; 99(3):224-7. Epub 2017, Mar. 3. doi: 10.1308/rcsann.2016.0330. PubMed PMID: 28252352; PMCID: PMC5450280.

44. Iqbal M, Batch A J, Moorthy K, Cooper B T, Spychal R T. Outcome of surgical fundoplication for extra-oesophageal symptoms of reflux. Surg Endosc. 2009; 23(3):557-61. Epub 2008, Mar. 28. doi: 10.1007/s00464-008-9861-8. PubMed PMID: 18365279.

45. Lechien J R, Dapri G, Dequanter D, Rodriguez Ruiz A, Marechal M T, De Marrez L G, Saussez S, Fisichella P M. Surgical Treatment for Laryngopharyngeal Reflux Disease: A Systematic Review. JAMA Otolaryngol Head Neck Surg. 2019; 145(7):655-66. Epub 2019, May 3. doi: 10.1001/jamaoto.2019.0315. PubMed PMID: 31046069.

46. Mainie I, Tutuian R, Shay S, Vela M, Zhang X, Sifrim D, Castell D O. Acid and non-acid reflux in patients with persistent symptoms despite acid suppressive therapy: a multicentre study using combined ambulatory impedance-pH monitoring. Gut. 2006; 55(10):1398-402. Epub 2006, Mar. 25. doi: 10.1136/gut.2005.087668. PubMed PMID: 16556669; PMCID: PMC1856433.

47. Sidwa F, Moore A L, Alligood E, Fisichella P M. Surgical Treatment of Extraesophageal Manifestations of Gastroesophageal Reflux Disease. World J Surg. 2017; 41(10):2566-71. Epub 2017, May 17. doi: 10.1007/s00268-017-4058-8. PubMed PMID: 28508234.

48. Zhang C, Hu Z W, Yan C, Wu Q, Wu J M, Du X, Liu D G, Luo T, Li F, Wang Z G. Nissen fundoplication vs proton pump inhibitors for laryngopharyngeal reflux based on pH-monitoring and symptom-scale. World J Gastroenterol. 2017; 23(19):3546-55. Epub 2017/06/10. doi: 10.3748/wjg.v23.i19.3546. PubMed PMID: 28596691; PMCID: PMC5442091.

49. Johnston N, Wells C W, Blumin J H, Toohill R J, Merati A L. Receptor-mediated uptake of pepsin by laryngeal epithelial cells. Ann Otol Rhinol Laryngol. 2007; 116(12):934-8. Epub 2008, Jan. 26. doi: 10.1177/000348940711601211. PubMed PMID: 18217514.

50. Rees L E, Pazmany L, Gutowska-Owsiak D, Inman C F, Phillips A, Stokes C R, Johnston N, Koufman J A, Postma G, Bailey M, Birchall M A. The mucosal immune response to laryngopharyngeal reflux. Am J Respir Crit Care Med. 2008; 177(11):1187-93. Epub 2008/03/08. doi: 10.1164/rccm.200706-8950C. PubMed PMID: 18323539; PMCID: PMC2643204.

51. Samuels T L, Altman K W, Gould J C, Kindel T, Bosler M, MacKinnon A, Hagen C E, Johnston N. Esophageal pepsin and proton pump synthesis in barrett's esophagus and esophageal adenocarcinoma. Laryngoscope. 2019; 129(12):2687-95. Epub 2019, May 3. doi: 10.1002/lary.28051. PubMed PMID: 31046139.

52. Niu K, Guo C, Teng S, Zhou D, Yu S, Yin W, Wang P, Zhu W, Duan M. Pepsin promotes laryngopharyngeal neoplasia by modulating signaling pathways to induce cell proliferation. PLoS One. 2020; 15(1):e0227408. Epub 2020, Jan. 16. doi: 10.1371/journal.pone.0227408. PubMed PMID: 31940393; PMCID: PMC6961942.

53. Johnston N, Dettmar P W, Lively M O, Postma G N, Belafsky P C, Birchall M, Koufman J A. Effect of pepsin on laryngeal stress protein (Sep70, Sep53, and Hsp70) response: role in laryngopharyngeal reflux disease. Ann Otol Rhinol Laryngol. 2006; 115(1):47-58. Epub 2006/02/10. doi: 10.1177/000348940611500108. PubMed PMID: 16466100.

54. Hurley B P, Jugo R H, Snow R F, Samuels T L, Yonker L M, Mou H, Johnston N, Rosen R. Pepsin Triggers Neutrophil Migration Across Acid Damaged Lung Epithelium. Sci Rep. 2019; 9(1):13778. Epub 2019, Sep. 26. doi: 10.1038/s41598-019-50360-4. PubMed PMID: 31551494; PMCID: PMC6760148.

55. Nagahama K, Yamato M, Nishio H, Takeuchi K. Essential role of pepsin in pathogenesis of acid reflux esophagitis in rats. Dig Dis Sci. 2006; 51(2):303-9. Epub 2006/03/15. doi: 10.1007/s10620-006-3129-8. PubMed PMID: 16534673.

56. Samuels T L, Pearson A C, Wells C W, Stoner G D, Johnston N. Curcumin and anthocyanin inhibit pepsin-mediated cell damage and carcinogenic changes in airway epithelial cells. Ann Otol Rhinol Laryngol. 2013; 122 (10):632-41. Epub 2013, Dec. 4. PubMed PMID: 24294686.

57. Martinucci I, de Bortoli N, Savarino E, Nacci A, Romeo S O, Bellini M, Savarino V, Fattori B, Marchi S. Optimal treatment of laryngopharyngeal reflux disease. Ther Adv Chronic Dis. 2013; 4(6):287-301. Epub 2013, Nov. 2. doi: 10.1177/2040622313503485. PubMed PMID: 24179671; PMCID: PMC3807765.

58. Koufman J A, Aviv J E, Casiano R R, Shaw G Y. Laryngopharyngeal reflux: position statement of the committee on speech, voice, and swallowing disorders of the American Academy of Otolaryngology-Head and Neck Surgery. Otolaryngol Head Neck Surg. 2002; 127(1):32-5. Epub 2002, Aug. 6. doi: 10.1067/mhn.2002.125760. PubMed PMID: 12161727.

59. Park W, Hicks D M, Khandwala F, Richter J E, Abelson T I, Milstein C, Vaezi M F. Laryngopharyngeal reflux: prospective cohort study evaluating optimal dose of proton-pump inhibitor therapy and pretherapy predictors of response. Laryngoscope. 2005; 115(7):1230-8. Epub 2005, Jul. 5. doi: 10.1097/01.MLG.0000163746.81766.45. PubMed PMID: 15995512.

60. Eherer A J, Habermann W, Hammer H F, Kiesler K, Friedrich G, Krejs G J. Effect of pantoprazole on the course of reflux-associated laryngitis: a placebo-controlled double-blind crossover study. Scand J Gastroenterol. 2003; 38(5):462-7. Epub 2003, Jun. 11. doi: 10.1080/00365520310001860. PubMed PMID: 12795454.

61. El-Serag H B, Lee P, Buchner A, Inadomi J M, Gavin M, McCarthy D M. Lansoprazole treatment of patients with chronic idiopathic laryngitis: a placebo-controlled trial. Am J Gastroenterol. 2001; 96(4):979-83. Epub 2001, Apr. 24. doi: 10.1111/j.1572-0241.2001.03681.x. PubMed PMID: 11316215.

62. Noordzij J P, Khidr A, Evans B A, Desper E, Mittal R K, Reibel J F, Levine P A. Evaluation of omeprazole in the treatment of reflux laryngitis: a prospective, placebo-controlled, randomized, double-blind study. Laryngoscope. 2001; 111(12):2147-51. Epub 2002/01/22. doi: 10.1097/00005537-200112000-00013. PubMed PMID: 11802014.

63. Steward D L, Wilson K M, Kelly D H, Patil M S, Schwartzbauer H R, Long J D, Welge J A. Proton pump inhibitor therapy for chronic laryngo-pharyngitis: a randomized placebo-control trial. Otolaryngol Head Neck Surg. 2004; 131(4):342-50. Epub 2004, Oct. 7. doi: 10.1016/j.otohns.2004.03.037. PubMed PMID: 15467597.

64. Vaezi M F, Richter J E, Stasney C R, Spiegel J R, Iannuzzi R A, Crawley J A, Hwang C, Sostek M B, Shaker R. Treatment of chronic posterior laryngitis with esomeprazole. Laryngoscope. 2006; 116(2):254-60. Epub 2006, Feb. 10. doi: 10.1097/01.mlg.0000192173.00498.ba. PubMed PMID: 16467715.

65. Wo J M, Koopman J, Harrell S P, Parker K, Winstead W, Lentsch E. Double-blind, placebo-controlled trial with single-dose pantoprazole for laryngopharyngeal reflux. Am J Gastroenterol. 2006; 101(9):1972-8; quiz 2169. Epub 2006, Sep. 14. doi: 10.1111/j.1572-0241.2006.00693.x. PubMed PMID: 16968502.

66. Lam P K, Ng M L, Cheung T K, Wong B Y, Tan V P, Fong D Y, Wei W I, Wong B C. Rabeprazole is effective in treating laryngopharyngeal reflux in a randomized placebo-controlled trial. Clin Gastroenterol Hepatol. 2010; 8(9):770-6. Epub 2010, Mar. 23. doi: 10.1016/j.cgh.2010.03.009. PubMed PMID: 20303417.

67. Reichel O, Dressel H, Wiederanders K, Issing W J. Double-blind, placebo-controlled trial with esomeprazole for symptoms and signs associated with laryngopharyngeal reflux. Otolaryngol Head Neck Surg. 2008; 139(3):414-20. Epub 2008, Aug. 30. doi: 10.1016/j.otohns.2008.06.003. PubMed PMID: 18722223.

68. Vaezi M F. Gastroesophageal reflux-related chronic laryngitis: con. Arch Otolaryngol Head Neck Surg. 2010; 136(9):908-9. Epub 2010, Sep. 22. doi: 10.1001/archoto.2010.149. PubMed PMID: 20855684.

69. Lien H C, Wang C C, Liang W M, Sung F C, Hsu J Y, Yeh H Z, Chong K, Chang C S. Composite pH predicts esomeprazole response in laryngopharyngeal reflux without typical reflux syndrome. Laryngoscope. 2013; 123(6):1483-9. Epub 2013, Apr. 5. doi: 10.1002/lary.23780. PubMed PMID: 23553459.

70. Masaany M, Marina M B, Sharifa Ezat W P, Sani A. Empirical treatment with pantoprazole as a diagnostic tool for symptomatic adult laryngopharyngeal reflux. J Laryngol Otol. 2011; 125(5):502-8. Epub 2011, Mar. 2. doi: 10.1017/S0022215111000120. PubMed PMID: 21356141.

71. Kahrilas P J. When proton pump inhibitors fail. Clin Gastroenterol Hepatol. 2008; 6(5):482-3. Epub 2008, Apr. 2. doi: 10.1016/j.cgh.2008.02.010. PubMed PMID: 18378500; PMCID: PMC2474735.

72. Barry D W, Vaezi M F. Laryngopharyngeal reflux: More questions than answers. Cleve Clin J Med. 2010; 77(5):327-34. Epub 2010, May 5. doi: 10.3949/ccjm.77a.09121. PubMed PMID: 20439565.

73. Belafsky P C. PRO: Empiric treatment with PPIs is not appropriate without testing. Am J Gastroenterol. 2006; 101(1):6-8. Epub 2006, Jan. 13. doi: 10.1111/j.1572-0241.2006.00448_2.x. PubMed PMID: 16405525.

74. Hvid-Jensen F, Pedersen L, Funch-Jensen P, Drewes A M. Proton pump inhibitor use may not prevent high-grade dysplasia and oesophageal adenocarcinoma in Barrett's oesophagus: a nationwide study of 9883 patients. Aliment Pharmacol Ther. 2014; 39(9):984-91. Epub 2014, Mar. 13. doi: 10.1111/apt.12693. PubMed PMID: 24617286.

75. Luebke K, Samuels T L, Chelius T H, Sulman C G, McCormick M E, Kerschner J E, Johnston N, Chun R H. Pepsin as a biomarker for laryngopharyngeal reflux in children with laryngomalacia. Laryngoscope. 2017; 127 (10):2413-7. Epub 2017, Feb. 23. doi: 10.1002/lary.26537. PubMed PMID: 28224634.

76. Kamani T, Penney S, Mitra I, Pothula V. The prevalence of laryngopharyngeal reflux in the English population. Eur Arch Otorhinolaryngol. 2012; 269(10):2219-25. Epub 2012/05/12. doi: 10.1007/s00405-012-2028-1. PubMed PMID: 22576243.

77. Lowden M, McGlashan J A, Steel A, Strugala V, Dettmar P W. Prevalence of symptoms suggestive of extra-oesophageal reflux in a general practice population in the UK. Logoped Phoniatr Vocol. 2009; 34(1):32-5. Epub 2009, Feb. 14. doi: 10.1080/14015430902735847. PubMed PMID: 19214865.

78. Caicedo-Granados E, Galbraith A R, Schachern M G, Hartle D E, Wattenberg L W, Wuertz B R, Keel S, Yueh B, Ondrey F G. N-methylnitrosourea-induced carcinoma as a model for laryngeal carcinogenesis. Head Neck. 2014; 36(12):1802-6. Epub 2014, Dec. 31. doi: 10.1002/hed.23536. PubMed PMID: 25548813.

79. Belafsky P C, Postma G N, Koufman J A. The validity and reliability of the reflux finding score (RFS). Laryngoscope. 2001; 111(8):1313-7. Epub 2001, Sep. 25. doi: 10.1097/00005537-200108000-00001. PubMed PMID: 11568561.

80. Belafsky P C, Postma G N, Koufman J A. Validity and reliability of the reflux symptom index (RSI). J Voice. 2002; 16(2):274-7. Epub 2002, Aug. 2. doi: 10.1016/s0892-1997(02)00097-8. PubMed PMID: 12150380.

81. Lechien J R, Akst L M, Hamdan A L, Schindler A, Karkos P D, Barillari M R, Calvo-Henriquez C, Crevier-Buchman L, Finck C, Eun Y G, Saussez S, Vaezi M F. Evaluation and Management of Laryngopharyngeal Reflux Disease: State of the Art Review. Otolaryngol Head Neck Surg. 2019; 160(5):762-82. Epub 2019, Feb. 13. doi: 10.1177/0194599819827488. PubMed PMID: 30744489.

82. Lechien J R, Bobin F, Mouawad F, Zelenik K, Calvo-Henriquez C, Chiesa-Estomba C M, Enver N, Nacci A, Barillari M R, Schindler A, Crevier-Buchman L, Hans S, Simeone V, Wlodarczyk E, Harmegnies B, Remade M, Rodriguez A, Dequanter D, Eisendrath P, Dapri G, Finck C, Karkos P, Pendleton H, Ayad T, Muls V, Saussez S. Development of scores assessing the refluxogenic potential of diet of patients with laryngopharyngeal reflux. Eur Arch Otorhinolaryngol. 2019; 276(12):3389-404. Epub 2019, Sep. 14. doi: 10.1007/s00405-019-05631-1. PubMed PMID: 31515662.

83. Lechien J R, Bobin F, Muls V, Thill M P, Horoi M, Ostermann K, Huet K, Harmegnies B, Dequanter D, Dapri G, Marechal M T, Finck C, Rodriguez Ruiz A, Saussez S. Validity and reliability of the reflux symptom score. Laryngoscope. 2020; 130(3):E98-E107. Epub 2019, Apr. 16. doi: 10.1002/lary.28017. PubMed PMID: 30983002.

84. Lechien J R, Rodriguez Ruiz A, Dequanter D, Bobin F, Mouawad F, Muls V, Huet K, Harmegnies B, Remade S, Finck C, Saussez S. Validity and Reliability of the Reflux Sign Assessment. Ann Otol Rhinol Laryngol. 2020; 129 (4):313-25. Epub 2019, Nov. 16. doi: 10.1177/0003489419888947. PubMed PMID: 31729247.

85. Lien H C, Wang C C, Lee S W, Hsu J Y, Yeh H Z, Ko C W, Chang C S, Liang W M. Responder Definition of a Patient-Reported Outcome Instrument for Laryngopharyngeal Reflux Based on the US FDA Guidance. Value Health. 2015; 18(4):396-403. Epub 2015, Jun. 21. doi: 10.1016/j.jval.2015.01.001. PubMed PMID: 26091593.

86. Klimara M J, Johnston N, Samuels T L, Visotcky A M, Poetker D M, Loehrl T A, Blumin J H, Bock J M. Correlation of salivary and nasal lavage pepsin with MII-pH testing. Laryngoscope. 2020; 130(4):961-6. Epub 2019, Jul. 23. doi: 10.1002/lary.28182. PubMed PMID: 31329290.

87. Marshall S, McCann A J, Samuels T L, Blair A, Bonne V, Johnston N, Koufman J. Detection of pepsin and IL-8 in saliva of adult asthmatic patients. J Asthma Allergy. 2019; 12:155-61. Epub 2019, Jun. 20. doi: 10.2147/JAA.S205482. PubMed PMID: 31213853; PMCID: PMC6549784.

88. Potluri S, Friedenberg F, Parkman H P, Chang A, MacNeal R, Manus C, Bromer M Q, Malik A, Fisher R S, Nugent T, Thangada V K, Kueppers F, Miller L S. Comparison of a salivary/sputum pepsin assay with 24-hour esophageal pH monitoring for detection of gastric reflux into the proximal esophagus, oropharynx, and lung. Dig Dis Sci. 2003; 48(9):1813-7. Epub 2003, Oct. 17. doi: 10.1023/a:1025467600662. PubMed PMID: 14561007.

89. Crapko M, Kerschner J E, Syring M, Johnston N. Role of extra-esophageal reflux in chronic otitis media with effusion. Laryngoscope. 2007; 117(8):1419-23. Epub 2007/06/23. doi: 10.1097/MLG.0b013e318064f177. PubMed PMID: 17585281.

90. Knight J, Lively M O, Johnston N, Dettmar P W, Koufman J A. Sensitive pepsin immunoassay for detection of laryngopharyngeal reflux. Laryngoscope. 2005; 115(8):1473-8. Epub 2005, Aug. 12

91. Roberts N B, Taylor W H. Comparative Pepstatin Inhibition Studies on Individual Human Pepsins and Pepsinogens 1,3 and 5(gastricsin) and Pig Pepsin A. J Enzyme Inhib Med Chem. 2003; 18(3):209-217.

92. Lea W A, Simeonov A. Fluorescence polarization assays in small molecule screening. Expert Opin Drug Discov. 2011; 6(1):17-32.

93. Jolley M E. Fluorescence polarization assays for the detection of proteases and their inhibitors. J. Biomol. Screen. 1996; 1(1):33-8, 94. Schade S Z, Jolley M E, Sarauer B J, Simonson L G. BODIPY-alpha-casein, a pH-independent protein substrate for protease assays using fluorescence polarization. Anal Biochem. 1996 Dec 1; 243(1):1-7

95. Olp M D, Kalous K S, Smith B C. An online tool for calculating initial rates from continuous enzyme kinetic traces. bioRxiv 700138; Jul. 14, 2019.

96. Raabe O, Al-Bayati, M A., Teague S V., Rasoly, A. Regional deposition of inhaled monodisperse coarse and fine particles in small laboratory animals. Ann occup Hyg. 1988; 32:53-63.

SEQUENCE LISTING

```
Sequence total quantity: 1
SEQ ID NO: 1          moltype = AA  length = 8
FEATURE               Location/Qualifiers
source                1..8
                      mol_type = protein
                      organism = synthetic construct
SITE                  6
                      note = paranitrophenylalanine
SEQUENCE: 1
KPAEFXRL                                                    8
```

What is claimed:

1. A method of treating reflux in a subject in need thereof, the method comprising administering a therapeutically effective amount of an HIV protease inhibitor to a subject to treat the reflux, wherein the HIV protease inhibitor is fosamprenavir and wherein the subject has an airway reflux condition selected from laryngopharyngeal reflux (LPR), gastropharyngeal reflux (GPR), and esophagopharyngeal reflux (EPR).

2. The method of claim 1, wherein the HIV protease inhibitor is capable of binding to and inhibiting the enzymatic activity of pepsin.

3. The method of claim 1, wherein the HIV protease inhibitor is administered orally.

4. The method of claim 1, wherein the HIV protease inhibitor is administered as an aerosol.

5. The method of claim 4, wherein the HIV protease inhibitor is administered as a nasal spray.

6. The method of claim 4, wherein the HIV protease inhibitor is administered via an inhaler or nebulizer.

7. The method of claim 1, wherein the HIV protease inhibitor is administered twice daily at a dosage of about 1.4 g or lower.

8. The method of claim 1, wherein the subject's condition is refractory to treatment with a proton pump inhibitor (PPI).

9. The method of claim 1, wherein the method reduces laryngeal mucosal damage and inflammation.

10. The method of claim 1, wherein the subject has gastroesophageal reflux disease (GERD).

11. The method of claim 10, wherein the subject's GERD is refractory to treatment with a proton pump inhibitor (PPI).

\* \* \* \* \*